(12) United States Patent
Brackett et al.

(10) Patent No.: US 7,999,110 B2
(45) Date of Patent: Aug. 16, 2011

(54) SOLID STATE FORMS OF RACEMIC ILAPRAZOLE

(75) Inventors: John M. Brackett, Kenosha, WI (US); David T. Jonaitis, Lafayette, IN (US); Wei Lai, West Lafayette, IN (US); Jih Hua Liu, Green Oaks, IL (US); Stephan D. Parent, West Lafayette, IN (US); Jinyu Shen, Edmonton (CA)

(73) Assignee: IL Yang Pharmaceutical Company, Ltd., Yongi-si, Gyeonggi-Do (KR)

( * ) Notice: Subject to any disclaimer, the term of this patent is extended or adjusted under 35 U.S.C. 154(b) by 721 days.

(21) Appl. No.: 11/966,868

(22) Filed: Dec. 28, 2007

(65) Prior Publication Data

US 2008/0200516 A1 Aug. 21, 2008

Related U.S. Application Data

(60) Provisional application No. 60/877,608, filed on Dec. 29, 2006, provisional application No. 60/887,499, filed on Jan. 31, 2007.

(51) Int. Cl.
*C07D 401/14* (2006.01)
(52) U.S. Cl. .................................... 546/273.7
(58) Field of Classification Search ............... 546/273.7; 514/338
See application file for complete search history.

(56) References Cited

U.S. PATENT DOCUMENTS 6,627,646 B2 * 9/2003 Bakale et al. ................. 514/322

FOREIGN PATENT DOCUMENTS

| WO | 95/23140 | * | 8/1995 |
| WO | WO 95/23140 A | | 8/1995 |
| WO | WO 2006/099810 A | | 9/2006 |
| WO | WO 2006/118534 A | | 11/2006 |

OTHER PUBLICATIONS

Kim et al. II, "IY-81149, etc.," Drugs of the Future 1999, 24(6), 618-621.*
Kil et al., "Comparison of, etc.," Journal of Autonomic Pharmacology, 2000, 20, 291-296.*
Chemical & Engineering News, Feb. 2003, 32-35.*
Brittain ed., "Polymorphism, etc.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*
Rowland & Tozer, "Clinical Pharmacokinetics, etc.," 1995, p. 123.*
Silverman, The Organic Chemistry of Drug Design and Drug Action, NY: Academic Press, 1993, 72-76.*
Ulicky. Comprehensive Dictionary of Physical Chemistry, NY: Prentice Hall, 1992, p. 21.*
Doelker, english translation of Ann. Pharm. Fr., 2002, 60: 161-176, pp. 1-39.*
Doelker, english translation of S.T.P, Pratiques (1999), 9(5), 399-409, pp. 1033.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*
International Search Report for PCT/US2007/089127 dated May 15, 2008.
Kim et al., "TY-81149: Antiulcerative $H^+/K^+$-ATPase Inhibitor," Drugs of the Future, 24(6), 618-621, 1999.

* cited by examiner

*Primary Examiner* — Patricia Morris
(74) *Attorney, Agent, or Firm* — Nixon Peabody LLP

(57) ABSTRACT

The invention relates to crystalline forms of racemic ilaprazole, 2[[(4-methoxy-3-methyl-2 -pyridinyl)-methyl]sulfinyl]-5-(1 H-pyrrol-1-yl) 1H-Benzimidazole. The invention also relates to a pharmaceutical composition for inhibiting gastric acid secretion comprising a crystalline Form of ilaprazole according to the invention in an amount effective to inhibit gastric acid secretion and a pharmaceutically acceptable carrier. The invention also provides methods of treatment for various acid-related gastrointestinal (GI) disorders.

3 Claims, 57 Drawing Sheets

SOLID STATE FORMS OF RACEMIC ILAPRAZOLE

PRIORITY STATEMENT

This application claims benefit under 35 U.S.C. §119(e) of U.S. Provisional Application No. 60/877,608, filed Dec. 29, 2006 and U.S. Provisional Application No. 60/887,499, filed Jan. 31, 2007, both of which are herein incorporated by reference in their entirety.

FIELD OF THE INVENTION

This invention relates to ilaprazole, 2[[(4-methoxy-3-methyl-2-pyridinyl)-methyl]sulfinyl]-5-(1H-pyrrol-1-yl) 1H-Benzimidazole, a substituted benzimidazole having a chiral sulfur atom. More particularly, the invention relates to solid state forms of racemic ilaprazole. Ilaprazole is a proton pump inhibitor and is useful in the treatment of various acid-related gastrointestinal disorders.

BACKGROUND OF THE INVENTION

Since their introduction in the late 1980s, proton pump inhibitors have improved the treatment of various acid-related gastrointestinal (GI) disorders, including gastroesophageal reflux disease (GER)), peptic ulcer disease, Zollinger-Ellison Syndrome (ZES), ulcers, and nonsteroidal anti-inflammatory drug (NSAID)-induced gastropathy. GEMD encompasses three disease categones: non-erosive reflux disease (NERD), erosive esophagitis, and Barrett's esophagus. ZES is caused by a gastrin-secreting tumor of the pancreas that stimulates the acid-secreting cells of the stomach to maximal activity. Proton pump inhibitors have also be used to treat ulcers such as duodenal, gastric, and NSAID-associated gastric/duodenal ulcers.

As antisecretory drugs, proton pump inhibitors are currently the recommended first line therapy, being viewed as more effective than other treatments. In general, proton pump inhibitors offer superior gastric acid suppression over histamine H2-receptor blockers. The use of proton pump inhibitors by patients who suffer from gastric acid-related disorders is generally believed to have led to an increase in their quality of life, productivity, and overall well being.

Proton pump inhibitors are also used to treat extra-esophageal manifestations of GER) (asthma, hoarseness, chronic cough, non-cardiac chest pain), and with antibiotics for *Helicobacter pylori* eradication. The goals of GER) management are threefold: prompt and sustained symptom control, healing of the injured esophageal mucosa and prevention of GERD-related complications (including stricture Formation, Barrett's esophagus, and/or adenocarcinoma). Pharmacological therapy with proton pump inhibitors Forms the basis of both acute and long-term management of GERD. Proton pump inhibitors provide effective relief of symptoms and healing of the esophagitis, as well as sustaining long-term remission.

Although therapeutic efficacy is the primary concern for a therapeutic agent, the solid-state form, as well as the salt form, and the properties unique to the particular form of a drug candidate are often equally important to its development. Each solid state form (crystalline or amorphous) of a drug candidate can have different physical and chemical properties, for example, solubility, stability, or the ability to be reproduced. These properties can impact the ultimate pharmaceutical dosage form, the optimization of manufacturing processes, and absorption in the body. Moreover, finding the most adequate form for further drug development can reduce the term and the cost of that development.

Obtaining substantially pure crystalline, amorphous or even other non-crystalline forms is extremely useful in drug development. It permits better characterization of the drug candidate's chemical and physical properties and thereby allows identification of the form or forms with the desired combination of therapeutic effect and comparative ease of manufacture. The solid state crystalline form may possess more favorable pharmacology than the amorphous form or may be easier to process. It may also possess more storage stability.

The solid state physical properties of a drug candidate may also influence its selection as a pharmaceutical active ingredient and the choice of form for its pharmaceutical composition. One such physical property, for example, is the flowability of the solid, before and after milling. Flowability affects the ease with which the material is handled during processing into a pharmaceutical composition. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate. Another important solid state property of a pharmaceutical compound is its dissolution rate in aqueous fluid. The rate of dissolution of an active ingredient in a patient's gastrointestinal fluid may have therapeutic consequences since it impacts the rate at which an orally-administered active ingredient may reach the patient's bloodstream.

These practical physical properties are influenced by the properties of the particular solid state form of the compound, for example, by the conformation and orientation of molecules in the unit cell of the crystalline compound. A crystalline form often has different thermal behavior characteristics from an amorphous, a non-crystalline form or another polymorphic form. Thermal behavior is measured in the laboratory by such techniques as capillary melting point, thermogravimetric analysis (TGA) and differential scanning calorimetry (DSC) and may be used, for example, to distinguish some polymorphic forms from others. A particular solid state form generally possesses distinct crystallographic and spectroscopic properties detectable by powder X-ray diffraction (XRPD), single crystal X-ray crystallography, solid state NMR, and infrared spectrometry among other techniques.

SUMMARY OF THE INVENTION

The invention relates to solid state forms of racemic ilaprazole, 2-[[(4-methoxy-3-methyl-2-pyridinyl)-methyl]sulfinyl]-5-(1H-pyrrol-1-yl) 1H-Benzimidazole. The invention also relates to a pharmaceutical composition for inhibiting gastric acid secretion comprising a crystalline form of racemic ilaprazole according to the invention in an amount effective to inhibit gastric acid secretion and a pharmaceutically acceptable carrier. The invention also provides methods of treatment for various acid-related gastrointestinal (GI) disorders such as those discussed above.

DETAILED DESCRIPTION OF THE INVENTION

Figure 1:
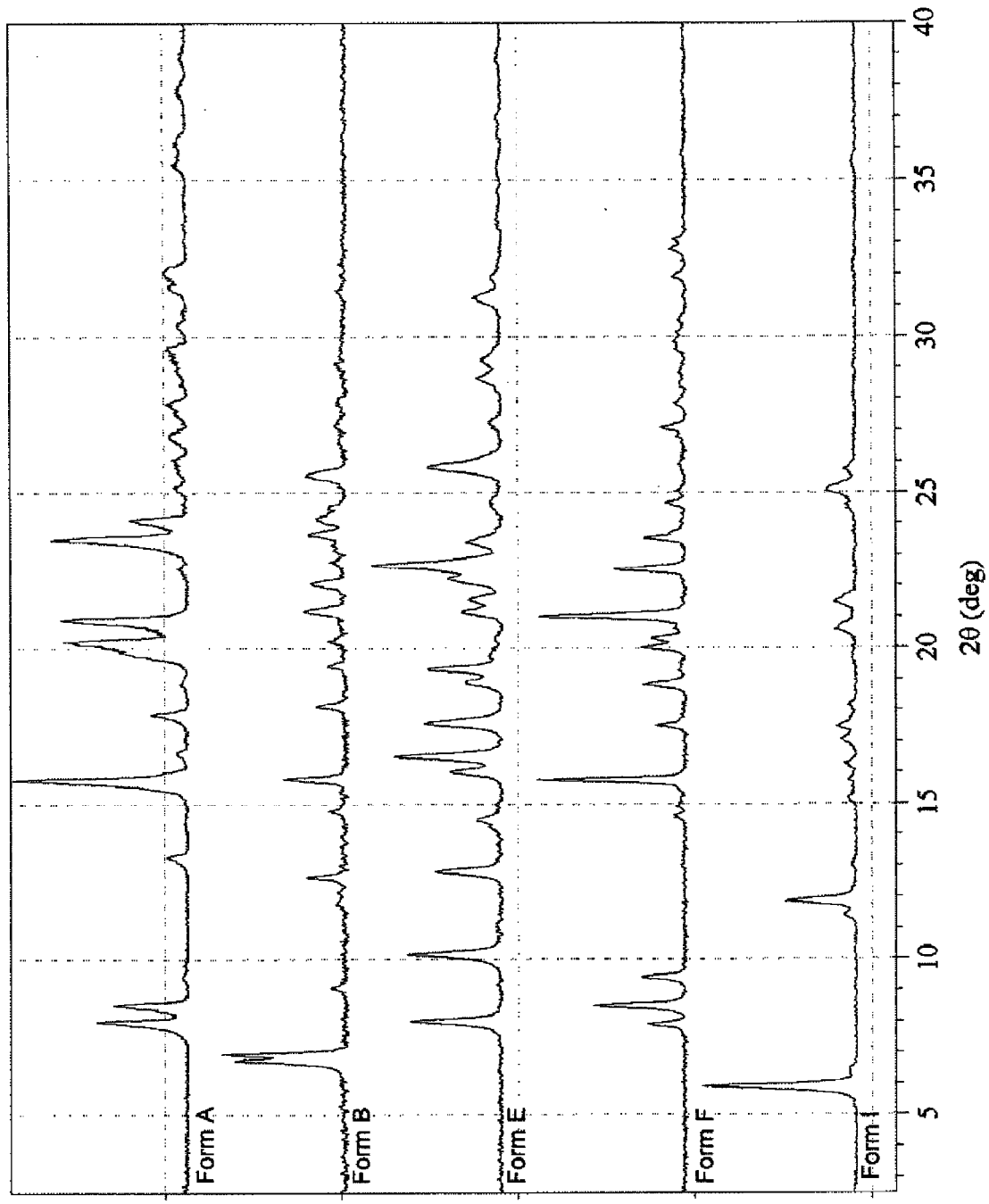
FIG. 1 is a comparison of the XRPD patterns of the crystalline forms of racemic ilaprazole.
Figure 2:
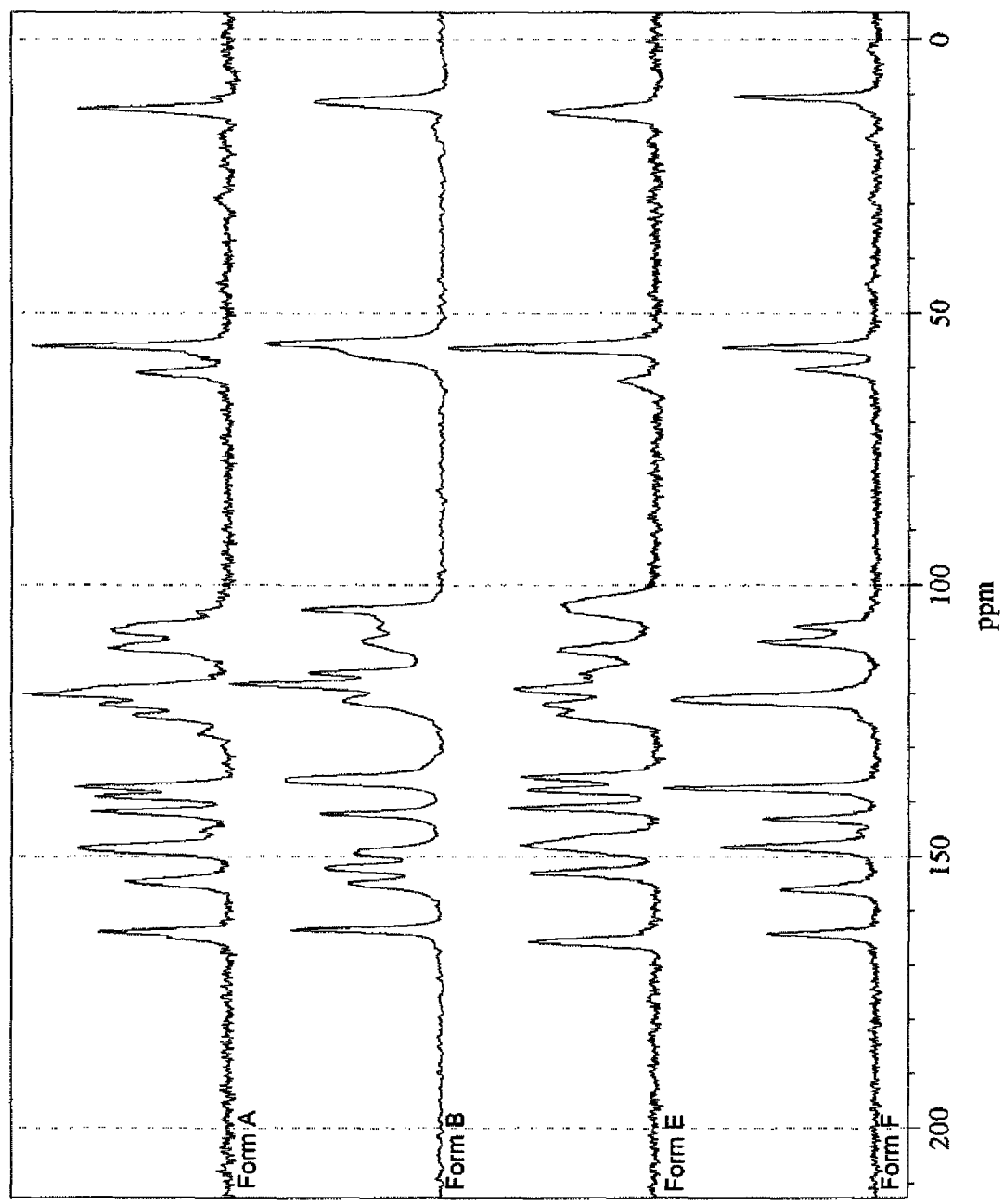
FIG. 2 is a comparison of the solid state $^{13}$C CP/MAS NMR spectra of crystalline Forms A, B, E, and F of racemic ilaprazole.
Figure 3:
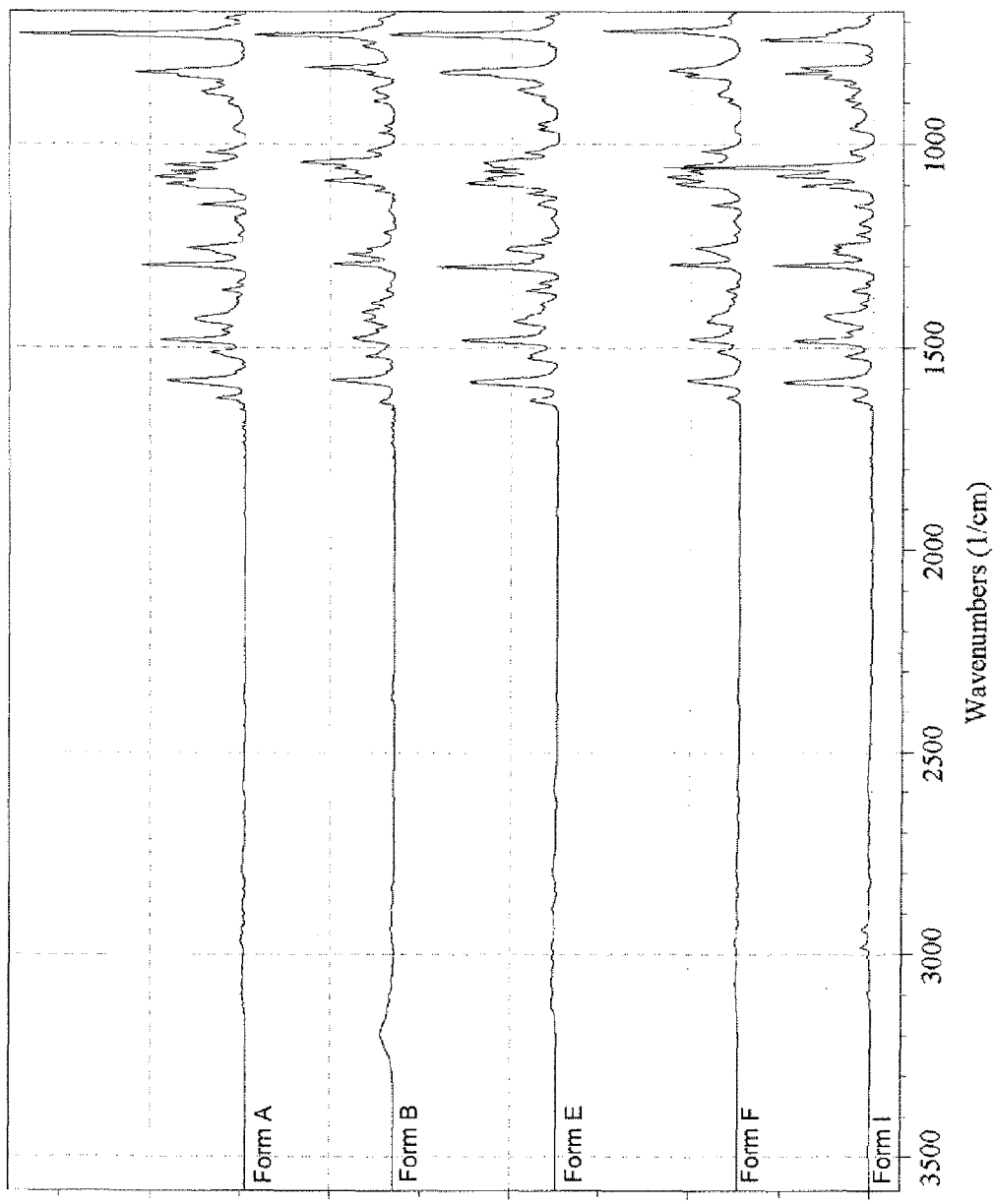
FIG. 3 is a comparison of the IR spectra of the crystalline forms of racemic ilaprazole.
Figure 4:
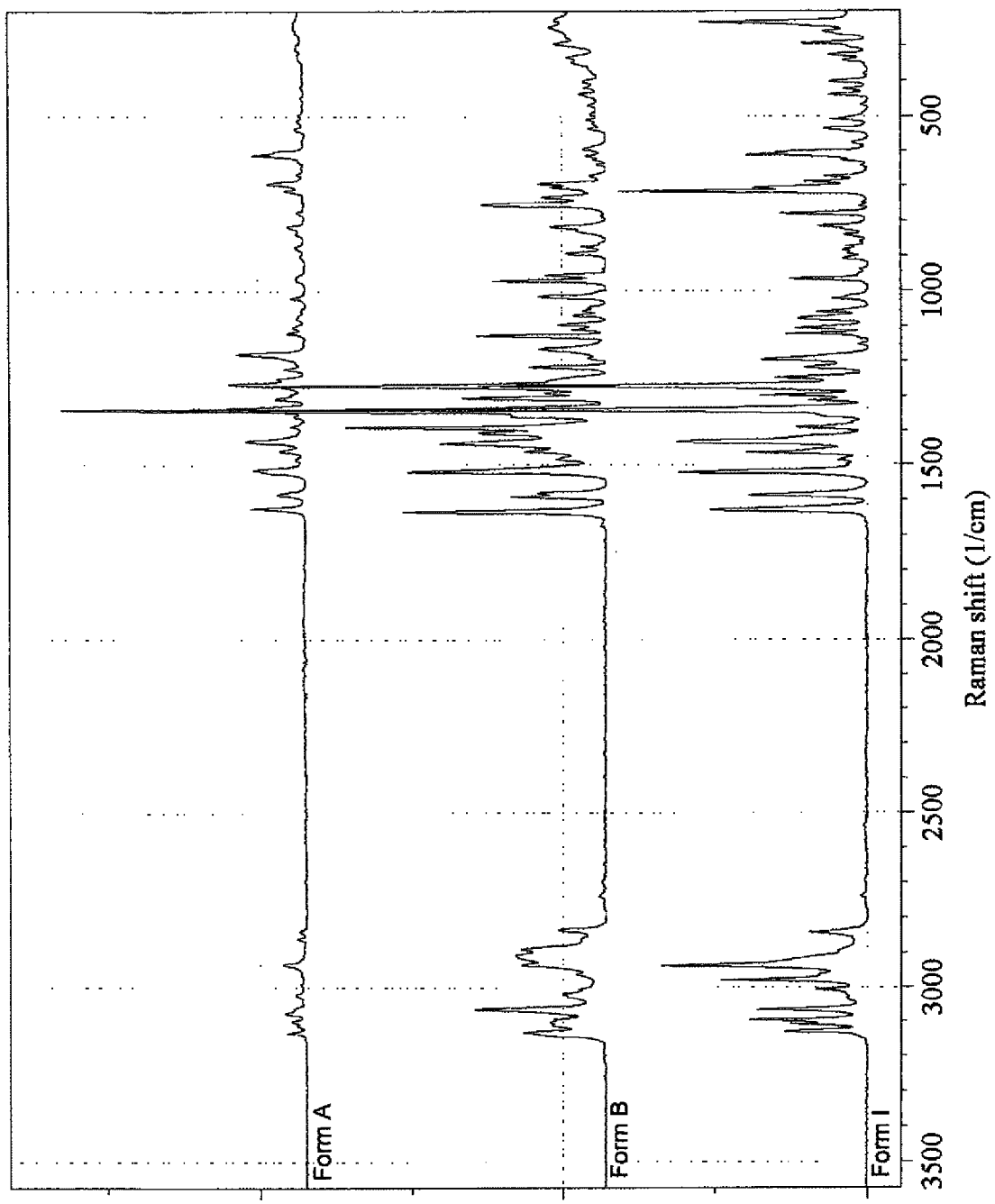
FIG. 4 is a comparison of the Raman spectra of crystalline Forms A, B, and I of racemic ilaprazole.

Ilaprazole, 2-[[(4-methoxy-3-methyl-2-pyridinyl)-methyl]sulfinyl]-5-(1H-pyrrol-1-yl) 1H-Benzimidazole, is a substituted benzimidazole that acts as a proton pump inhibitor. Ilaprazole selectively and irreversibly inhibits gastric acid secretion through inhibition of the hydrogen-potassium adenosine triphosphatase (H+K+-ATPase) (proton pump) mechanism. Inhibition of the proton pump occurs by formation of disulfide covalent bonds with accessible cysteines on the enzyme. Ilaprazole has a prolonged duration of action that persists after their elimination from plasma. See, for example, U.S. Pat. Nos. 5,703,097 and 6,280,773, which are incorporated herein by reference.

Ilaprazole has the empirical formula $C_{19}H_{18}N_4O_2S$ having a molecular weight of 366.44 daltons. Ilaprazole is a chiral molecule and has the following structural Formula (I):

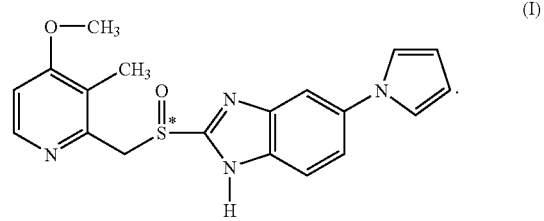

(I)

Ilaprazole, like all proton pump inhibitors, possesses the unique feature of a chiral sulfur atom, S*. This can be depicted as follows with the lone pair of electrons on the chiral sulfur atom occupying one position in each stereoisomer, as shown below:

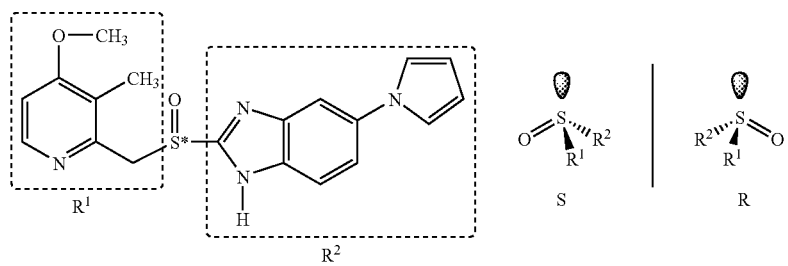

The absolute structure and absolute confirmation of (−)-S-ilaprazole was made through single crystal structure determination and is shown below. See Example 7 of co-pending U.S. application Ser. No. 11/966,808 of Brackett et al. entitled, "Solid State Forms of Enantiopure Ilaprazole" filed Dec. 28, 2007, herein incorporated by reference in its entirety.

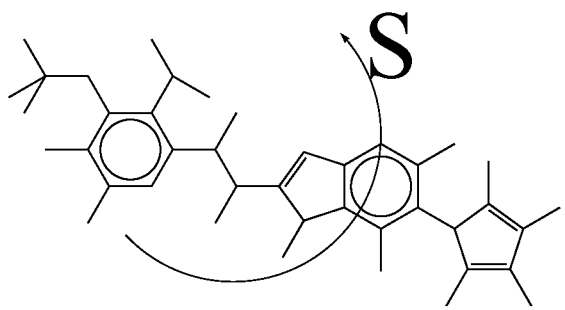

Thus, its complimentary enantiomer is (+)-R-ilaprazole, as shown below.

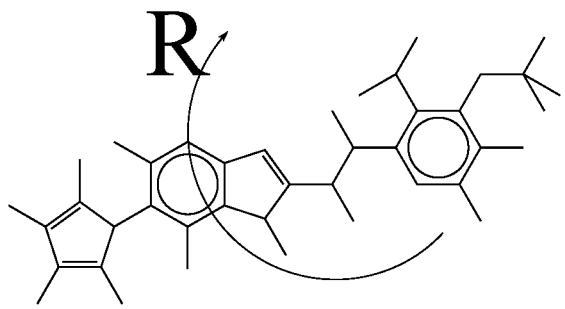

Chiral molecules are well known to chemists. Chiral molecules exist in two enantiomorphic forms that are mirror images of each other. In the same manner that left and right hands are mirror images of each other and cannot be superimposed over each other, enantiomers of chiral molecules cannot be superimposed over each other. The only difference in the molecules is the arrangement of groups connected to the chiral center in three dimensional space. The physical properties of enantiomers are identical to each other with the exception of the rotation of the plane of polarized light. It is this rotation of polarized light that allows one skilled in the art to determine if a chiral material is enantiomerically pure.

In the solid state, pure enantiomeric materials (also known as enantiopure materials) are, by definition, composed of a single enantiomer and can have very different properties compared to racemates. This is particularly true in the crystalline form. Racemates can crystallize as a conglomerate (where the two enantiomers form identical, mirror-image crystals that are the pure enantiomer), a racemic compound (where the two enantiomers coexist and are incorporated into specific locations of the crystal) or a solid solution (where the enantiomers can be located at random sites within the crystal). The solid state can be characterized by various physical properties such as solubility, melting point, x-ray powder diffraction, solid state NMR, Raman, and IR spectroscopy.

The solid state forms of racemic ilaprazole of the invention are designated as Forms A, B, E, F, and I. Each crystalline form of racemic ilaprazole of the invention is described in the Examples below. FIGS. 1-4 are comparison figures showing the XRPD patterns, the solid state $^{13}$C CP/MAS NMR spectra, the IR spectra, and the Raman spectra of the crystalline forms of racemic ilaprazole according to the invention. The different crystalline forms of racemic ilaprazole can be identified or characterized by comparing their respective spectra. Similarities may also be seen, such as the common XRPD peak at 15.8° 2θ±0.2° 2θ. The proton NMR spectra are useful in showing that each ilaprazole form is chemically the same as the starting material. Additional data for each crystalline form which may be used to identify each form is presented in the Examples below. Each form disclosed here possesses advantages vis-à-vis the other forms, for example, for a particular formulation or processing.

The term "racemic" or "racemate," is defined as a 1:1 mixture of the two enantiomers of ilaprazole regardless of their physical state. A racemic mixture of ilaprazole can be composed of individual crystals which may be the pure enantiomers or ratios of the R and S enantiomers, such as 90/10, 10/90, 86/14, 14/86, 70/30, 30/70, 50/50, as well as other ratios in between these ratios, as long as the bulk enantiomeric composition remains 1:1.

The forms of racemic ilaprazole of the invention are each substantially pure or substantially free of the other crystalline forms or amorphous racemic ilaprazole and other impurities. In this context, "substantially pure" means that the particular form of racemic ilaprazole comprises less than 15% of another crystalline or amorphous form. The purity is preferably less than 10%, more preferably less than 5%, more preferably less than 2%, more preferably less than 1%, and even more preferably less than 0.5%. The term "substantially pure" also means that the form of racemic ilaprazole comprises less than 3% of other impurities, preferably less than 2%, more preferably less than 11%, and even more preferably less than 0.5%.

Racemic ilaprazole Form A is the most thermodynamically stable of these crystalline Forms. Form A is also the least soluble in aqueous solutions. It is not hygroscopic. A human bioavailability study of Forms A, B, and F, described in Example 9, showed Form A to be also the most bio-available form in humans. This is a surprising and unexpected combination of characteristics which causes racemic ilaprazole Form A to be a preferred form for solid dosage forms of the invention.

Racemic ilaprazole, Form A crystallizes with the monoclinic space group P2$_1$, which is not centrosymmetric (i.e. does not contain a center of symmetry). Surprisingly, unequal numbers of R and S isomers can coexist within this structure. Three Form A single crystal structures were determined. While not wishing to be bound by theory, it believed that an individual crystal of Form A contains an approximate 70/30 (or 30/70) mixture of the R and S isomers. The arrangement of isomers appears disordered and is manifest in the crystallographic data as two atomic positions for the single oxygen bound to the chiral sulfur of the sulfoxide group. It is believed that each oxygen position represents one isomer and is partially occupied (e.g. one position is 70% R(S) occupied and the other is 30% S(R) occupied).

Structures were determined for both enantiomeric compositions. Two of the predicted structures contained enantiomeric ratios of approximately 70-30 while another had a ratio of approximately 28-72, suggesting that such a ratio is preferred under these conditions. However, the bulk material is racemic, as demonstrated by a net 0° rotation of plane polarized light, indicating that the bulk material contains approximately equal numbers of crystals with ratios of 70% R/30% S and 30% R/70% S.

Chiral HPLC analysis was performed on a single crystal of Form A for which the structure had been determined. The result was consistent with enantiomeric enrichment of one isomer, whereas the analysis of bulk racemic ilaprazole, Form A material was consistent with a 50/50 racemic mixture. When crystallized from racemic solution at ambient temperature, Form A can be characterized as a solid solution in which individual crystals may contain mixture of the R and S isomers. This behavior is similar to that described by a conglomerate, except that a conglomerate is composed of equal numbers of pure S and pure R crystals.

Racemic ilaprazole Form F is believed to be a kinetically favored crystal form. Under certain conditions, e.g., temperatures, aqueous mixed solvent composition, and pH gradients, Form F is more soluble in aqueous solvents than Form A. Solubility studies are shown in Example 6. Like Form B, Form F is less bioavailable than Form A. It too may be used to prepare longer acting pharmaceutical compositions. Form F has the longest half-life of the crystalline Forms A, B, and F which were evaluated in the bioavailability study of Forms A, B, and F, Example 9. Form F is slightly hygroscopic.

Form F crystallizes with the centrosymmetric space group P2$_1$/n which must contain a center of symmetry. Each crystal must contain an equal number of R and S isomers. Thus, Form F is a racemic crystal. The arrangement of isomers within this structure is disordered. There are two oxygen atom positions for the oxygen bound to the chiral sulfur of the sulfoxide group, each partially occupied in an 86/14 ratio. At first glance this seems similar to the Form A structure, but the presence of a center of symmetry in the space group of the Form F structure dictates it be racemic. Therefore, individual Form F crystals must contain an equal number of both enantiomers. In the disordered Form F structure, half of the crystallographic sites have an enantiomeric or occupancy ratio of approximately 86/14 and other half have the opposite ratio of approximately 14/86. Chiral HPLC and optical rotation analysis confirms that both the single crystals of Form F and the bulk material are racemic.

Racemic ilaprazole Form B crystallizes in pure form from aprotic solvents such as acetone or dichloromethane/ethyl acetate. This leads to a manufacturing advantage. For example, Form B may be used to purify ilaprazole. Form B is also a stable crystalline form having good long term stability or shelf life. Form B is more soluble in aqueous solvents than Form A. The bioavailability study of Forms A, B, and F, discussed in Example 9, showed that Form B has a greater half-life than Form A which may be advantageously used to prepare longer acting pharmaceutical compositions. Form B is not hygroscopic.

Forms B, E, and I are racemic crystalline forms of ilaprazole whose individual crystal structures have not been determined. Although the enantiomeric composition of the individual crystal structure is not known, chiral HPLC confirms that the bulk composition of each of these forms is racemic, i.e. contains an equimolar mixture of each enantiomer. As mentioned above, the x-ray powder diffraction (XRPD) patterns the solid state $^{13}$C CPMAS NMR spectra, the IR spectra, and the Raman spectra obtained on these forms show characteristic peaks which identify each form. As shown in the Examples, the physical properties of Forms A, B, F, and I, such as melt onset temperature and moisture sorption/desorption profiles, also differ depending on the particular form.

Pharmaceutical Compositions and Methods

Ilaprazole is useful for inhibiting gastric acid secretion as well as for providing gastrointestinal cytoprotective effects in mammals, including humans. In a more general sense, ilaprazole may be used for prevention and treatment of gastrointestinal inflammatory diseases in mammals, including e.g. gastritis, gastric ulcer, and duodenal ulcer. As discussed above, such GI disorders include, for example, gastroesophageal reflux disease (GERD), peptic ulcer disease, Zollinger-Ellison Syndrome (ZES), ulcers, and nonsteroidal anti-inflammatory drug (NSAID)-induced gastropathy. Ilaprazole may also be used for prevention and treatment of other gastrointestinal disorders where cytoprotective and/or gastric antisecretory effect is desirable, e.g. in patients with gastrinomas, in patients with acute upper gastrointestinal bleeding, and in patients with a history of chronic and excessive alcohol consumption.

The results of Phase 1 clinical studies conducted with ilaprazole results suggest that at the doses studied, suppression of gastric acid occurs over a 24-hour period. In Phase 2 clinical studies conducted with ilaprazole, the results indicated that ilaprazole at the doses studied provided symptomatic relief for patients with gastric-acid related disorders and promoted rapid healing of acid-related gastric and duodenal ulcers.

Accordingly, the invention relates to a pharmaceutical composition for inhibiting gastric acid secretion comprising a crystalline form of racemic ilaprazole according to the invention in an amount effective to inhibit gastric acid secretion and a pharmaceutically acceptable carrier. Pharmaceutical compositions are discussed below.

The invention also relates to the treatment of various acid-related gastrointestinal (GI) inflammatory diseases and disorders such as those discussed above and providing gastrointestinal cytoprotection. The invention provides a method for inhibiting gastric acid secretion by administering to mammals a crystalline form of racemic ilaprazole according to the invention, or a pharmaceutical composition containing it, in an amount sufficient to inhibit gastric acid secretion. The invention also provides a method for the treatment of gastrointestinal inflammatory diseases in mammals by administering to mammals a crystalline form of racemic ilaprazole according to the invention, or a pharmaceutical composition containing it, in an amount sufficient to treat gastrointestinal inflammatory disease. The invention further provides a method for providing gastrointestinal cytoprotective effects in mammals by administering to mammals a crystalline form of racemic ilaprazole according to the invention, or a pharmaceutical composition containing it, in an amount sufficient to provide gastrointestinal cytoprotective effects.

The invention relates to pharmaceutical compositions comprising a therapeutically effective amount of a crystalline form of racemic ilaprazole of the invention and a pharmaceutically acceptable carrier, (also known as a pharmaceutically acceptable excipient). The pharmaceutical composition may also contain a mixture of crystalline form of racemic ilaprazole. As discussed above, the crystalline forms of racemic ilaprazole are useful for the treatment of various acid-related gastrointestinal (GI) disorders. Pharmaceutical compositions for the treatment of those diseases and disorders contain a therapeutically effective amount of a crystalline form of racemic ilaprazole of the invention to inhibit gastric secretion as appropriate for treatment of a patient with the particular disease or disorder.

A "therapeutically effective amount of a crystalline form of racemic ilaprazole to inhibit gastric secretion" (discussed here concerning the pharmaceutical compositions) refers to an amount sufficient to inhibit or reduce gastric secretion and thereby to treat, i.e. to reduce the effects, inhibit or prevent, various acid-related gastrointestinal (GI) disorders and/or provide gastrointestinal cytoprotection. The actual amount required for treatment of any particular patient will depend upon a variety of factors including the disorder being treated and its severity; the specific pharmaceutical composition employed; the age, body weight, general health, sex and diet of the patient; the mode of administration; the time of administration; the route of administration; and the rate of excretion of the crystalline form of racemic ilaprazole according to the invention; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference.

The absorption of the crystalline forms of racemic ilaprazole can be altered depending on when the subject consumes food in relation to when the dosage is administered. The rate of absorption can also depend on the type of diet consumed, particularly if the diet has a high concentration of fats. These factors, as well as others known to those of skill in the art that can affect the absorption of proton pump inhibitors, can consequently influence the efficacy of the crystalline forms of racemic ilaprazole in inhibiting gastric acid secretion. It has been found that the absorption of the crystalline forms of racemic ilaprazole can be delayed and the bioavailability increased when administered in the fed state or approximately five minutes before a high-fat meal, compared to administration in the fasted state. Administration of the crystalline forms of racemic ilaprazole approximately one hour before a high-fat meal produces results similar to that observed during administration in the fasted state. These findings are consistent with similar studies performed with other tableted formulations of proton pump inhibitors.

A pharmaceutical composition of the invention may be any pharmaceutical form which contains and retains the crystalline form of racemic ilaprazole according to the invention. The pharmaceutical composition may be, for example, a tablet, capsule, liquid suspension, injectable, topical, or transdermal. A comprehensive disclosure of suitable formulations (including controlled-release formulations, e.g. delayed release, sustained/extended release, etc.) may be found in U.S. Published Application No. 2006/013868, herein incorporated by reference in its entirety. For injectables and liquid suspensions, those should be formulated such that the crystalline form of racemic ilaprazole is present in the formulated composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. For a pharmaceutical composition of the invention, that is one having a crystalline form of racemic ilaprazole of the invention, a carrier should be chosen that maintains the crystalline form of racemic ilaprazole of the invention. In other words, the carrier should not substantially alter the crystalline form of the racemic ilaprazole of the invention. Nor should the carrier be otherwise incompatible with a crystalline form of racemic ilaprazole according to the invention, such as by producing any undesirable biological effect or otherwise interacting in a deleterious manner with any other component(s) of the pharmaceutical composition.

The pharmaceutical compositions of the invention are preferably formulated in unit dosage form for ease of administration and uniformity of dosage. A "unit dosage form" refers to a physically discrete unit of therapeutic agent appropriate for the patient to be treated. It will be understood, however, that the total daily dosage of a crystalline form of racemic ilaprazole of the invention and its pharmaceutical compositions according to the invention will be decided by the attending physician within the scope of sound medical judgment.

It may be desirable to administer the dosage in a composition where the crystalline form of racemic ilaprazole is released from the dosage form as a first and a second dose where each of the first and second dose contain a sufficient amount of the crystalline form of racemic ilaprazole to raise plasma levels to a desired concentration. Suitable formulations to achieve this are disclosed in PCT Published Application No. WO 2006/009602, herein incorporated by reference in its entirety.

Because the crystalline form of racemic ilaprazole of the invention is more easily maintained during their preparation, solid dosage forms are preferred for the pharmaceutical composition of the invention. Solid dosage forms for oral administration, which includes capsules, tablets, pills, powders, and granules, are particularly preferred. In such solid dosage forms, the active compound is mixed with at least one inert, pharmaceutically acceptable carrier (also known as a pharmaceutically acceptable excipient). The solid dosage form may, for example, include one or more pharmaceutical carriers/excipients as known in the art, including: a) fillers or extenders such as starches, lactose, lactose monohydrate, sucrose, glucose, mannitol, sodium citrate, dicalcium phosphate, and silicic acid; b) binders such as, for example, carboxymethylcellulose, microcrystalline cellulose, alginates, gelatin, polyvinylpyrrolidinone, sucrose, and acacia; c) humectants such as glycerol; d) disintegrating agents such as agar, calcium carbonate, potato or tapioca starch, alginic acid, certain silicates, sodium starch glycolate, and sodium carbonate; e) dissolution retarding agents such as paraffin; f) absorption accelerators such as quaternary ammonium compounds; g) wetting agents such as, for example, cetyl alcohol and glycerol monostearate; h) absorbents such as kaolin and bentonite clay; i) lubricants such as talc, calcium stearate, magnesium stearate, magnesium hydroxide, solid polyethylene glycols, sodium lauryl sulfate; and j) glidants such as colloidal silicon dioxide. The solid dosage forms may also comprise buffering agents. They may optionally contain opacifying agents and can also be of a composition that they release the active ingredient(s) only, or preferentially, in a certain part of the intestinal tract and/or optionally in a delayed manner Remington's Pharmaceutical Sciences, Sixteenth Edition, E. W. Martin (Mack Publishing Co., Easton, Pa., 1980), herein incorporated by reference in its entirety, discloses various carriers used in formulating pharmaceutical compositions and known techniques for the preparation thereof. Solid dosage forms of pharmaceutical compositions of the invention can also be prepared with coatings and shells such as enteric coatings and other coatings well known in the pharmaceutical formulating art, including formulations and coatings designed to provide for extended release of the active pharmaceutical ingredient (API). For example, U.S. Pat. No. 6,605,303, incorporated herein by reference, describes oral extended release formulations for the proton pump inhibitor omeprazole. Accordingly, the solid dosage form may be an extended or delayed release formulation. An exemplary delayed-release tablet formulation is described in Example 8, below.

A crystalline form of racemic ilaprazole of the invention can also be in a solid micro-encapsulated form with one or more carriers as discussed above. Microencapsulated forms of a crystalline form of racemic ilaprazole of the invention may also be used in soft and hard-filled gelatin capsules with carriers such as lactose or milk sugar as well as high molecular weight polyethylene glycols and the like.

The invention also provides methods for the treatment of the GI disorders discussed above. The solid forms of racemic ilaprazole and pharmaceutical compositions containing them may, according to the invention, be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this invention can be administered to humans and other animals orally, rectally, parenterally, intraveneously, intracistemally, intravaginally, intraperitoneally, topically (as by powders, ointments, or drops), bucally, as an oral or nasal spray, or the like, depending on the location and severity of the condition being treated. As discussed above, when administering a pharmaceutical compositions of the invention via one of these routes, the pharmaceutical composition contains racemic ilaprazole in one of the crystalline forms of the invention. Oral administration using tablets or capsules is generally preferred.

In certain embodiments, the crystalline forms of racemic ilaprazole according to the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. For extended release formulations, the dosage may range from about 5 mg to about 80 mg, preferably ranging from about 10 mg to about 50 mg ilaprazole, and more preferably ranging from about 20 mg to about 40 mg.

EXAMPLES

Example 1 describes the preparation of ilaprazole. Examples 24 describe the preparation and characterization of three crystalline forms of racemic ilaprazole, Forms A, F and I. These solid state forms were characterized by various techniques. Each technique is described below. Example 5 describes solubility studies of racemic ilaprazole Forms A and F. Examples 6 and 7 describe the preparation and characterization of two additional crystalline forms of racemic ilaprazole, Forms B and E. Example 8 describes delayed release tablet formulations containing racemic ilaprazole Forms A, B, and F. Example 9 describes a human bioavailability study with those delayed release tablets.

Differential Scanning Calorimetry (DSC); Analyses were carried out on a TA Instruments differential scanning calorimeter 2920 or Q1000. The instrument was calibrated using indium as the reference material. The sample was placed into an aluminum DSC pan and the weight accurately recorded. The sample cell was equilibrated at 25° C. and heated under a nitrogen purge at a rate of 10° C./min or 40° C./min, up to a final temperature of 350° C. Specific heating rates and pan configurations are identified in the comment section above each individual thermogram. Pan configurations are defined as follows: NC is non-crimped and HSP is hermetically sealed.

Dynamic Vapor Sorption/Desorption (DVS). Data were collected on a VTI SGA-100 moisture balance system. For sorption isotherms, a sorption range of 5 to 95% relative humidity (RH) and a desorption range of 95 to 5% RH in 10% RH increments were used for analysis. The samples were not dried prior to analysis. Equilibrium criteria used for analysis were less than 0.0100% weight change in 5 minutes with a maximum equilibration time of 3 hours if the weight criterion was not met. Data were not corrected for the initial moisture content of the samples.

IR Spectroscopy: Infrared spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. An attenuated total reflectance (ATR) accessory (Thunderdome™, Thermo Spectra-Tech), with a germanium (Ge) crystal was used for data acquisition. The spectra represent 256 co-added scans collected at a spectral resolution of 4 $cm^{-1}$. A background data set was acquired with a clean Ge crystal. Log 1/R (R reflectance) spectra were acquired by taking a ratio of these two data sets against each other. Wavelength calibration was performed using polystyrene.

Solution State $^1$H NMR Analyses: Samples were prepared for $^1$H NMR spectroscopy as ~5-50 mg solutions in deuterated methylene chloride, $CD_2Cl_2$. The spectra were obtained on an INOVA-400 spectrometer. The spectra were obtained with the acquisition parameters in Table 1.

TABLE 1

| $^1$H NMR Acquisition Parameters | |
|---|---|
| Solvent: | $CD_2Cl_2$, (internal reference at 5.32 ppm) |
| Temperature: | Ambient |
| Spin rate: | 20 Hz |
| Pulse sequence: | s2pu1 |
| Relaxation delay: | 5 seconds |
| Pulse width: | 8.4 μseconds, (90.0 degree) |
| Acquisition time: | 2.5 seconds |
| Spectral width: | 6400.0 Hz, (16.008 ppm) |
| Scans: | 40 |
| Acquired points: | 32000 |
| Data processing: | |
| Line broadening: | 0.2 Hz |
| FT size: | 131072 |

Solid State $^{13}$C CP/MAS NMR Analyses (ssNMR). Samples were prepared for solid-state NMR spectroscopy by packing them into 4 mm PENCIL type zirconia rotors. The spectra were acquired on an INOVA-400 spectrometer using $^1$H cross-polarization (CP) and magic angle spinning, (MAS). The specific acquisition parameters are listed in Table 2, with exceptions noted for different examples.

TABLE 2

$^{13}$C ssNMR Acquisition Parameters

| | |
|---|---|
| Reference: | Glycine (external reference at 176.5 ppm) |
| Temperature: | Ambient |
| Pulse sequence: | xpolvtlrho1 |
| Relaxation delay: | 10 seconds |
| Pulse width: | 2.2 μseconds, (90.0 degree, 76.2 degree for Form E (Example 7)) |
| Acquisition time: | 0.030 seconds |
| Spectral width: | 44994.4 Hz, (447.517 ppm) |
| Scans: | 100 for Forms A and F (Examples 2 and 3); 200 with 2 dummy scans for Form B (Example 6); 400 with 2 dummy scans for Form E (Example 7) |
| Acquired points: | 27000 |
| $^1$H Decoupling SPINAL-64 decoupling Cross Polarization tangent RAMP-CP on C13 | 400 MHz |
| Contact Time: | 5.0 mseconds |
| Spin rate: | 12000 Hz |
| Data processing: | |
| Backward linear prediction: | 3 points |
| Line broadening: | 10.0 Hz |
| FT size: | 3278 |

Thermogravimetric Analysis (TGA): Thermogravimetric analyses were carried out on a TA Instruments 2950 thermogravimetric analyzer. The calibration standards were nickel and Alumel™. Each sample was placed in an aluminum sample pan and inserted into the TG furnace. Samples were started directly from ambient and then heated under a stream of nitrogen at a heating rate of 10° C./min, up to a final temperature of 350° C.

Raman Spectroscopy: Fourier Transfrom-Raman spectra were acquired on an FT-Raman 960 spectrometer (Thermo Nicolet). This spectrometer uses an excitation wavelength of 1064 nm. Approximately 0.5 W of Nd:YVO4 laser power was used to irradiate the sample. The Raman spectra were measured with an indium gallium arsenide (InGaAs) detector. The samples were prepared for analysis by placing the sample into a capillary. A total of 256 sample scans were collected from 3600-100 cm$^{-1}$ at a spectral resolution of 4 cm$^{-1}$, using Happ-Genzel apodization. Wavelength calibration was performed using sulfur and cyclohexane.

X-Ray Powder Diffraction (XRPD): XRPD patterns were obtained using the two diffractometers discussed below.

Shimadzu XRD-6000 Diffractometer: Analyses were carried out on a Shimadzu XRD-6000 X-ray powder diffractometer using Cu Kα radiation. The instrument is equipped with a long fine focus X-ray tube. The tube voltage and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed to check the instrument alignment. Samples were prepared for analysis by placing them in an aluminum/silicon sample holder.

Inel XRG-3000 Diffractometer: Analyses were also performed on an Inel XRG-3000 diffractometer, equipped with a curved position-sensitive detector with a 2θ range of 120°. Real time data were collected using Cu Kα radiation starting at approximately 4° 2θ at a resolution of 0.03° 2θ. The tube voltage and amperage were set to 40 kV and 30 mA, respectively. Samples were run for 5 or 15 minutes. Patterns are displayed from 2.5 to 40° 2θ to facilitate direct pattern comparisons. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard.

XRPD Peak Picking Methods: Any XRPD files generated from an Inel instrument were converted to Shimadzu raw file using File Monkey version 3.0.4. The Shimadzu raw file was processed by the Shimadzu XRD-6000 version 4.1 software to automatically find peak positions. The "peak position" means the maximum intensity of a peaked intensity profile. Parameters used in peak selection are shown with each parameter set of the data. The following processes were used with the Shimadzu XRD-6000 "Basic Process" version 2.6 algorithm: 1) smoothing was done on all patterns; 2) the background was subtracted to find the net, relative intensity of the peaks; and 3) the Cu K alpha2 (1.5444 Å wavelength) peak was subtracted from the pattern at 50% of the Cu K alpha1 (1.5406 Å) peak intensity for all patterns. This method was used when selecting all peaks, except Form E. For Form E, peaks were selected using Match v 2.3.6 with default parameters.

Each figure listing XRPD peaks for each Form shows peaks selected by the peak picking method described above. Tables listing peaks for each Form shows peaks that are visually present in the diffractogram. Peaks which characteristically define the particular form are identified. I/Io is relative intensity.

Example 1

Preparation of Racemic Ilaprazole, Form A

3% NH$_4$OH/Acetonitrile (MeCN) (6.00 kg, 15.0 parts) was charged to a flask. After adjusting the temperature to 5° C. (2-8° C.), Ilaprazole (0.400 kg) was charged and the contents were agitated for 1 hour. The slurry was filtered off and the filter cake rinsed with 3% NH$_4$OH/MeCN (2×0.400 kg, 2×1.00 part).

The filter cake was charged into the flask, followed by 0.5% NH$_4$OH/EtOH (0.200 kg, 0.500 part) and concentrated at 20-25° C. under reduced pressure, until distillation stopped. 0.5% NH$_4$OH/EtOH (1.00 kg, 2.50 parts) was charged to the flask, followed by methylene chloride (2.40 kg, 6.00 parts). The resulting solution was concentrated at 20-25° C. under reduced pressure to ca. 1.0 L (2.50 volumes). 0.5% NH$_4$OH/EtOH (1.20 kg, 3.00 parts) was charged and the mixture was concentrated at maximum 20-25° C. under reduced pressure to ca. 1.2 L (3.00 volumes). 0.5% NH$_4$OH/EtOH (0.200 kg, 0.500 part) was charged and the contents were adjusted to 5° C. (2-8° C.) and agitated for 45 minutes. The slurry was filtered off and rinsed with 0.5% NH$_4$OH/EtOH (0.200 kg, 0.500 part), EtOH (0.200 kg, 0.500 part) and MTBE (2×0.200 kg, 2×0.500 part). The filter cake was pull-dried for 2 hours, and further dried under vacuum at maximum temperature of 53° C. for 92 hours. Yield of racemic ilaprazole, Form A: 0.338 kg (85%). Particle size: 206

Example 2

Preparation and Characterization of Racemic Ilaprazole Form A

A saturated solution of ilaprazole in acetone and triethylamine was filtered through a nylon filter into a glass vial. The open vial was then exposed to hexanes vapor within a closed chamber. The sample was allowed to equilbrate at ambient temperature and humidity. The crystals, recovered by decantation, were found to have a morphology of clustered needles and plates with birefringence and identified as racemic ilaprazole Form A.

Figure 5:
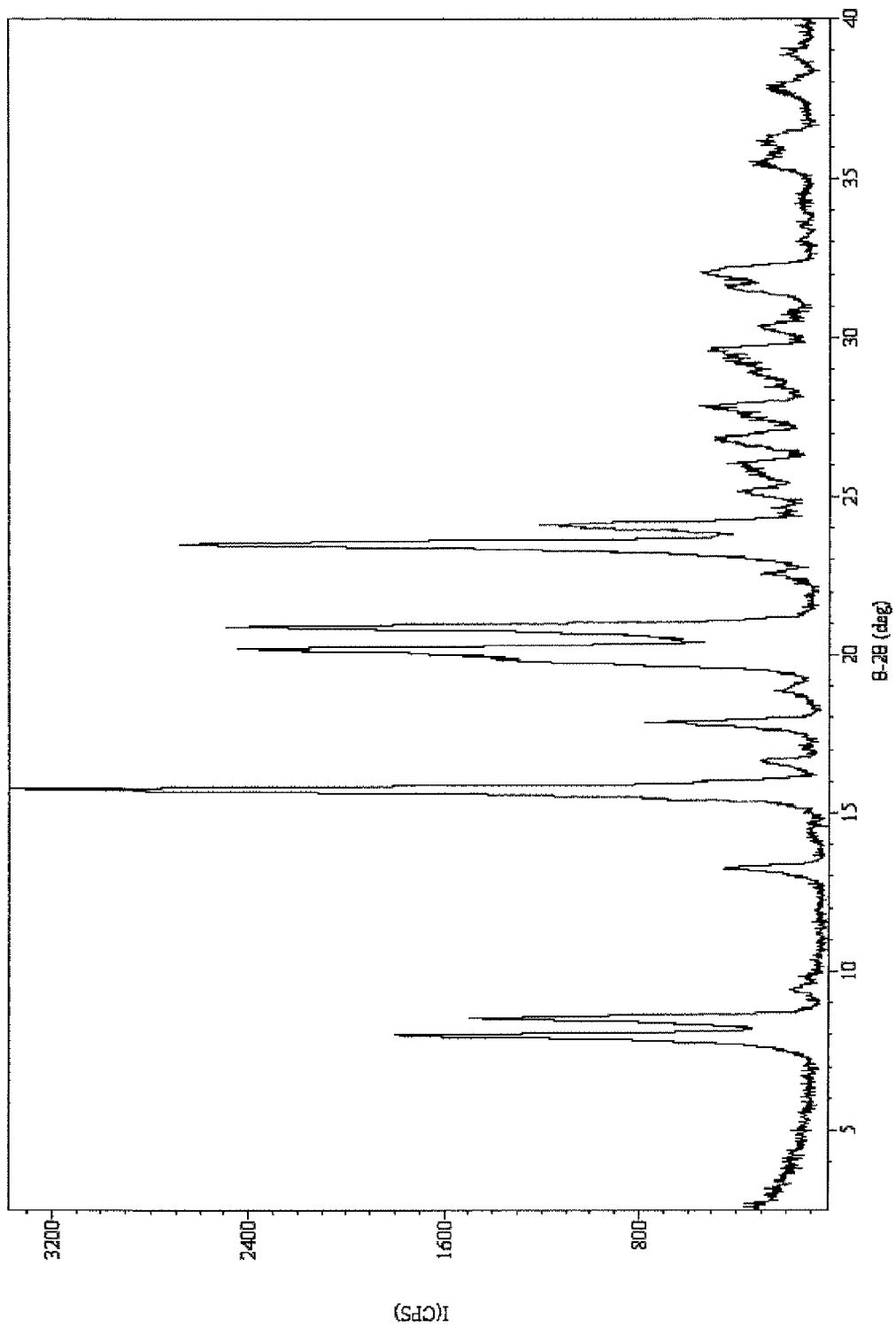
FIG. 5 is the XRPD pattern of racemic ilaprazole, Form A.

The XPD pattern of racemic ilaprazole Form A was obtained using a Shimadzu XRD-6000 X-ray powder diffractometer, as described above. The measurement conditions are reported in Table 3. FIG. 5 shows the XRPD pattern for racemic ilaprazole Form A. Table 4 reports the peaks identified in the XRPD pattern. In its XRPD racemic ilaprazole Form A may be characterized by peaks at 8.0° 2θ±0.2° 2θ; 13.2° 2θ±0.2° 2θ; and 24.1° 2θ±0.2° 2θ. Another characteristic grouping includes peaks at 8.0° 2θ±0.2° 2θ; 31.6° 2θ±0.2° 2θ; 32.0° 2θ±0.2° 2θ; 35.5° 2θ±0.2° 2θ; 36.1° 2θ±0.2° 2θ; 36.3° 2θ10.2° 2θ; 37.8° 2θ±0.2° 2θ; and 38.9° 2θ±0.2° 2θ.

TABLE 3

Measurement Conditions for XRPD Pattern of Racemic Ilaprazole Form A.

| Measurement Condition: | |
| --- | --- |
| X-ray tube | |
| target = | Cu |
| voltage = | 40.0 (kV) |
| current = | 40.0 (mA) |
| Slits | |
| divergence slit = | 1.00000 (deg) |
| scatter slit = | 1.00000 (deg) |
| receiving slit = | 0.15000 (mm) |
| Scanning | |
| drive axis = | 2Theta/Theta |
| scan range = | 2.500-40.000 |
| scan mode = | Continuous Scan |
| scan speed = | 3.0000 (deg/min) |
| sampling pitch = | 0.0200 (deg) |
| preset time = | 0.40 (sec) |
| Data Process Condition: | |
| Smoothing | [AUTO] |
| smoothing points = | 13 |
| B.G. Subtraction | [AUTO] |
| sampling points = | 13 |
| repeat times = | 30 |
| Ka1-a2 Separate | [MANUAL] |
| Ka1 a2 ratio = | 50.0 (%) |
| Peak Search | [AUTO] |
| differential points = | 13 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 3

Peak Positions of Ilaprazole Form A XRPD Pattern

| Peak No. | Position (°2θ ± 0.2 °2θ) | d-spacing | Intensity | I/I$_o$ |
| --- | --- | --- | --- | --- |
| 1 | 7.5 | 11.7 | 39 | 5 |
| 2 | 8.0 | 11.1 | 426 | 51 |
| 3 | 8.5 | 10.4 | 354 | 42 |
| 4 | 9.4 | 9.4 | 28 | 3 |
| 5 | 13.2 | 6.7 | 96 | 12 |
| 6 | 15.4 | 5.7 | 143 | 17 |
| 7 | 15.7 | 5.6 | 833 | 100 |
| 8 | 16.0 | 5.5 | 74 | 9 |
| 9 | 16.6 | 5.3 | 53 | 6 |
| 10 | 17.8 | 5.0 | 159 | 19 |
| 11 | 18.9 | 4.7 | 27 | 3 |
| 12 | 19.7 | 4.5 | 218 | 26 |
| 13 | 20.0 | 4.4 | 592 | 71 |
| 14 | 20.9 | 4.3 | 631 | 76 |
| 15 | 21.2 | 4.2 | 35 | 4 |
| 16 | 22.5 | 3.9 | 36 | 4 |
| 17 | 23.0 | 3.9 | 43 | 5 |
| 18 | 23.5 | 3.8 | 659 | 79 |
| 19 | 24.1 | 3.7 | 272 | 33 |
| 20 | 25.1 | 3.5 | 54 | 6 |
| 21 | 25.6 | 3.5 | 34 | 4 |
| 22 | 25.8 | 3.5 | 41 | 5 |
| 23 | 26.0 | 3.4 | 57 | 7 |
| 24 | 26.8 | 3.3 | 81 | 10 |
| 25 | 27.4 | 3.3 | 35 | 4 |
| 26 | 27.7 | 3.2 | 89 | 11 |
| 27 | 28.9 | 3.1 | 48 | 6 |
| 28 | 29.2 | 3.1 | 62 | 7 |
| 29 | 29.6 | 3.0 | 93 | 11 |
| 30 | 30.3 | 2.9 | 42 | 5 |
| 31 | 31.6 | 2.8 | 81 | 10 |
| 32 | 32.0 | 2.8 | 115 | 14 |
| 33 | 35.5 | 2.5 | 52 | 6 |
| 34 | 35.8 | 2.5 | 35 | 4 |
| 35 | 36.1 | 2.5 | 49 | 6 |
| 36 | 36.3 | 2.5 | 46 | 6 |
| 37 | 37.8 | 2.4 | 44 | 5 |
| 38 | 38.9 | 2.3 | 30 | 4 |

Figure 6:
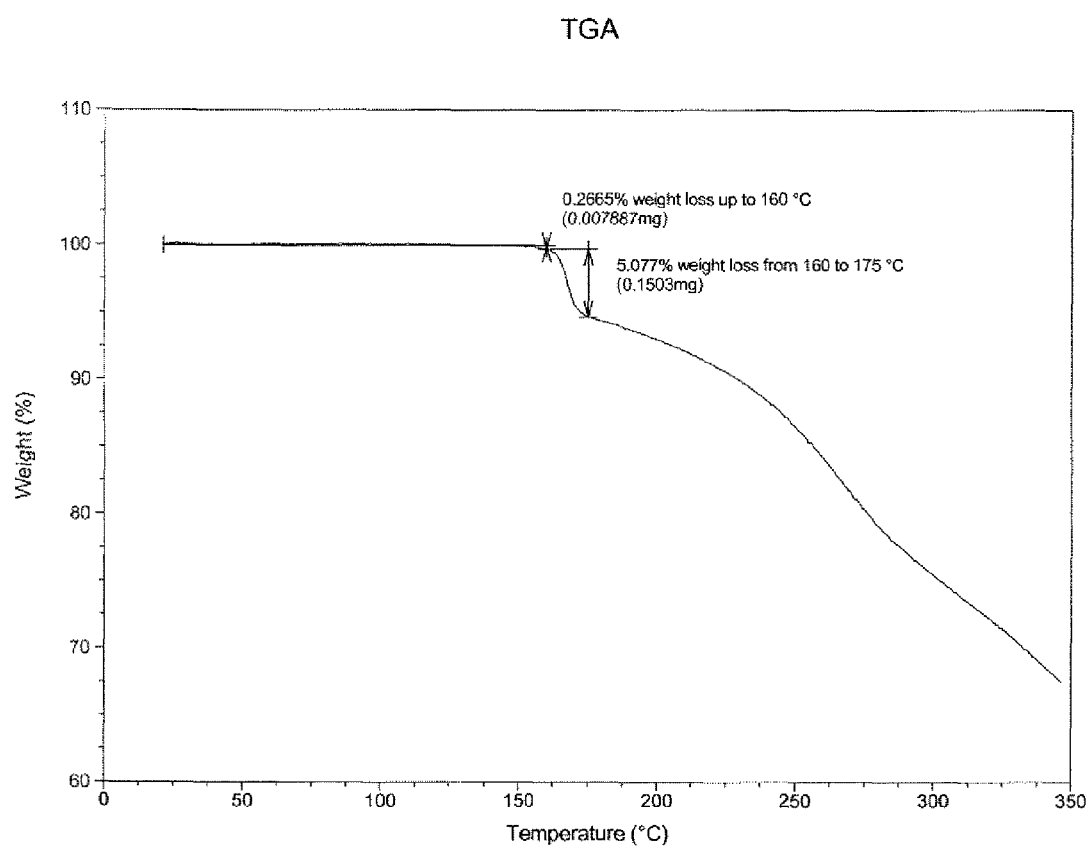
FIG. 6 is the TGA thermogram of racemic ilaprazole, Form A.

FIG. 6 is the TGA thermogram of racemic ilaprazole, Form A. The sample showed 0.3% weight loss up to 160° C.

Figure 7:
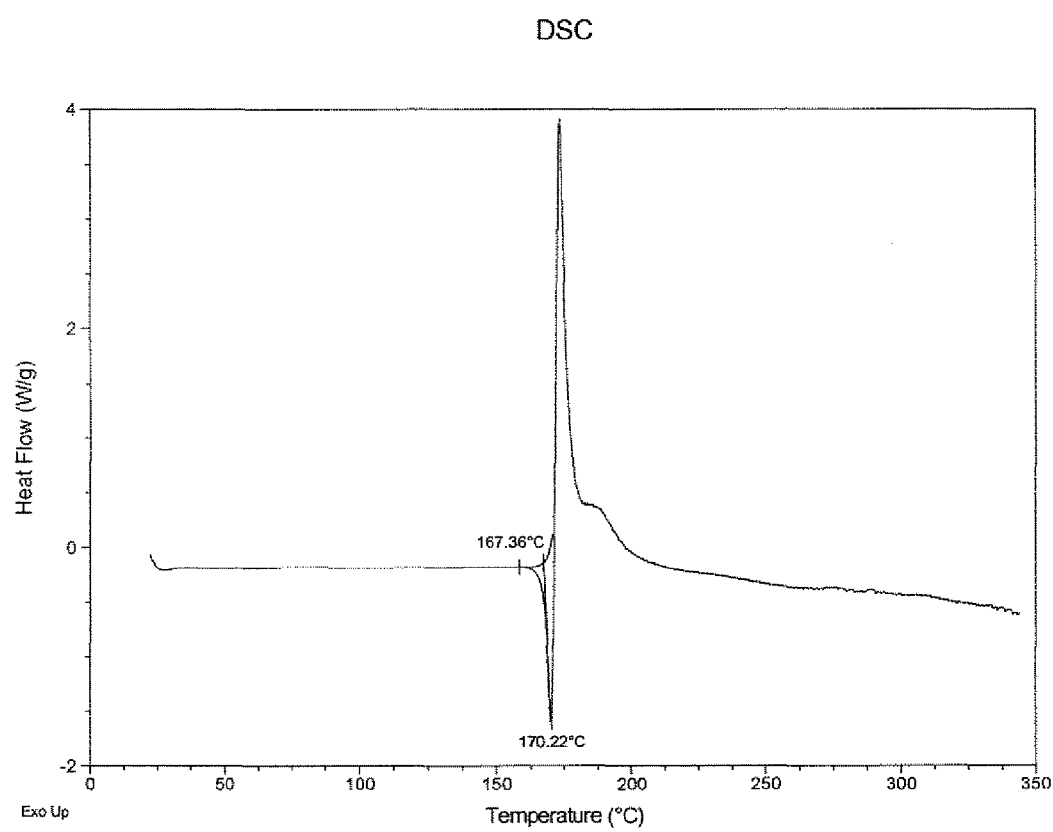
FIG. 7 is the DSC thermogram of racemic ilaprazole, Form A.

FIG. 7 is the DSC thermogram of racemic ilaprazole, Form A. The endotherm onset was at 167° C. (max 170° C.).

Figure 8:
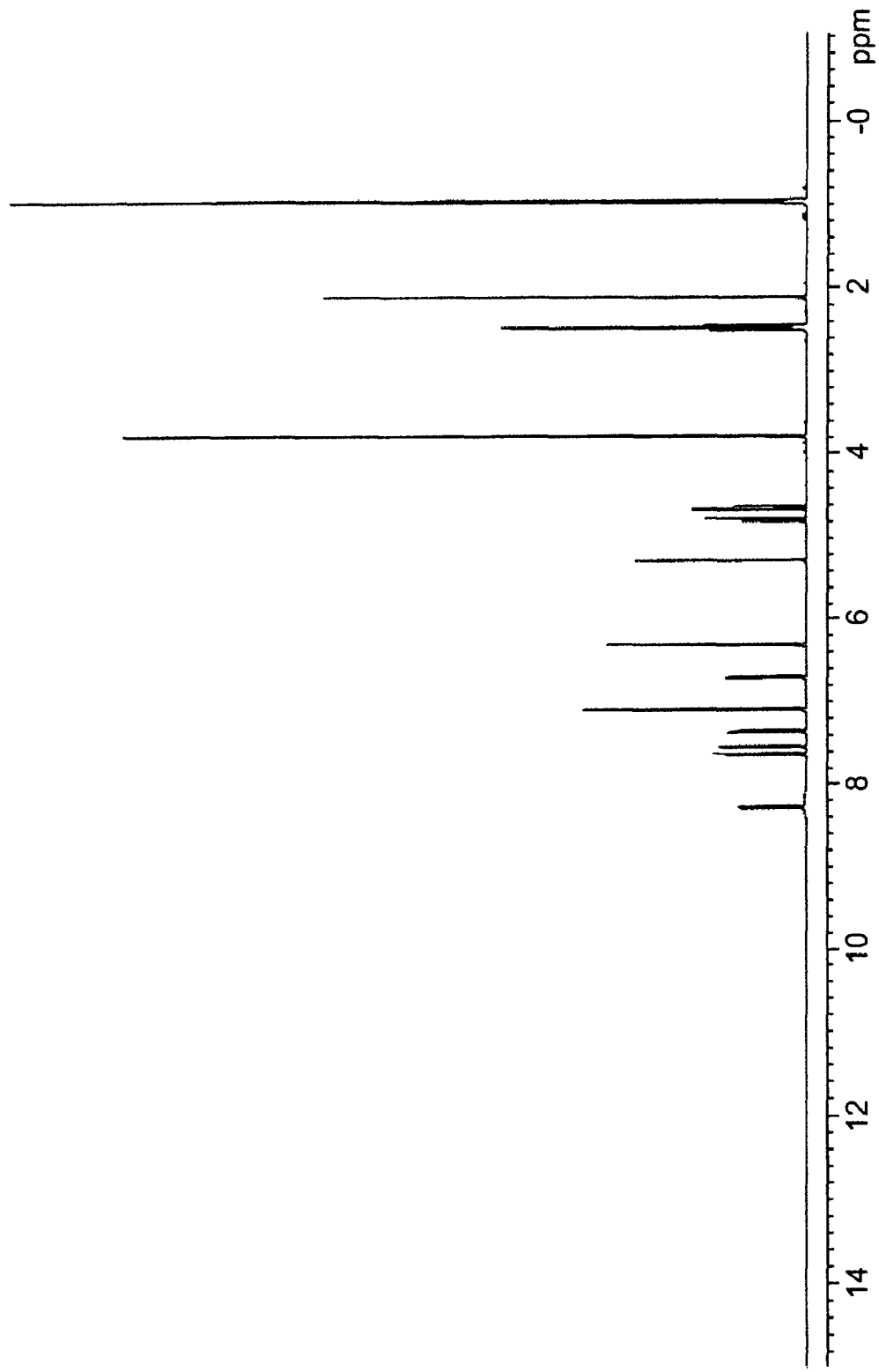
FIG. 8 is the proton NMR spectrum of racemic ilaprazole, Form A.

FIG. 8 is the proton NMR Spectrum of racemic ilaprazole, Form A. Peaks near 5.32 are due to solvent—not to ilaprazole. Peaks near 1.0 and 2.5 are due to triethylamine (TEA), which is used to stabilize ilaprazole in solution, and not to ilaprazole.

Figure 9:
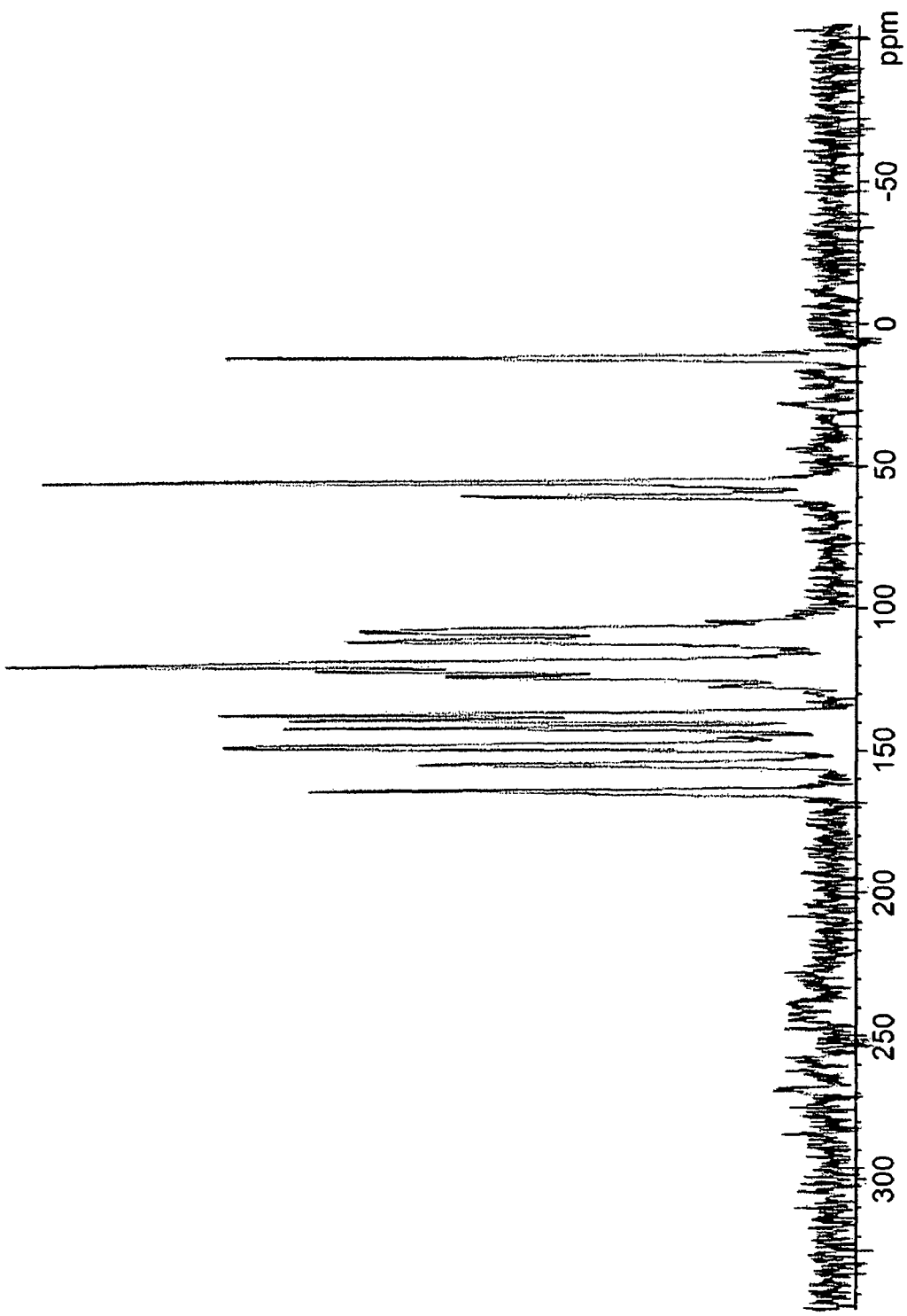
FIG. 9 is the solid state $^{13}$C CP/MAS ssNMR spectrum of racemic ilaprazole, Form A.

FIG. 9 is the solid state $^{13}$C CP/MAS NMR spectrum of racemic ilaprazole, Form A. The spectrum is externally referenced against glycine at 176.5 ppm. The peaks in the solid state $^{13}$C NMR spectrum are reported in Table 5. A minor amount of Form F was observed in the solid state $^{13}$C NMR spectrum. The peaks associated with Form F are not reported in Table 5, although the peak at 148.4 ppm is coincident between the forms.

TABLE 5

Solid State $^{13}$C NMR Peaks for Racemic Ilaprazole, Form A.

| PPM | HEIGHT |
| --- | --- |
| 163.9 | 89.8 |
| 154.6 | 71.1 |
| 148.4 | 104.2 |
| 141.8 | 94.2 |
| 139.1 | 92.8 |
| 137.2 | 105.2 |
| 123.9 | 66.1 |

TABLE 5-continued

Solid State $^{13}$C NMR Peaks for Racemic Ilaprazole, Form A.

| PPM | HEIGHT |
|---|---|
| 122.1 | 88.6 |
| 120.1 | 141.8 |
| 111.6 | 83.2 |
| 108.2 | 80.9 |
| 61.0 | 63.8 |
| 56.1 | 135.6 |
| 12.6 | 104.2 |

Figure 10:
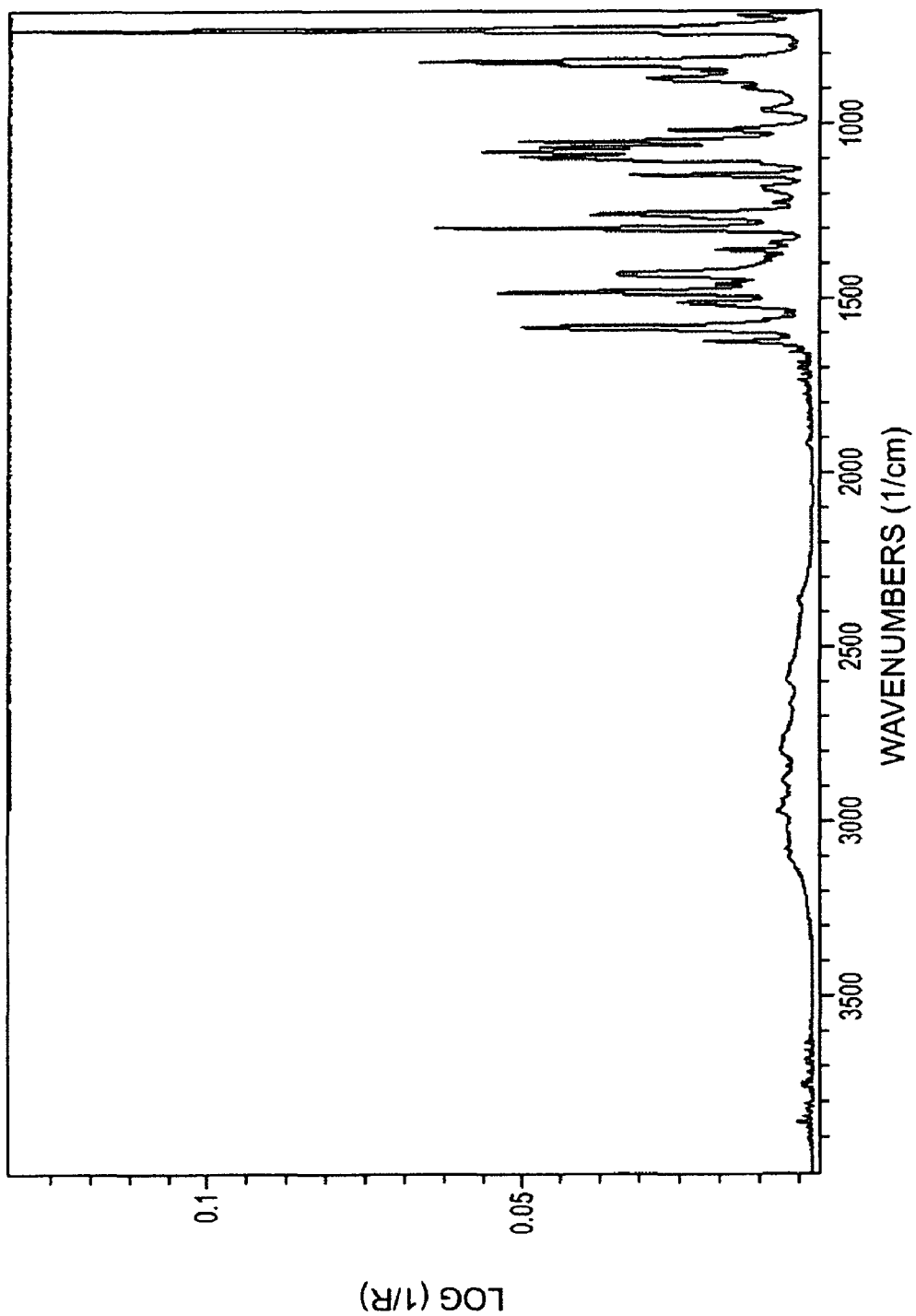
FIG. 10 is the IR spectrum of racemic ilaprazole, Form A.

FIG. 10 is the IR spectrum of racemic ilaprazole, Form A. Table 6 reports the absorbance peaks in the IR spectrum.

TABLE 6

Peaks in IR Spectrum of Racemic Ilaprazole, Form A

| | Position: | | Intensity: |
|---|---|---|---|
| Position: | 689.7 | Intensity: | 0.0164 |
| Position: | 730.9 | Intensity: | 0.131 |
| Position: | 775.0 | Intensity: | 0.0079 |
| Position: | 822.1 | Intensity: | 0.0673 |
| Position: | 832.5 | Intensity: | 0.0444 |
| Position: | 849.1 | Intensity: | 0.0220 |
| Position: | 869.5 | Intensity: | 0.0303 |
| Position: | 895.0 | Intensity: | 0.0155 |
| Position: | 961.0 | Intensity: | 0.0124 |
| Position: | 1018.5 | Intensity: | 0.0269 |
| Position: | 1050.7 | Intensity: | 0.0507 |
| Position: | 1067.0 | Intensity: | 0.0475 |
| Position: | 1079.2 | Intensity: | 0.0572 |
| Position: | 1096.6 | Intensity: | 0.0507 |
| Position: | 1116.4 | Intensity: | 0.0125 |
| Position: | 1147.6 | Intensity: | 0.0330 |
| Position: | 1178.7 | Intensity: | 0.0124 |
| Position: | 1186.6 | Intensity: | 0.0121 |
| Position: | 1222.2 | Intensity: | 0.0104 |
| Position: | 1255.1 | Intensity: | 0.0392 |
| Position: | 1296.0 | Intensity: | 0.0642 |
| Position: | 1337.9 | Intensity: | 0.0111 |
| Position: | 1358.2 | Intensity: | 0.0196 |
| Position: | 1378.5 | Intensity: | 0.0118 |
| Position: | 1386.5 | Intensity: | 0.0117 |
| Position: | 1428.4 | Intensity: | 0.0350 |
| Position: | 1457.1 | Intensity: | 0.0198 |
| Position: | 1480.7 | Intensity: | 0.0543 |
| Position: | 1510.6 | Intensity: | 0.0257 |
| Position: | 1539.9 | Intensity: | 0.0085 |
| Position: | 1559.4 | Intensity: | 0.0119 |
| Position: | 1581.7 | Intensity: | 0.0501 |
| Position: | 1623.0 | Intensity: | 0.0215 |
| Position: | 1652.8 | Intensity: | 0.0077 |
| Position: | 1684.2 | Intensity: | 0.0064 |
| Position: | 1733.8 | Intensity: | 0.0063 |
| Position: | 2360.9 | Intensity: | 0.0063 |
| Position: | 2586.3 | Intensity: | 0.0081 |
| Position: | 2791.8 | Intensity: | 0.0091 |
| Position: | 2838.4 | Intensity: | 0.0081 |
| Position: | 2879.0 | Intensity: | 0.0088 |
| Position: | 2935.3 | Intensity: | 0.0091 |
| Position: | 2966.2 | Intensity: | 0.0097 |
| Position: | 3074.6 | Intensity: | 0.0083 |
| Position: | 3098.3 | Intensity: | 0.0079 |
| Position: | 3853.2 | Intensity: | 0.0067 |

Figure 11:
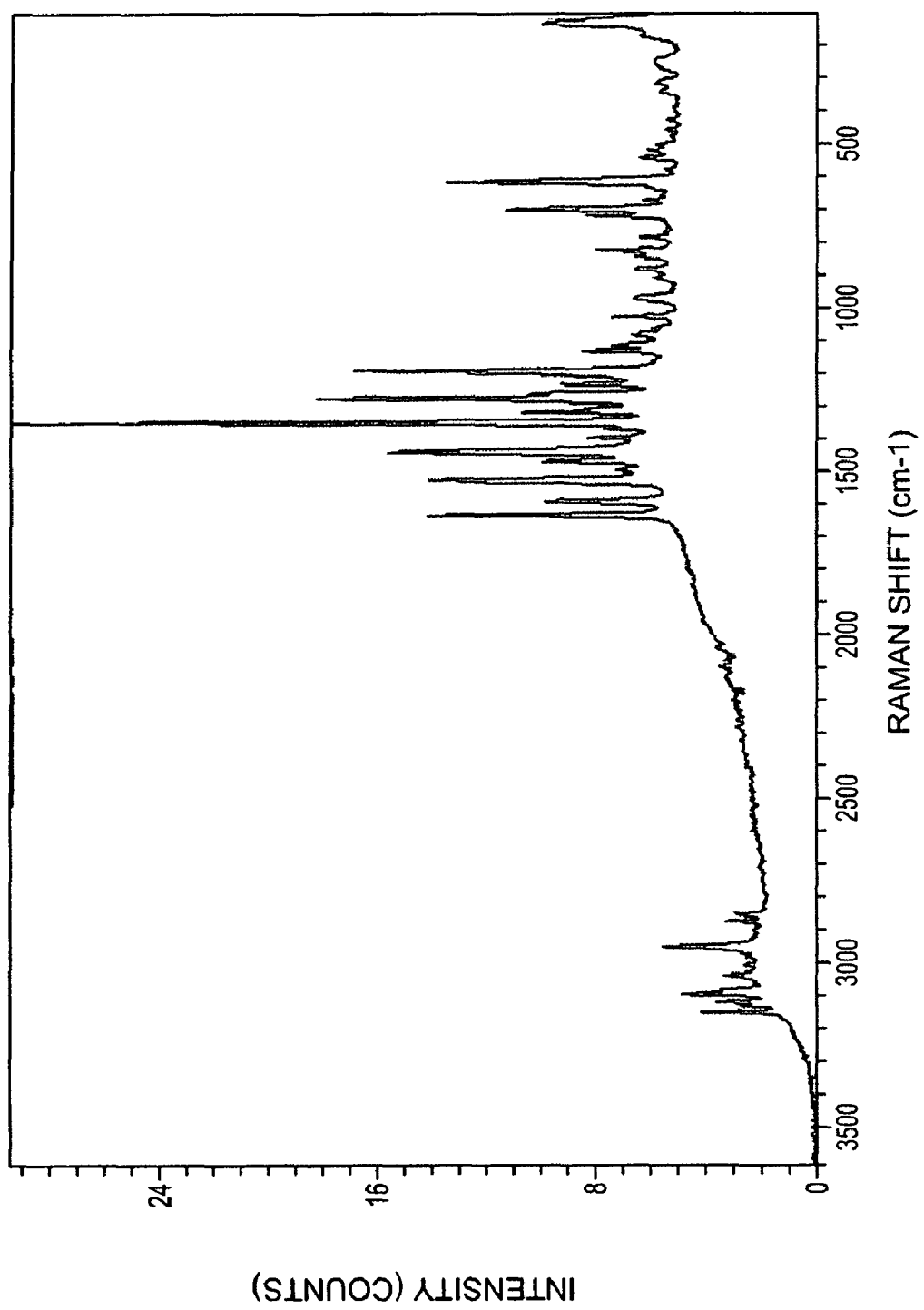
FIG. 11 is the RAMAN spectrum of racemic ilaprazole, Form A.

FIG. 11 is the RAMAN spectrum of racemic ilaprazole, Form A. Table 7 reports the absorbance peaks in the Raman spectrum.

TABLE 7

Peaks in the Raman Spectrum of Racemic Ilaprazole, Form A.

| | Position: | | Intensity: |
|---|---|---|---|
| Position: | 419.0 | Intensity: | 0.382 |
| Position: | 448.1 | Intensity: | 0.489 |
| Position: | 468.3 | Intensity: | 0.274 |
| Position: | 495.9 | Intensity: | 0.861 |
| Position: | 513.6 | Intensity: | 1.139 |
| Position: | 537.3 | Intensity: | 1.416 |
| Position: | 570.9 | Intensity: | 0.499 |
| Position: | 609.0 | Intensity: | 8.471 |
| Position: | 626.0 | Intensity: | 1.247 |
| Position: | 647.6 | Intensity: | 0.750 |
| Position: | 665.0 | Intensity: | 1.347 |
| Position: | 693.7 | Intensity: | 6.328 |
| Position: | 713.2 | Intensity: | 3.418 |
| Position: | 733.4 | Intensity: | 0.611 |
| Position: | 749.8 | Intensity: | 0.518 |
| Position: | 762.0 | Intensity: | 0.587 |
| Position: | 776.3 | Intensity: | 1.559 |
| Position: | 815.9 | Intensity: | 3.102 |
| Position: | 836.1 | Intensity: | 1.731 |
| Position: | 876.5 | Intensity: | 1.778 |
| Position: | 900.1 | Intensity: | 1.031 |
| Position: | 938.8 | Intensity: | 0.483 |
| Position: | 962.8 | Intensity: | 1.847 |
| Position: | 1019.7 | Intensity: | 2.473 |
| Position: | 1056.0 | Intensity: | 0.873 |
| Position: | 1076.7 | Intensity: | 1.525 |
| Position: | 1104.2 | Intensity: | 2.107 |
| Position: | 1119.9 | Intensity: | 3.057 |
| Position: | 1149.1 | Intensity: | 0.500 |
| Position: | 1179.9 | Intensity: | 11.380 |
| Position: | 1222.7 | Intensity: | 3.826 |
| Position: | 1251.2 | Intensity: | 4.911 |
| Position: | 1266.1 | Intensity: | 12.991 |
| Position: | 1296.3 | Intensity: | 3.051 |
| Position: | 1306.7 | Intensity: | 5.460 |
| Position: | 1337.8 | Intensity: | 24.178 |
| Position: | 1358.5 | Intensity: | 2.454 |
| Position: | 1386.7 | Intensity: | 3.014 |
| Position: | 1429.9 | Intensity: | 10.411 |
| Position: | 1457.9 | Intensity: | 4.703 |
| Position: | 1483.8 | Intensity: | 2.072 |
| Position: | 1512.5 | Intensity: | 8.978 |
| Position: | 1583.4 | Intensity: | 4.749 |
| Position: | 1623.7 | Intensity: | 9.033 |
| Position: | 2839.0 | Intensity: | 1.219 |
| Position: | 2859.6 | Intensity: | 1.659 |
| Position: | 2883.9 | Intensity: | 0.722 |
| Position: | 2935.4 | Intensity: | 4.143 |
| Position: | 2966.2 | Intensity: | 1.164 |
| Position: | 2992.6 | Intensity: | 1.344 |
| Position: | 3021.9 | Intensity: | 2.174 |
| Position: | 3063.9 | Intensity: | 2.400 |
| Position: | 3075.3 | Intensity: | 3.810 |
| Position: | 3098.6 | Intensity: | 2.686 |
| Position: | 3110.2 | Intensity: | 1.922 |
| Position: | 3130.6 | Intensity: | 3.377 |

Figure 12:
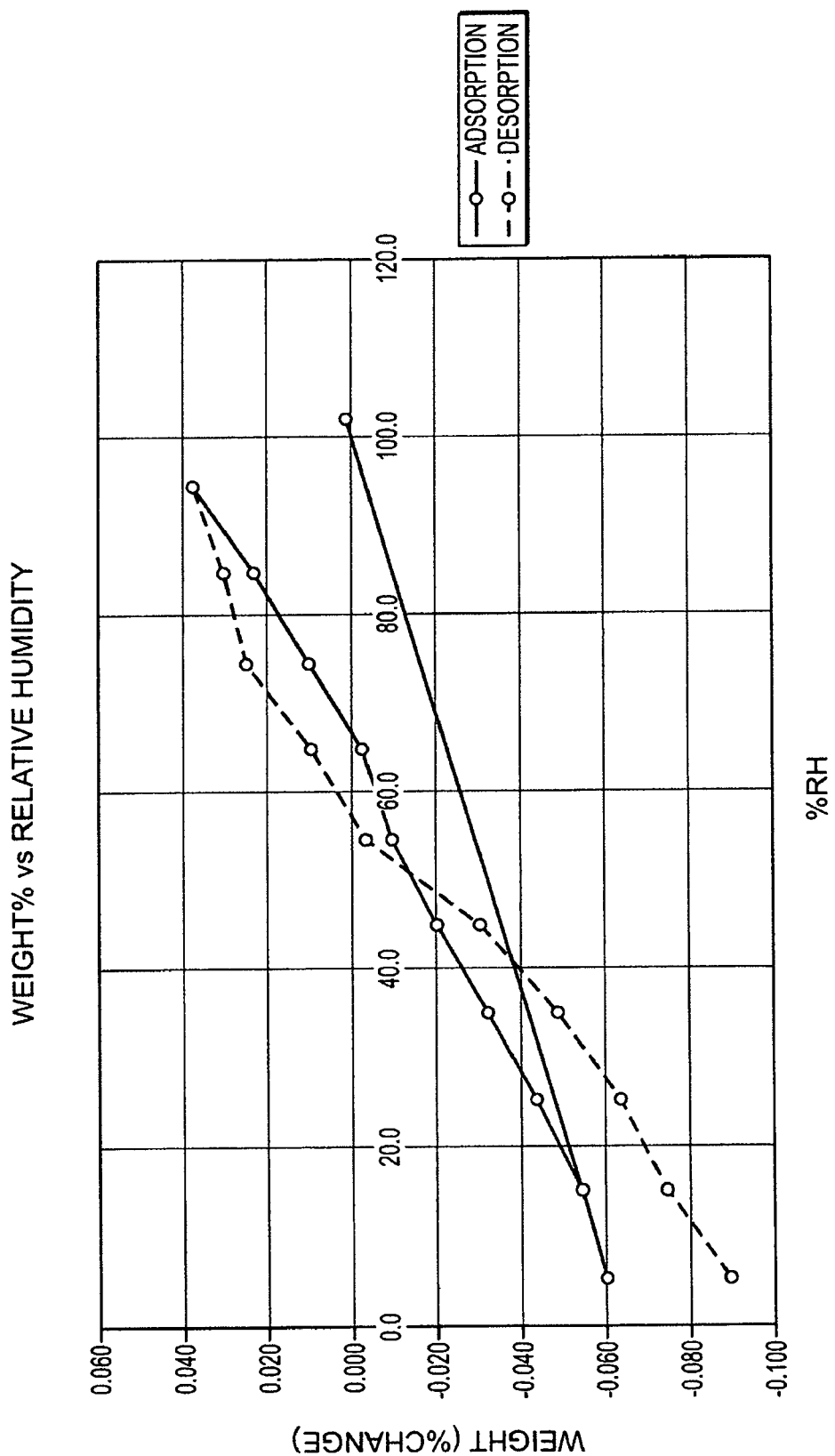
FIG. 12 is the DVS isotherm of racemic ilaprazole, Form A.

FIG. 12 is the DVS isotherm of racemic ilaprazole, Form A. The DVS isotherm shows a 0.06% weight loss at 5% RH, a 0.10% weight gain from 5 to 95% RH and a 0.13% weight loss from 95 to 5% RH.

A single crystal X-ray diffraction study of the structure of racemic ilaprazole, Form A was done. The data was collected using colorless plate of racemic ilaprazole, Form A having approximate dimensions of 0.44×0.35×0.13 mm, which was mounted on a glass fiber in random orientation. Preliminary examination and data collection were performed with Mo K$_\alpha$ radiation (λ=0.71073 Å) on a Nonius KappaCCD diffractometer. Refinements were performed on an LINUX PC using SHIELX97. Sheldrick, G. M. *SHELX97, A Program for Crystal Structure Refinement*, University of Gottingen, Germany, 1997. The crystallographic drawings were obtained using the programs ORTEP (Johnson, C. K. ORTEPIII, Report ORNL-6895, Oak Ridge National Laboratory, Tenn., U.S.A. 1996; OPTEP-3 for Windows V1.05, Farrugia, L. J., *J. Appl. Cryst.*

1997, 30, 565); CAMERON (Watkin, D. J.; Prout, C. K.; Pearce, L. J. CAMERON, Chemical Crystallography Laboratory, University of Oxford, Oxford, 1996), and Mercury (Bruno, I. J. Cole, J. C. Edgington, P. R. Kessler, M. K. Macrae, C. F. McCabe, P. Pearson, J. and Taylor, R. *Acta Crystallogr.*, 2002 B58, 389).

Cell constants and an orientation matrix for data collection were obtained from least-squares refinement using the setting angles of 8027 reflections in the range 2°<θ<27°. The refined mosaicity from DENZO/SCALEPACK (Otwinowski, Z.; Minor, W. *Methods Enzymol.* 1997, 276, 307) is 0.54° indicating moderate crystal quality. The space group was determined by the program XPREP. Bruker, XPREP in SHELXTL v. 6.12., Bruker AXS Inc., Madison, Wis., USE, 2002. From the systematic presence of the following conditions: 0k0 k=2n, and from subsequent least-squares refinement, the space group was determined to be $P2_1$ (no. 4). The data were collected to a maximum 2θ value of 54.9°, at a temperature of 150±1 K.

The data reduction was done as follows; Frames were integrated with DENZO-SMN. Otwinoski et al., supra. A total of 8027 reflections were collected, of which 3676 were unique. Lorentz and polarization corrections were applied to the data. The linear absorption coefficient was 2.0 cm$^{-1}$ for Mo K$_\alpha$ radiation. An empirical absorption correction using SCALEPACK (Otwinoski et al., supra) was applied. Transmission coefficients ranged from 0.94 to 0.98. Intensities of equivalent reflections were averaged. The agreement factor for the averaging was 4.3% based on intensity.

The structure was solved by direct methods using SIR2004. Burla, M. C., Caliandro, R., Carnalli, M., Carrozzini, B., Cascarano, G. L., De Caro, L., Giacovazzo, C., Polidori, G., and Spagna, R., *J. Appl. Cryst.* 2005, 38, 381. The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

The weight w is defined as $1/[\sigma^2(F_o^2)+(0.0507P)^2+(0.0000P)]$, where $P=(F_o^2+2F_c^2)/3$.

Scattering factors were taken from the "International Tables for Crystallography." International Tables for Crystallography, Vol. C, Kluwer Academic Publishers: Dordrecht, The Netherlands, 1992, Tables 4.2.6.8 and 6.1.1.4. Of the 3676 reflections used in the refinements, only the reflections with $F_o^2 > 2\sigma(F_o^2)$ were used in calculating R. A total of 2844 reflections were used in the calculation. The final cycle of refinement included 252 variable parameters and converged (largest parameter shift was approximately equal to its estimated standard deviation) with unweighted and weighted agreement factors of:

$$R = \sum |F_o - F_c| \Big/ \sum F_o = 0.041$$

$$R_w = \sqrt{\left(\sum w(F_o^2 - F_c^2)^2 \Big/ \sum w(F_o^2)^2\right)} = 0.091$$

The standard deviation of an observation of unit weight was 1.014. The highest peak in the final difference Fourier had a height of 0.22 e/Å$^3$. The minimum negative peak had a height of −0.30 e/Å$^3$. The factor for the determination of the absolute structure (Flack, H. D. *Acta Cryst.* 1983, A39, 876) refined to −0.04(8).

A calculated XRPD pattern was generated for Cu radiation using Mercury 1.3 and the atomic coordinates, space group, and unit cell parameters from the single crystal data.

A summary of the crystal data and crystallographic data collection parameters for racemic ilaprazole Form A are provided in Table 8. The monoclinic cell parameters and calculated volume are: a=10.8006(9) Å, b=7.3333(3) Å, c=11.5247(10) Å, α=90.0°, β=107.261(4)°, γ=90.00°, V=871.69(11) Å$^3$. The formula weight of ilaprazole Form A is 366.44 g/mol, with Z=2 and a calculated density of 1.396 g cm$^{-3}$. The space group was determined to be $P2_1$. The quality of the structure obtained is high, as indicated by the R-value of 0.041 (4.1%). Usually R-values in the range of 0.02 to 0.06 are quoted for the most reliably determined structures.

TABLE 8

Single Crystal Data and Data Collection Parameters for Racemic Ilaprazole, Form A.

| | |
|---|---|
| formula | $C_{19}H_{18}N_4O_2S$ |
| formula weight | 366.44 |
| space group | $P2_1$ (No. 4) |
| a, Å | 10.8006(9) |
| b, Å | 7.3333(3) |
| c, Å | 11.5247(10) |
| b, deg | 107.261(4) |
| V, Å$^3$ | 871.69(11) |
| Z | 2 |
| $d_{calc}$, g cm$^{-3}$ | 1.396 |
| crystal dimensions, mm | 0.44 × 0.35 × 0.13 |
| temperature, K | 150 |
| radiation (wavelength, Å) | Mo K$_\alpha$ (0.71073) |
| monochromator | graphite |
| linear abs coef, mm$^{-1}$ | 0.198 |
| absorption correction applied | empirical[a] |
| transmission factors: min, max | 0.94, 0.98 |
| diffractometer | Nonius KappaCCD |
| h, k, l range | −13 to 14 −8 to 8 −14 to 14 |
| 2θ range, deg | 4.54-54.94 |
| mosaicity, deg | 0.54 |
| programs used | SHELXTL |
| $F_{000}$ | 384.0 |
| weighting | |
| $1/[\sigma^2(F_o^2) + (0.0507P)^2 + 0.0000P]$ where $P = (F_o^2 + 2F_c^2)/3$ | |
| data collected | 8027 |
| unique data | 3676 |
| $R_{int}$ | 0.043 |
| data used in refinement | 3676 |
| cutoff used in R-factor calculations | $F_o^2 > 2.0\sigma(F_o^2)$ |
| data with I > 2.0σ(I) | 2844 |
| refined extinction coef | 0.0300 |
| number of variables | 252 |
| largest shift/esd in final cycle | 0.01 |
| $R(F_o)$ | 0.041 |
| $R_w(F_o^2)$ | 0.091 |
| goodness of fit | 1.014 |
| absolute structure determination | Flack parameter[b] (−0.04(8)) |

[a] Otwinowski Z. & Minor, W. Methods Enzymol., 1997, 276, 307.
[b] Flack, H. D. Acta Cryst., 1983 A39, 876.

Figure 13:
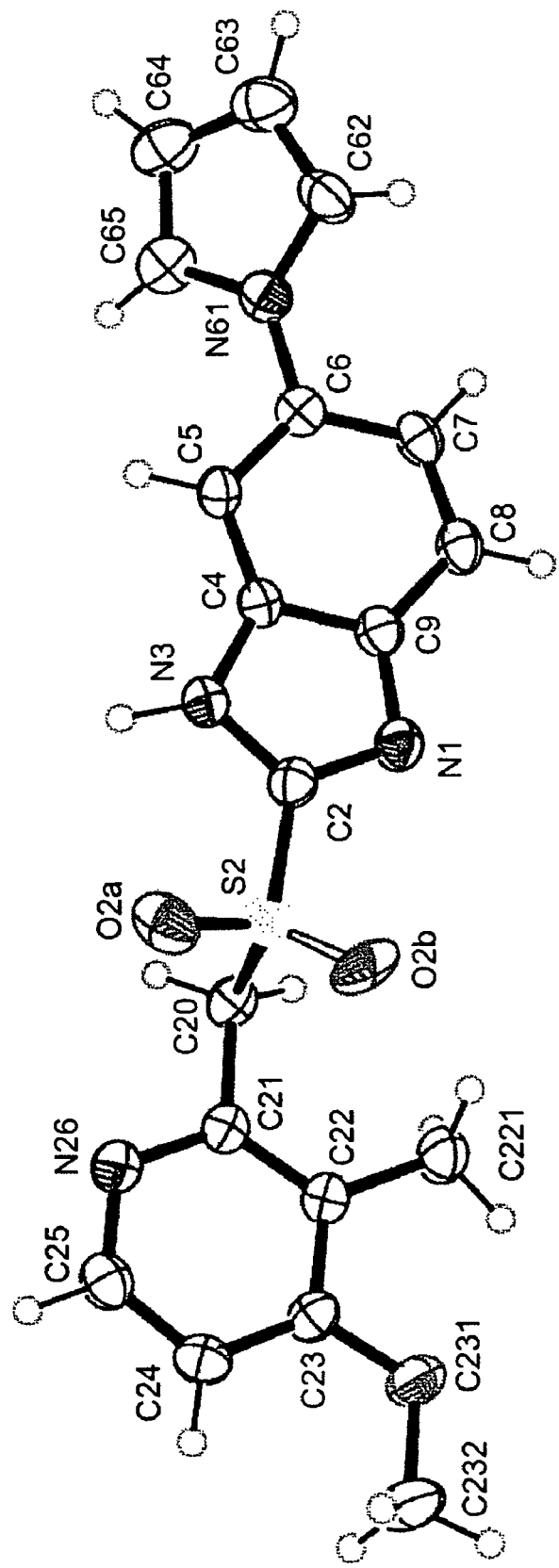
FIG. 13 is an ORTEP drawing of racemic ilaprazole Form A. Atoms are represented by 50% probability anisotropic thermal ellipsoids

An ORTEP drawing of racemic ilaprazole form A is shown in FIG. 13. Atoms are represented by 50% probability anisotropic thermal ellipsoids. Note that the appearance of the second oxygen affixed to the sulfinyl group is a representation of the disorder most likely caused by the presence of both enantiomers in the unit cell. The occupancy of the enantiomers was refined to approximately a 75:25 ratio. The major enantiomer is represented with a solid bond between S2 and O2a and the minor enantiomer with a hollow bond between S2 and O2b, respectively. The material appears to be a member of a rare class of racemic compounds where the stoichiometry of the two enantiomers is not a 1:1 ratio. This class of compounds is sometimes referred to "anomalous" racemates. The asymmetric unit shown in FIG. 14 contains a single ilaprazole molecule exhibiting a packing arrangement where every fourth molecule is the minor enantiomer.

Figure 14:
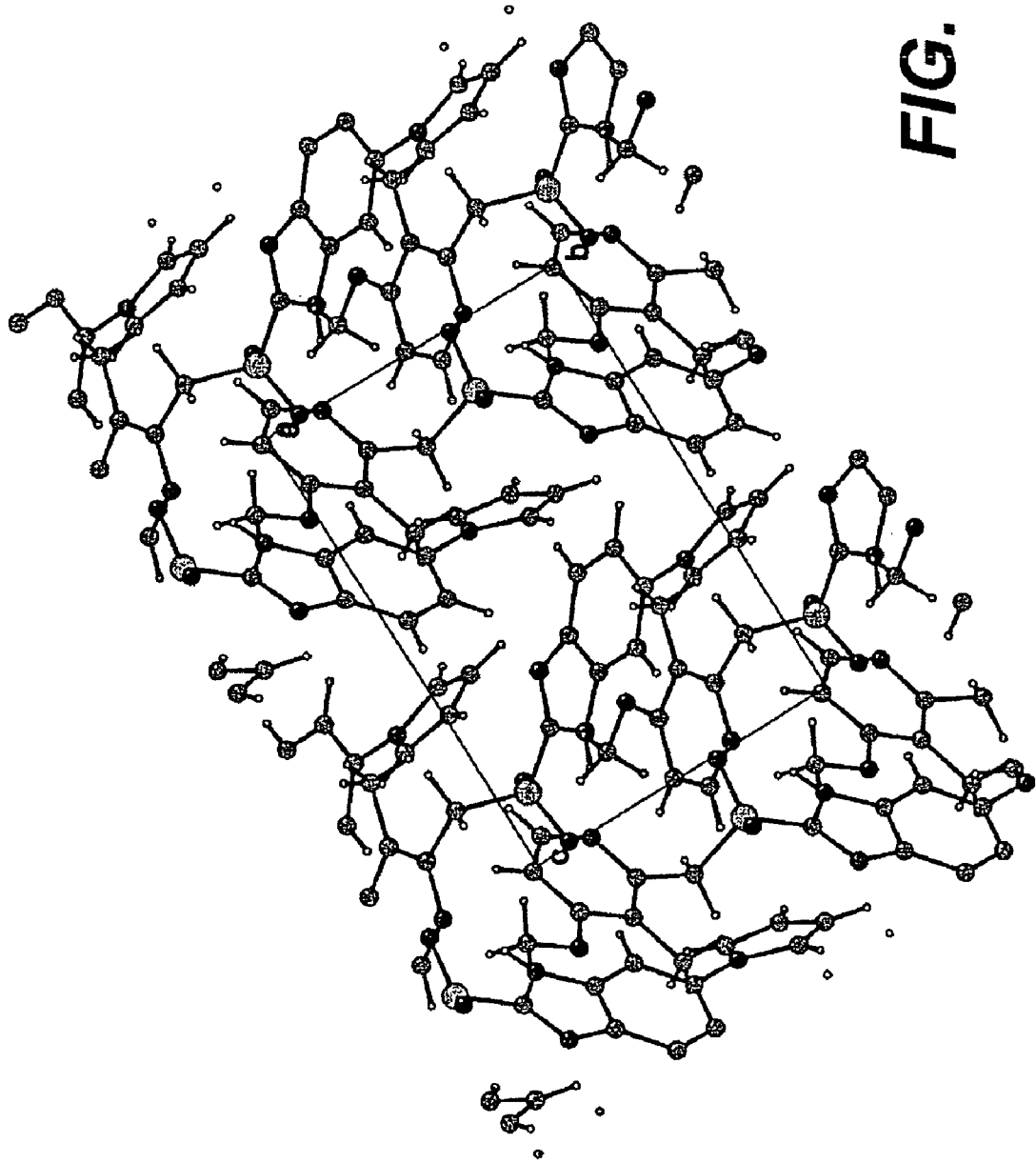
FIG. 14 is the packing diagram of racemic ilaprazole Form A viewed down the crystallographic a axis.
Figure 15:
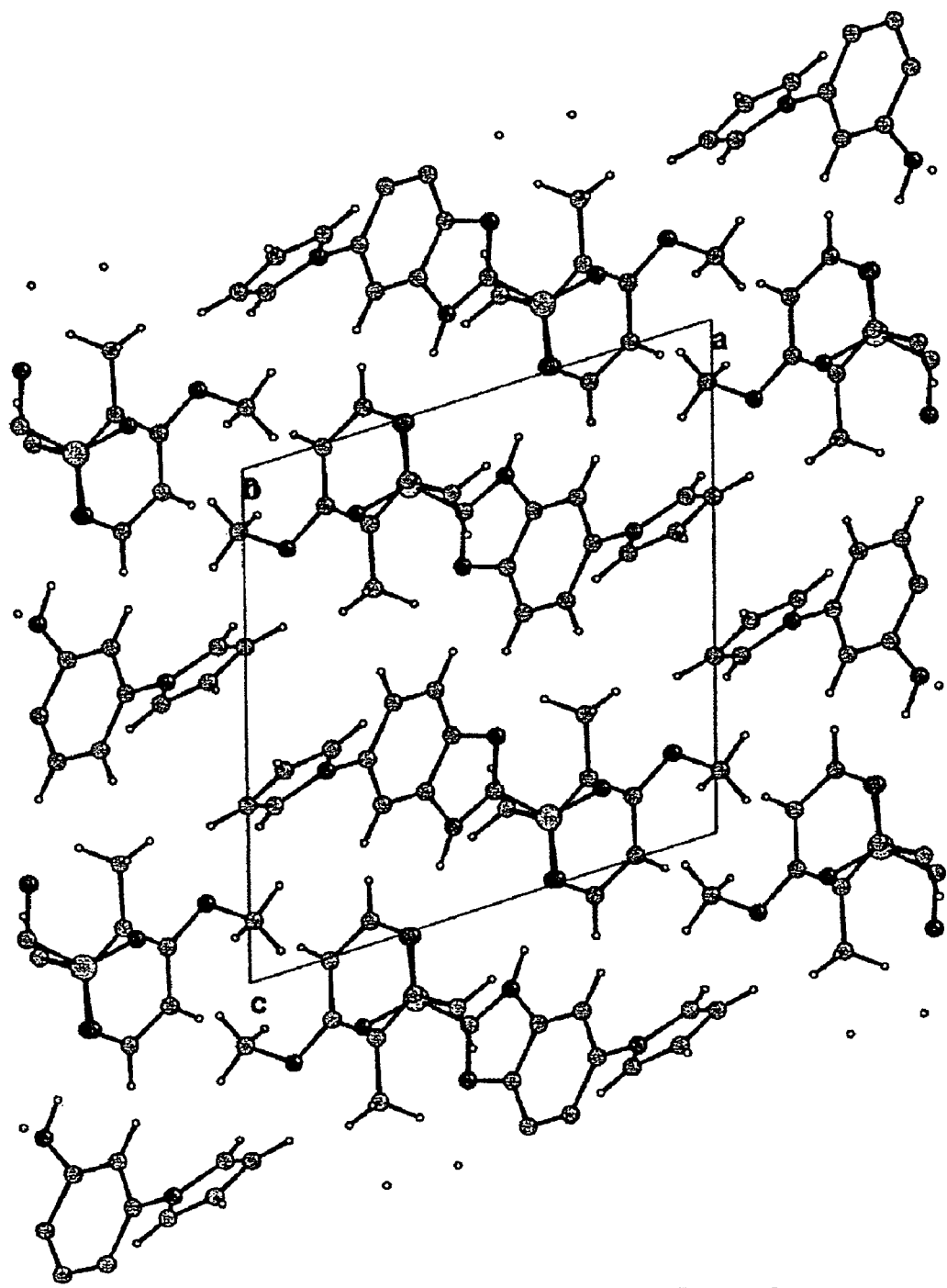
FIG. 15 is the packing diagram of racemic ilaprazole Form A viewed down the crystallographic b axis.
Figure 16:
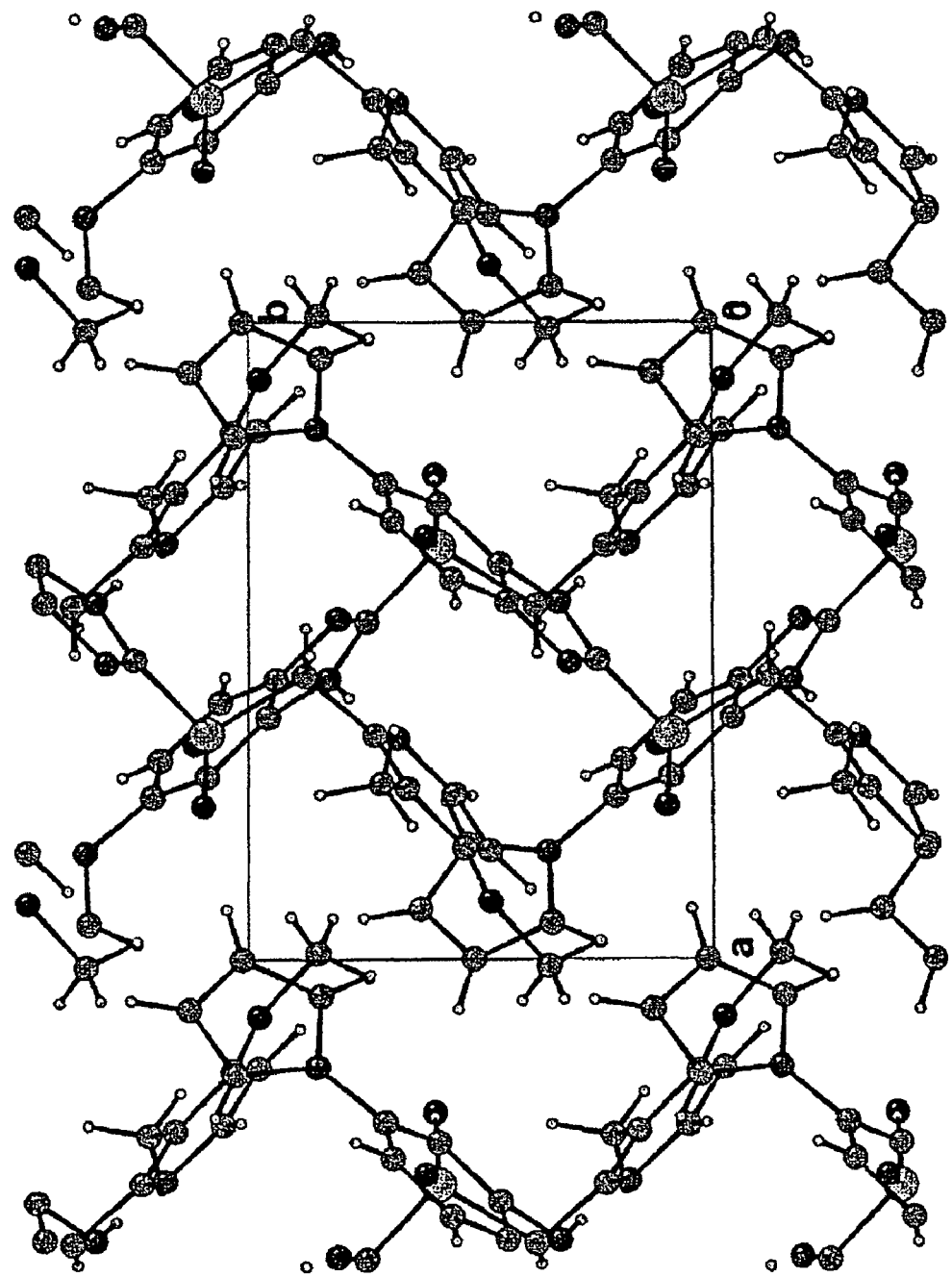
FIG. 16 is the packing diagram of racemic ilaprazole Form A viewed down the crystallographic c axis.

Packing diagrams viewed along the a, b, and c crystallographic axes are shown in FIGS. 14-16 respectively. The packing arrangement in the Form A crystal structure can be described as sheets of ilaprazole molecules running perpendicular to the crystallographic b axis (FIG. 15). The calculated density of the Form A crystal structure (1.396 g cm$^{-3}$) is slightly higher that the Form F crystal structure (1.391 g cm$^{-3}$), suggesting Form A would be the more stable form at 150 K.

Hydrogen bonds are observed between the secondary amine (N3) of the benzimidazole ring of one ilaprazole molecule to the pyridine nitrogen (N26) of an adjacent ilaprazole molecule. This hydrogen-bonding network forms sheets of ilaprazole molecules that are rotated approximately 90° from each other, resulting in a one-dimensional hydrogen bonding network. Closer examination of the structure reveals two close contacts between the two oxygen sites of the sulfinyl group. There is a close contact of approximately 3.4 Å between the oxygen atom of the major enantiomer (O2a) and the nitrogen atom secondary amine (N3) of the benzimidazole group. This is not a hydrogen bonding interaction because the hydrogen atom in not in a position to interact with the sulfinyl oxygen. The second close contact of approximately 3.3 Å between the oxygen atom of the minor enantiomer (O2b) and the ether linkage might actually be a slightly repulsive interaction due to the lone pairs. No other potential interactions were observed in the crystal structure.

Figure 17:
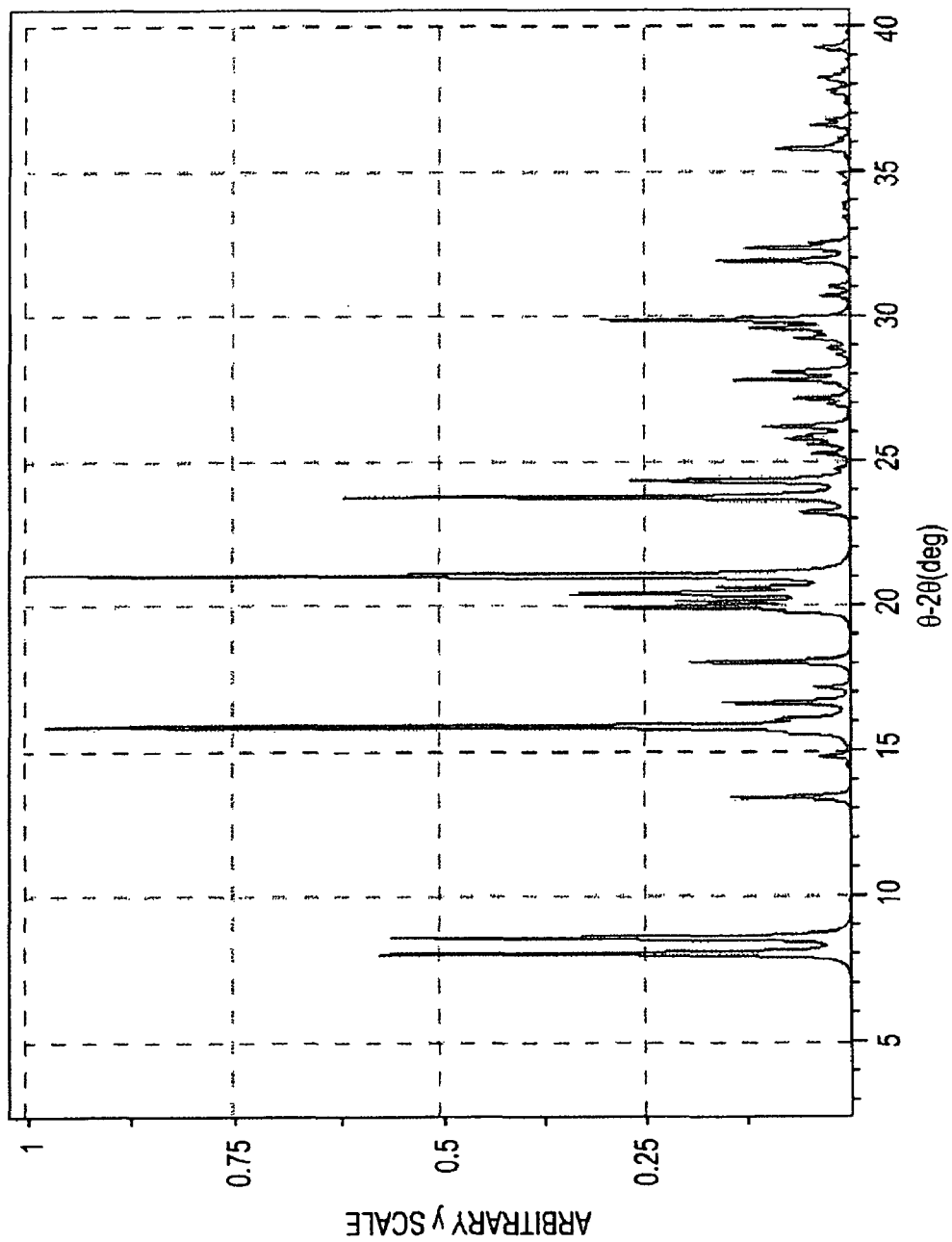
FIG. 17 is the calculated X-ray powder pattern of racemic ilaprazole Form A based on the single crystal X-ray data.
Figure 18:
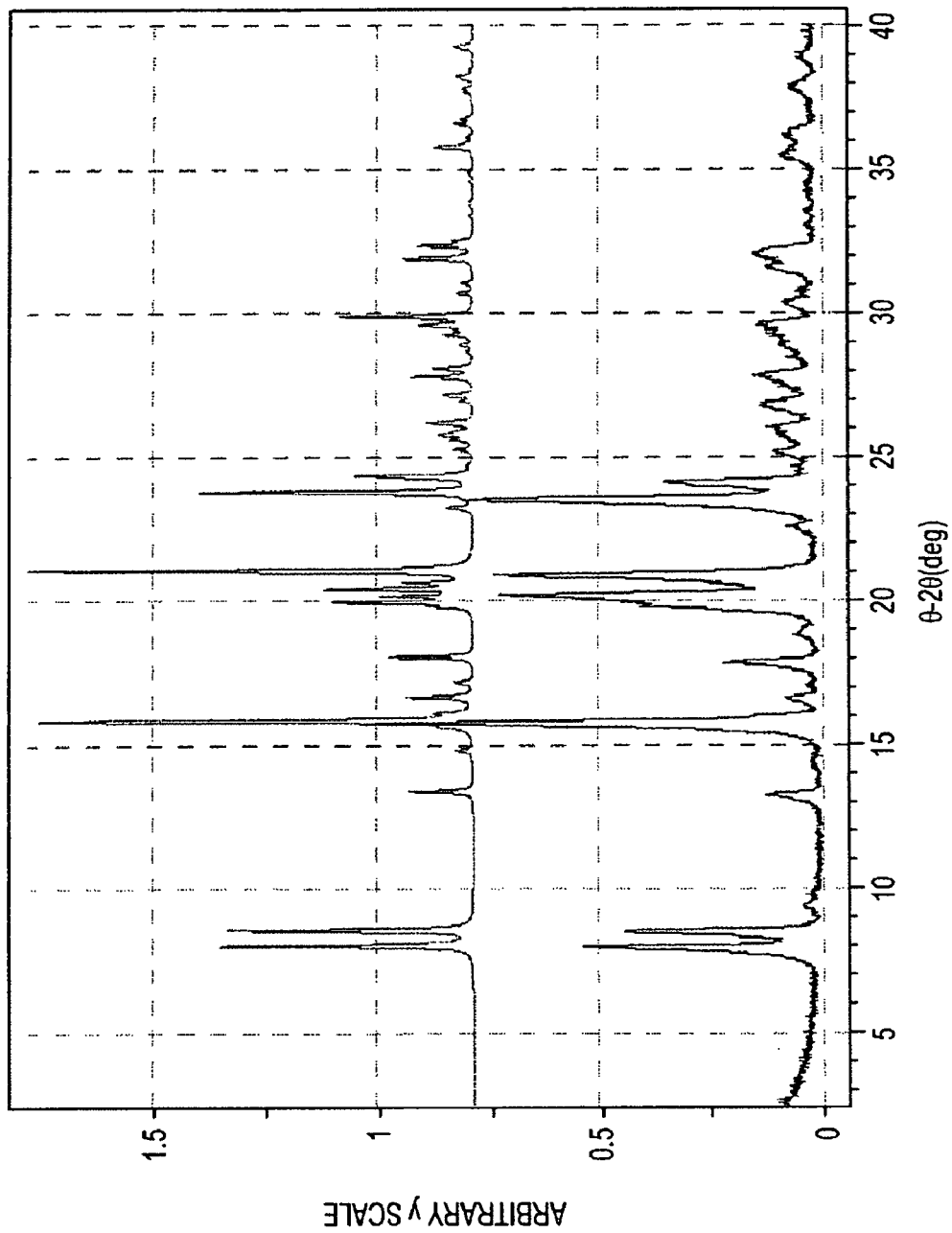
FIG. 18 is a comparison of the calculated XRPD pattern of racemic ilaprazole Form A to the experimental XRPD of racemic ilaprazole Form A.

FIG. 17 shows a calculated XRPD pattern of ilaprazole, generated from the single crystal data. The experimental XRPD pattern of ilaprazole Form A is shown in FIG. 5. FIG. 18 shows a comparison of the calculated XRPD pattern to the experimental pattern of racemic ilaprazole Form A. All peaks in the experimental patterns are represented in the calculated XRPD pattern, indicating the bulk material is likely a single phase. The slight shifts in peak location are likely due to the fact that the experimental powder pattern was collected at ambient temperature, and the single crystal data was collected at 150 K. Low temperatures are used in single crystal analysis to improve the quality of the structure.

If the material was a single enantiomer, the absolute configuration of the molecule would be determined by analysis of anomalous X-ray scattering by the crystal. The differences in intensities of the anomalous scattering are then compared with calculated scattering intensities for each enantiomer. These measured and calculated intensities can then be fit to a parameter, the Flack factor. Because each crystal contains a mixture of enantiomers and therefore is not enantiopure, the absolute configuration of the model in FIG. 13 cannot be uniquely determined with the current data set.

Example 3

Preparation and Characterization of Racemic Ilaprazole, Form F

Approximately 153.4 mg racemic ilaprazole Form A was added to a solution containing 3 mL dichloromethane (DCM) and 10 μL triethylamine (TEA). The solid was dissolved using sonication. The solution was filtered through a 0.2 micron nylon filter into a glass vial and left to evaporate at ambient room temperature. A lightly colored solid resulted approximately 1 day later, which was identified as Form F.

Racemic ilaprazole, Form F was also prepared by the following procedure. Racemic ilaprazole (0.5 g, Form A) was slurried in EtOH/10% water (5 mL, 10 volumes) and was stirred at 0° C. for 24 h. The resulting solids were isolated by filtration and dried under vacuum at 40° C. to afford 0.44 g of Form K; 87.8% recovery. Racemic ilaprazole (40 mg, Form K) was then slurried in anhydrous EtOH (2 mL, 50 vol) and stirred at temperatures ranging from 5 to 20° C. for 24 h. The obtained solids were isolated by filtration and dried under vacuum at 40° C. to afford Form F. A slurry temperature of 6° C. is preferred.

Figure 19:
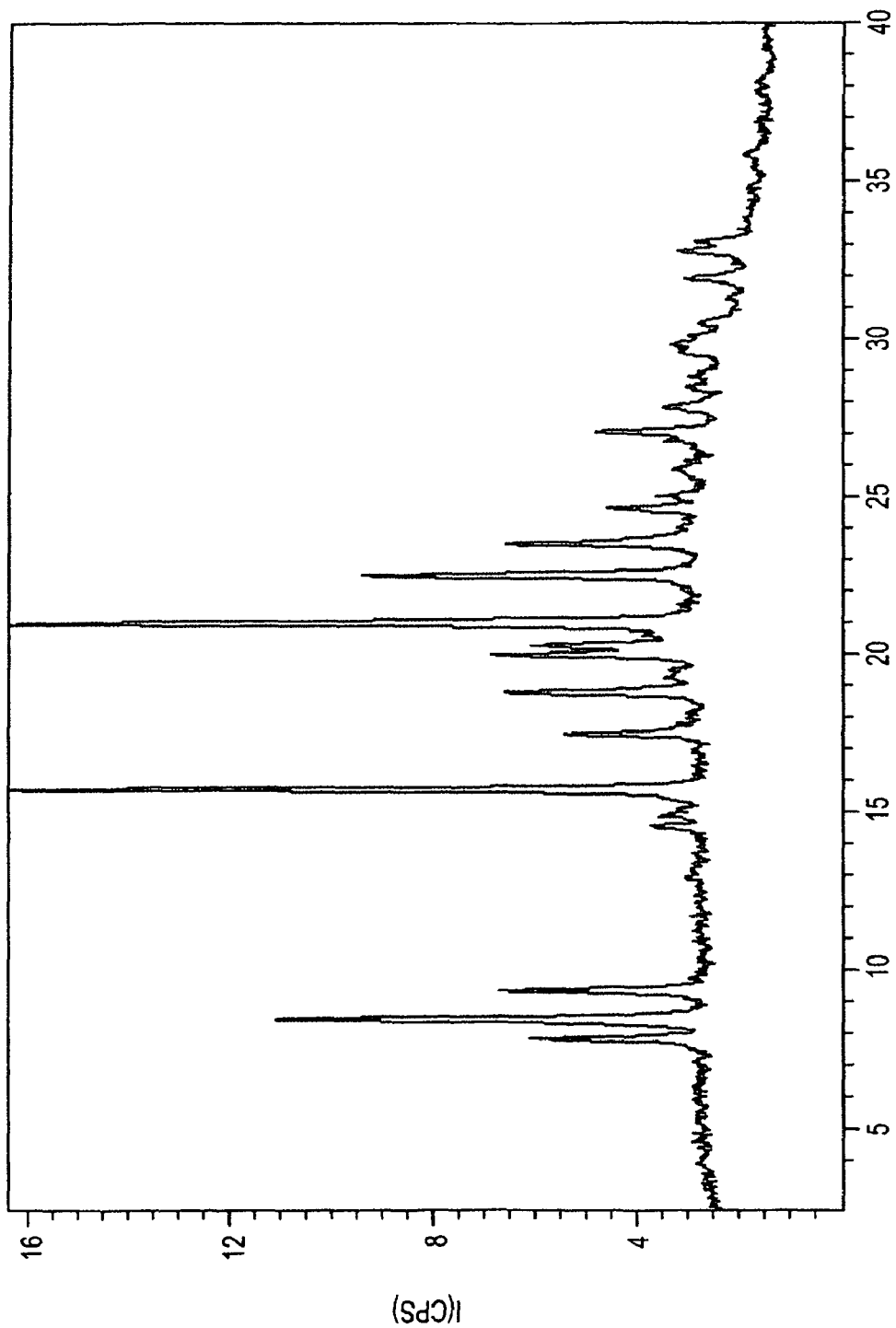
FIG. 19 is the XRPD pattern of racemic ilaprazole, Form F.

The XRPD pattern of racemic ilaprazole, Form F was obtained using an Inel XRG-3000 diffractometer, as described above. The measurement conditions are reported in Table 9. FIG. 19 shows the XRPD pattern for racemic ilaprazole, Form F. Table 10 reports the peaks identified in the XRPD pattern. In its XRPD racemic ilaprazole, Form F may be characterized by peaks at 9.4° 2θ±0.2° 2θ; 17.5° 2θ+0.2° 2θ; 18.8° 2θ+0.2° 2θ and 32.8° 2θ±0.2° 2θ. Another characteristic grouping includes peaks at 7.9° 2θ±0.2° 2θ; 28.8° 2θ±0.2° 2θ; 30.5° 2θ±0.2° 2θ; 31.9° 2θ+0.2° 2θ and 35.8° 2θ±0.2° 2θ.

TABLE 9

Measurement Conditions for XRPD Pattern of Racemic Ilaprazole, Form F

| Measurement Condition: | |
|---|---|
| X-ray tube | |
| target = | Cu |
| voltage = | 40.0 (kV) |
| current = | 30.0 (mA) |
| Slits | |
| divergence slit = | 1.00000 (deg) |
| scatter slit = | 1.00000 (deg) |
| receiving slit = | 0.15000 (mm) |
| Scanning | |
| drive axis = | 2Theta/Theta |
| scan range = | 2.507-39.987 |
| scan mode = | Continuous Scan |
| scan speed = | 0.0040 (deg/min) |
| sampling pitch = | 0.0200 (deg) |
| preset time = | 300.00 (sec) |
| Data Process Condition: | |
| Smoothing | [AUTO] |
| smoothing points = | 11 |
| B.G. Subtraction | [AUTO] |
| sampling points = | 13 |
| repeat times = | 30 |
| Kα1-α2 Separate | [MANUAL] |
| Kα1 α2 ratio = | 50.0 (%) |
| Peak Search | [AUTO] |
| differential points = | 11 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 10

Peak Positions of Racemic Ilaprazole, Form F XRPD Pattern

| Peak No. | Position (°2θ ± 0.2 °2θ) | d-spacing | Intensity | I/I₀ |
|---|---|---|---|---|
| 1 | 7.9 | 11.2 | 614 | 22 |
| 2 | 8.5 | 10.4 | 1619 | 59 |
| 3 | 9.4 | 9.4 | 784 | 29 |
| 4 | 14.6 | 6.1 | 184 | 7 |
| 5 | 14.9 | 5.9 | 142 | 5 |
| 6 | 15.1 | 5.8 | 90 | 3 |
| 7 | 15.4 | 5.7 | 135 | 5 |
| 8 | 15.8 | 5.6 | 2600 | 95 |
| 9 | 17.5 | 5.1 | 505 | 18 |
| 10 | 18.8 | 4.7 | 752 | 27 |
| 11 | 19.2 | 4.6 | 114 | 4 |
| 12 | 19.5 | 4.5 | 89 | 3 |
| 13 | 20.0 | 4.4 | 757 | 28 |
| 14 | 20.3 | 4.4 | 616 | 22 |
| 15 | 20.6 | 4.3 | 166 | 6 |
| 16 | 21.0 | 4.2 | 2742 | 100 |
| 17 | 22.5 | 3.9 | 1327 | 48 |
| 18 | 23.5 | 3.8 | 763 | 28 |
| 19 | 23.7 | 3.7 | 242 | 9 |
| 20 | 24.6 | 3.6 | 339 | 12 |
| 21 | 25.0 | 3.6 | 124 | 5 |
| 22 | 25.9 | 3.4 | 102 | 4 |
| 23 | 26.8 | 3.3 | 170 | 6 |
| 24 | 27.1 | 3.3 | 465 | 17 |
| 25 | 27.8 | 3.2 | 196 | 7 |
| 26 | 28.5 | 3.1 | 118 | 4 |
| 27 | 28.8 | 3.1 | 114 | 4 |
| 28 | 29.5 | 3.0 | 184 | 7 |
| 29 | 29.8 | 3.0 | 212 | 8 |
| 30 | 30.1 | 3.0 | 157 | 6 |
| 31 | 30.5 | 2.9 | 135 | 5 |
| 32 | 31.9 | 2.8 | 229 | 8 |
| 33 | 32.8 | 2.7 | 278 | 10 |
| 34 | 33.1 | 2.7 | 198 | 7 |
| 35 | 35.8 | 2.5 | 85 | 3 |

Figure 20:
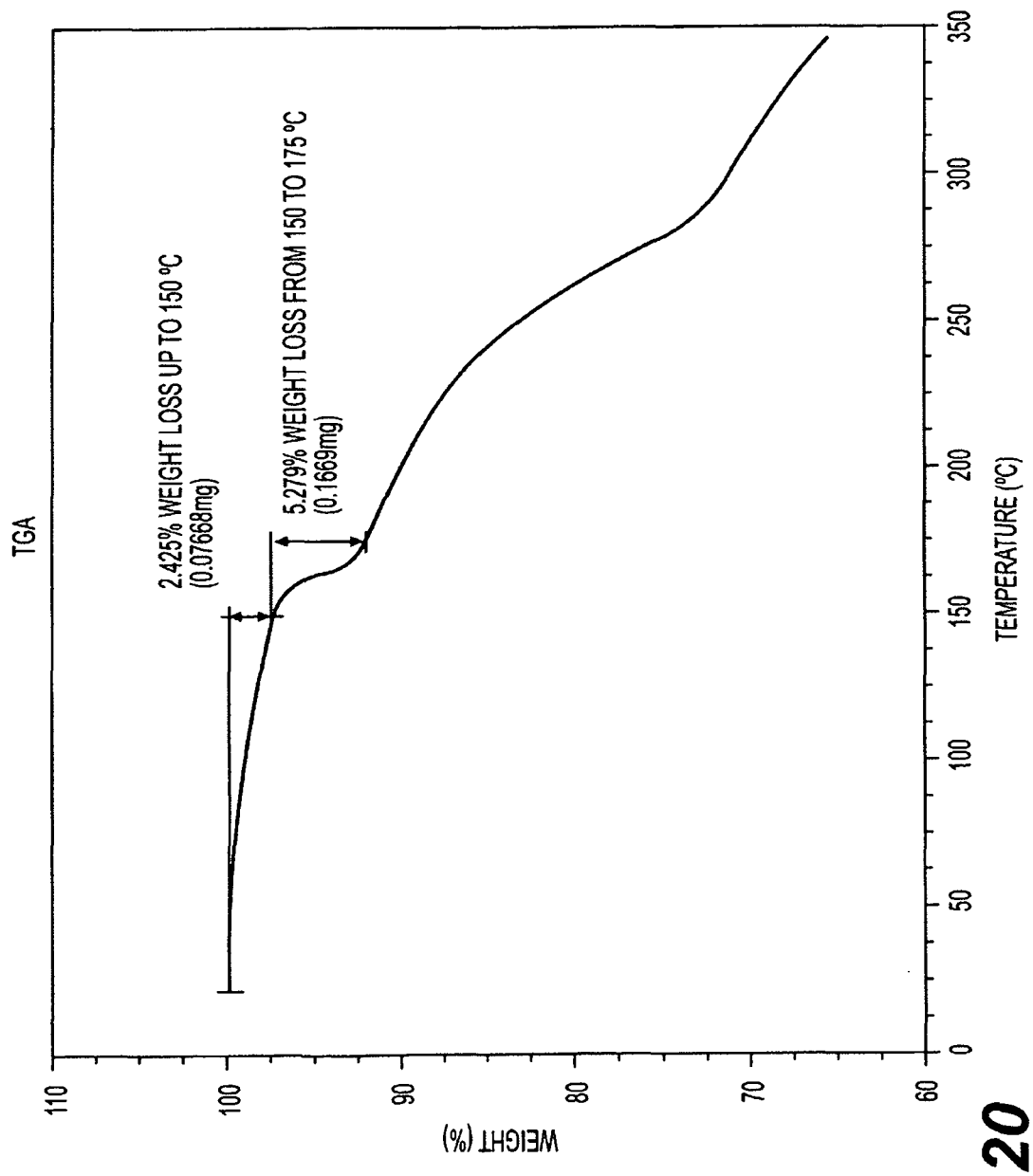
FIG. 20 is the TGA thermogram of racemic ilaprazole, Form F.

FIG. 20 is the TGA thermogram of racemic ilaprazole, Form F. The sample showed a 2.4% weight loss up to 150° C.

Figure 21:
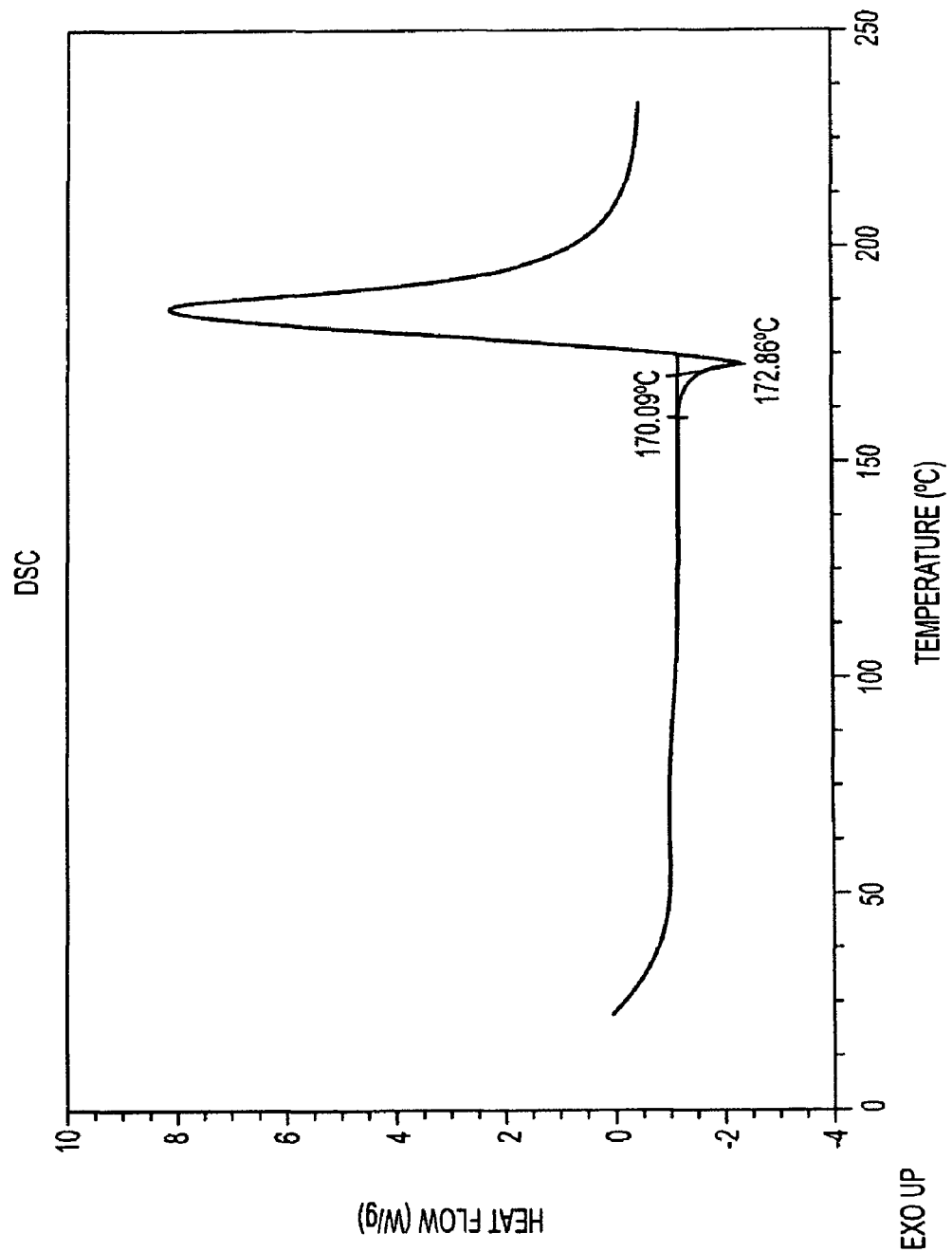
FIG. 21 is the DSC thermogram of racemic ilaprazole, Form F.

FIG. 21 is the DSC thermogram of racemic ilaprazole, Form F. The endotherm onset was at 170° C. (max 173° C.).

Figure 22:
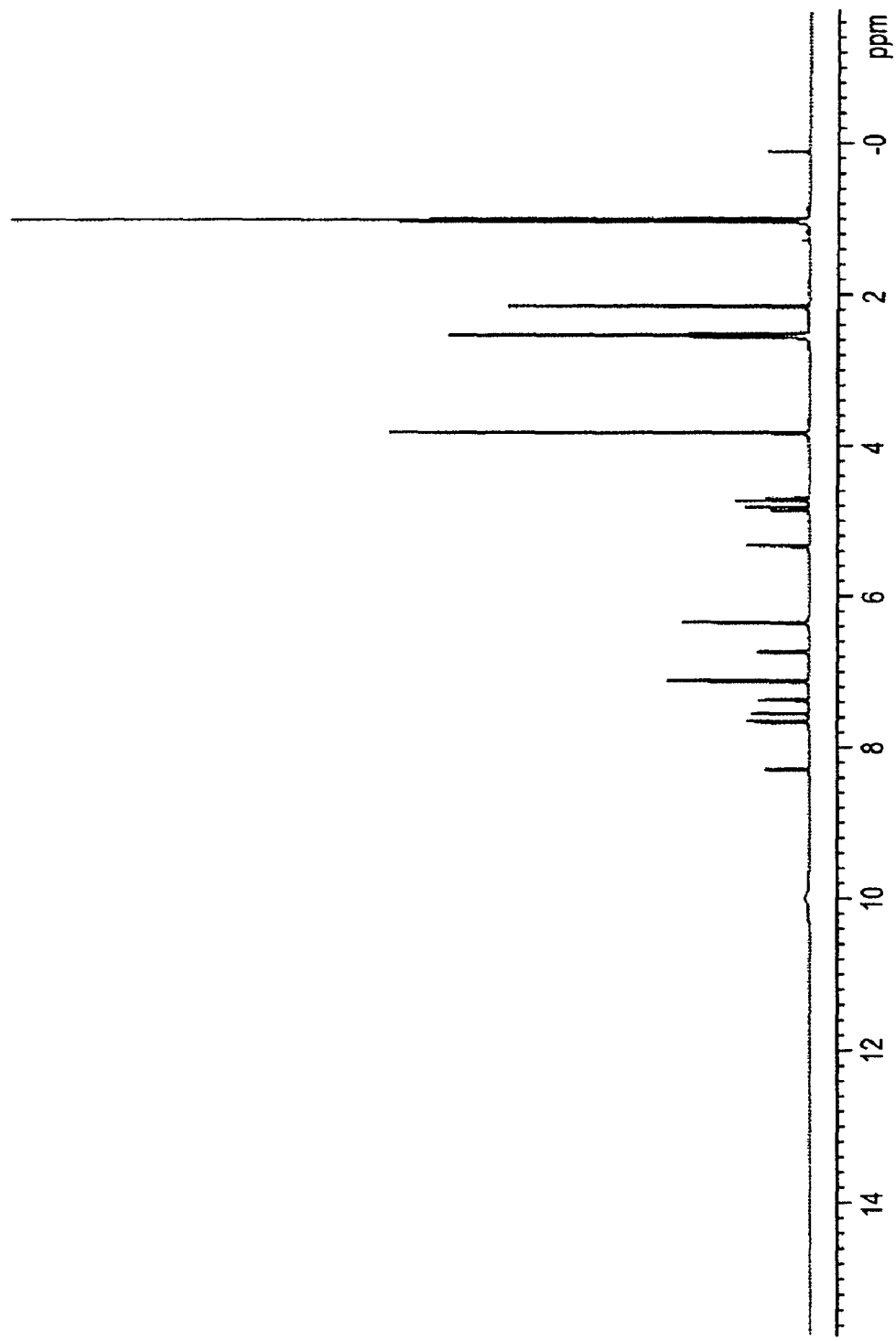
FIG. 22 is the proton NMR spectrum of racemic ilaprazole, Form F.

FIG. 22 is the proton NMR Spectrum of racemic ilaprazole, Form F. Any peaks near 5.32 ppm are due to solvent—not to ilaprazole. Peaks near 1.0 and 2.5 ppm are due to TEA, which is used to stabilize ilaprazole in solution, and not to ilaprazole.

Figure 23:
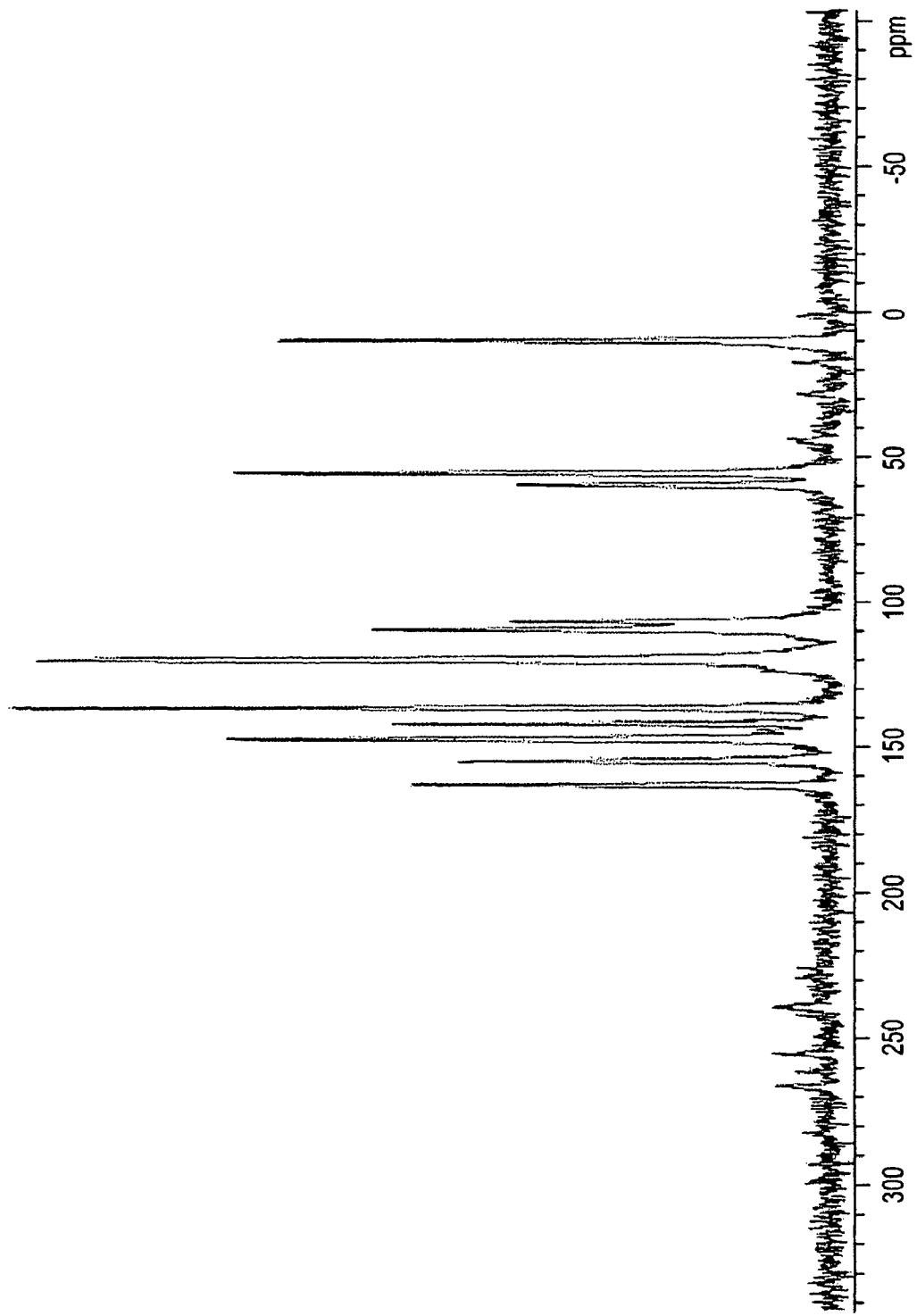
FIG. 23 is the solid state $^{13}$C CP/MAS ssNMR spectrum of racemic ilaprazole Form F.

FIG. 23 is the solid state $^{13}$C CP/MAS NMR spectrum of racemic ilaprazole, Form F. The spectrum is externally referenced against glycine at 176.5 ppm. The peaks in the solid state $^{13}$C NMR spectrum are reported in Table 11.

TABLE 11

Solid State $^{13}$C NMR Peaks for Racemic Ilaprazole, Form F.

| PPM | HEIGHT |
|---|---|
| 164.2 | 72.4 |
| 156.2 | 64.0 |
| 148.4 | 104.2 |
| 143.2 | 75.7 |
| 137.4 | 141.8 |
| 121.2 | 137.2 |
| 110.4 | 79.1 |
| 107.7 | 55.2 |
| 60.3 | 54.1 |
| 56.3 | 103.3 |
| 10.5 | 95.9 |

Figure 24:
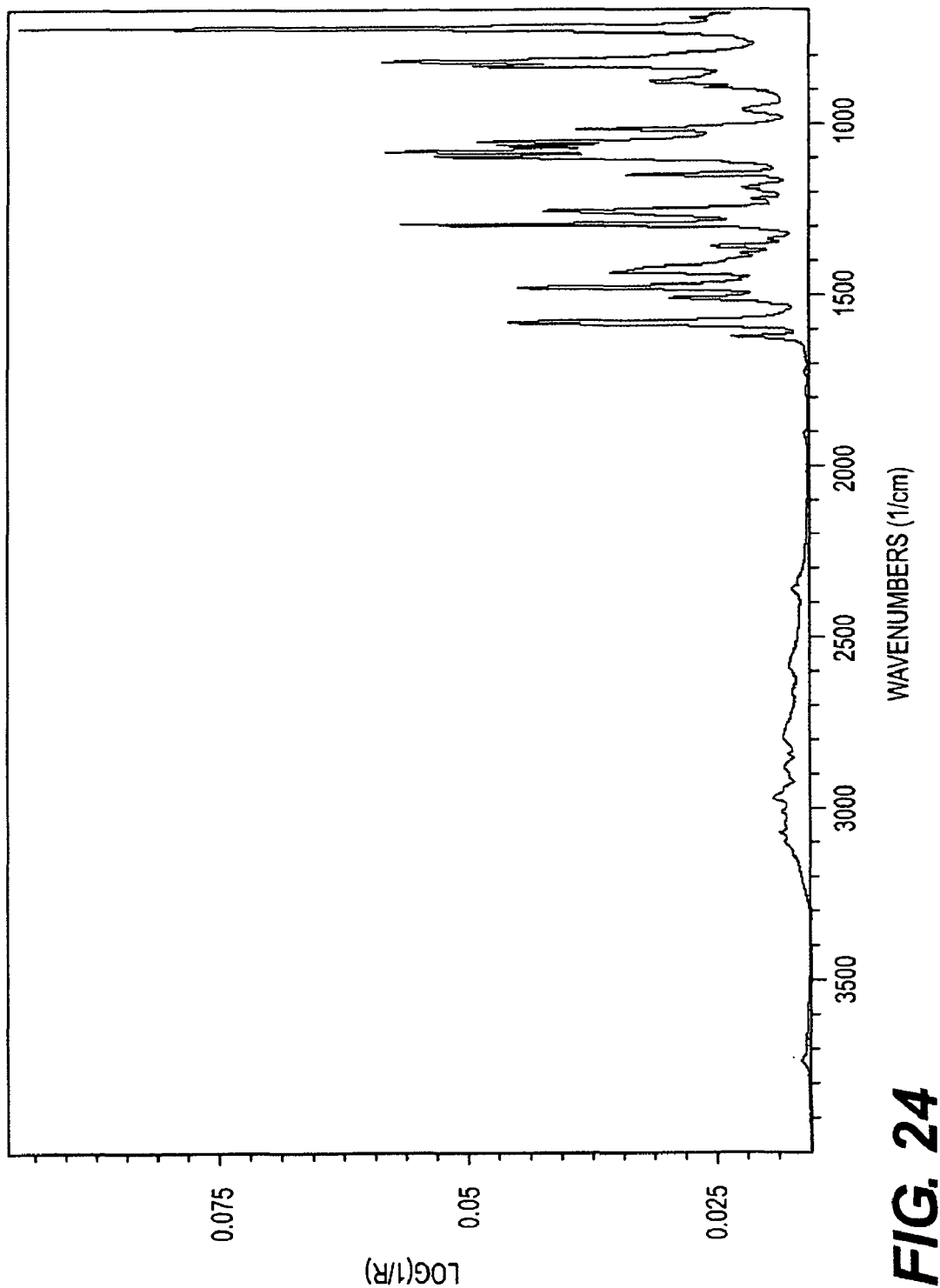
FIG. 24 is the IR spectrum of racemic ilaprazole, Form F.

FIG. 24 is the IR spectrum of racemic ilaprazole, Form F. Table 12 reports the absorbance peaks in the IR spectrum.

TABLE 12

Peaks in IR Spectrum of Racemic Ilaprazole, Form F.

| Position: | | Intensity: | |
|---|---|---|---|
| Position: | 721.3 | Intensity: | 0.0746 |
| Position: | 817.9 | Intensity: | 0.0384 |
| Position: | 833.0 | Intensity: | 0.0296 |
| Position: | 876.1 | Intensity: | 0.0125 |
| Position: | 895.1 | Intensity: | 0.0074 |
| Position: | 962.0 | Intensity: | 0.0038 |
| Position: | 1015.9 | Intensity: | 0.0209 |
| Position: | 1052.9 | Intensity: | 0.0308 |
| Position: | 1064.8 | Intensity: | 0.0289 |
| Position: | 1080.3 | Intensity: | 0.0402 |
| Position: | 1096.5 | Intensity: | 0.0355 |
| Position: | 1148.8 | Intensity: | 0.0160 |
| Position: | 1187.3 | Intensity: | 0.0042 |
| Position: | 1221.1 | Intensity: | 0.0034 |
| Position: | 1255.0 | Intensity: | 0.0246 |
| Position: | 1295.2 | Intensity: | 0.0398 |
| Position: | 1337.4 | Intensity: | 0.0022 |
| Position: | 1358.8 | Intensity: | 0.0081 |
| Position: | 1379.3 | Intensity: | 0.0050 |
| Position: | 1434.2 | Intensity: | 0.0183 |
| Position: | 1454.8 | Intensity: | 0.0053 |
| Position: | 1478.4 | Intensity: | 0.0278 |
| Position: | 1509.7 | Intensity: | 0.0124 |
| Position: | 1580.8 | Intensity: | 0.0293 |
| Position: | 1623.1 | Intensity: | 0.0073 |
| Position: | 1723.7 | Intensity: | 0.00054 |
| Position: | 1903.9 | Intensity: | 0.00058 |
| Position: | 2587.5 | Intensity: | 0.0022 |
| Position: | 2794.3 | Intensity: | 0.0028 |
| Position: | 2841.0 | Intensity: | 0.0022 |
| Position: | 2881.5 | Intensity: | 0.0026 |
| Position: | 2971.7 | Intensity: | 0.0038 |
| Position: | 3011.4 | Intensity: | 0.0030 |
| Position: | 3072.9 | Intensity: | 0.0032 |
| Position: | 3100.8 | Intensity: | 0.0027 |
| Position: | 3735.3 | Intensity: | 0.0010 |

Figure 25:
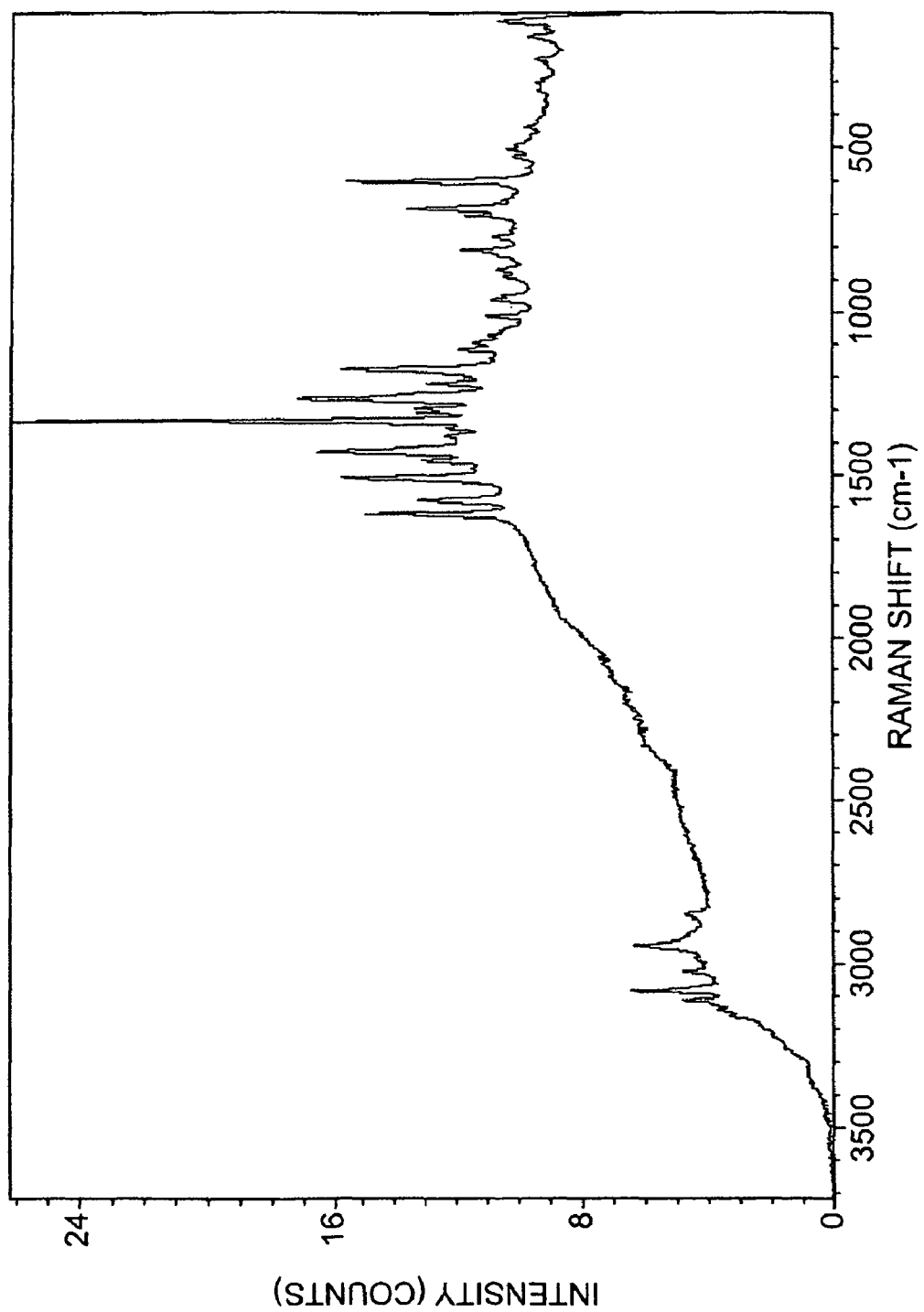
FIG. 25 is the RAMAN spectrum of racemic ilaprazole, Form F.

FIG. 25 is the RAMAN spectrum of racemic ilaprazole, Form F. Table 13 reports the absorbance peaks in the Raman spectrum.

TABLE 13

Peaks in the Raman Spectrum of Racemic Ilaprazole, Form F

| Position: | 100.2 | Intensity: | 2.257 |
|---|---|---|---|
| Position: | 122.9 | Intensity: | 2.700 |
| Position: | 171.0 | Intensity: | 1.653 |
| Position: | 238.3 | Intensity: | 1.247 |
| Position: | 311.8 | Intensity: | 1.028 |
| Position: | 441.9 | Intensity: | 1.048 |
| Position: | 511.4 | Intensity: | 1.464 |
| Position: | 533.6 | Intensity: | 1.198 |
| Position: | 610.5 | Intensity: | 6.403 |
| Position: | 694.6 | Intensity: | 4.080 |
| Position: | 715.5 | Intensity: | 2.084 |
| Position: | 778.0 | Intensity: | 1.180 |
| Position: | 816.8 | Intensity: | 2.217 |
| Position: | 877.2 | Intensity: | 1.112 |
| Position: | 898.2 | Intensity: | 0.895 |
| Position: | 970.7 | Intensity: | 1.336 |
| Position: | 1020.8 | Intensity: | 1.520 |
| Position: | 1081.5 | Intensity: | 1.116 |
| Position: | 1101.4 | Intensity: | 1.434 |
| Position: | 1122.2 | Intensity: | 1.769 |
| Position: | 1182.2 | Intensity: | 5.141 |
| Position: | 1222.7 | Intensity: | 2.099 |
| Position: | 1269.0 | Intensity: | 6.256 |
| Position: | 1298.6 | Intensity: | 2.538 |
| Position: | 1312.2 | Intensity: | 2.544 |
| Position: | 1338.4 | Intensity: | 15.434 |
| Position: | 1360.2 | Intensity: | 1.596 |
| Position: | 1383.9 | Intensity: | 1.700 |
| Position: | 1432.8 | Intensity: | 5.905 |
| Position: | 1460.3 | Intensity: | 2.586 |
| Position: | 1511.7 | Intensity: | 5.232 |

TABLE 13-continued

Peaks in the Raman Spectrum of Racemic Ilaprazole, Form F

| Position: | 1582.7 | Intensity: | 2.970 |
|---|---|---|---|
| Position: | 1624.4 | Intensity: | 4.880 |
| Position: | 2842.4 | Intensity: | 1.136 |
| Position: | 2934.0 | Intensity: | 3.251 |
| Position: | 3014.8 | Intensity: | 2.247 |
| Position: | 3073.7 | Intensity: | 4.180 |
| Position: | 3103.0 | Intensity: | 2.744 |
| Position: | 3131.0 | Intensity: | 1.871 |
| Position: | 3150.4 | Intensity: | 1.583 |

Figure 26:
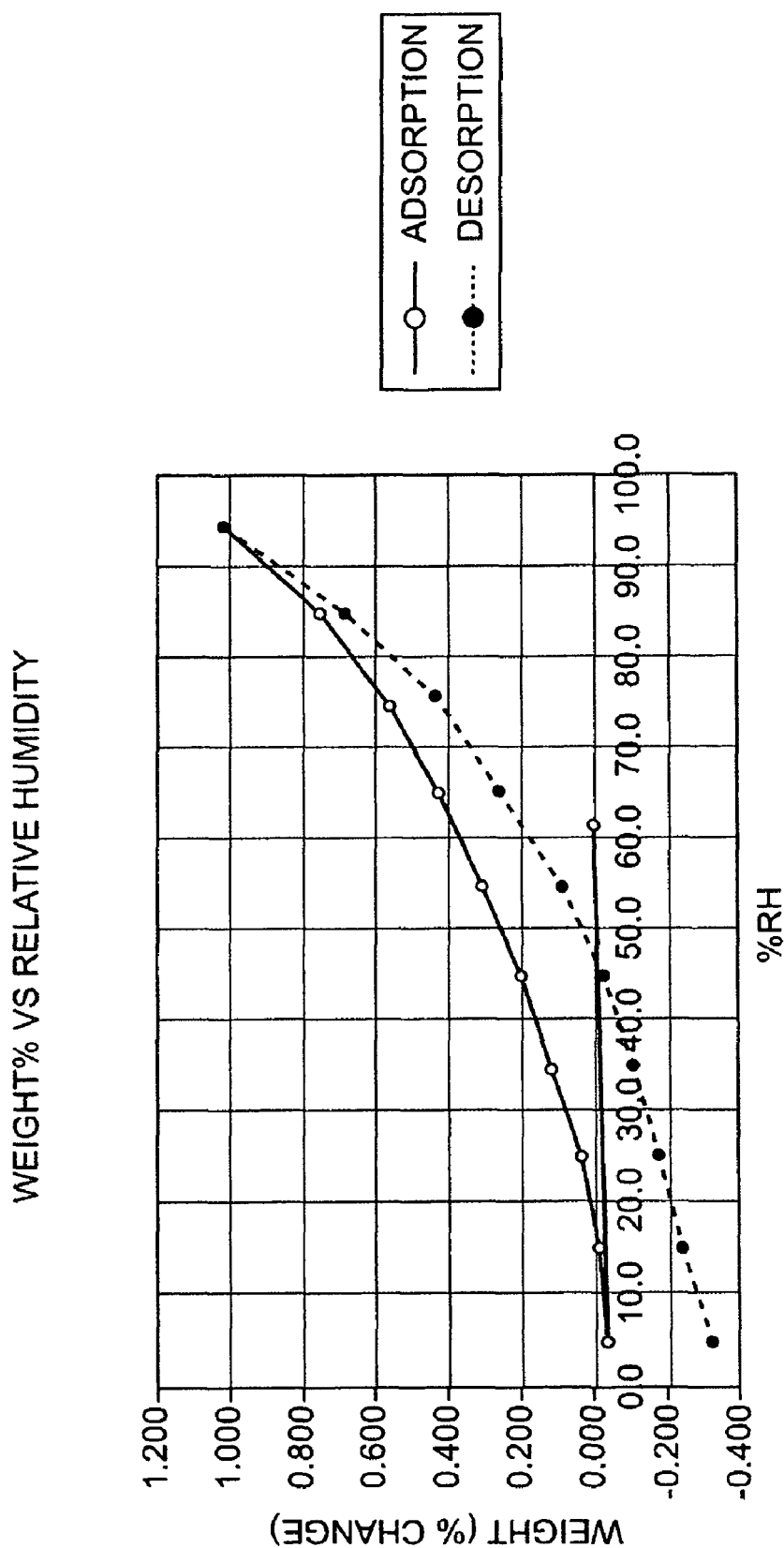
FIG. 26 is the DVS isotherm of racemic ilaprazole, Form F.

FIG. 26 is the DVS isotherm of racemic ilaprazole, Form F. The DVS isotherm shows a 0.04% weight loss at 5% RH, a 1.05% weight gain from 5 to 95% RH, and a 1.33% weight loss from 95 to 5% RH.

A single crystal X-ray diffraction study of racemic ilaprazole, Form F was done using crystals obtained from a acetone/methylene chloride solution. A solution of ilaprazole (~35.8 mg) and piperazine (~10.4 mg) was prepared in a solvent mixture of acetone (2.0 mL) and methylene chloride (0.5 mL) at room temperature. Hexanes (5.0 mL) were added to provide a turbid solution. The vial was sealed and the solution was left, undisturbed, at ambient conditions. Racemic ilaprazole, Form F crystals were observed after six days were subsampled from the parent sample.

The data was collected using a colorless needle of racemic ilaprazole, Form F having approximate dimensions of 0.44× 0.13×0.10 mm, which was mounted on a glass fiber in random orientation. Preliminary examination and data collection were performed with Mo $K_\alpha$ radiation ($\lambda$=0.71073 Å) on a Nonius KappaCCD diffractometer. Refinements were performed on an LINUX PC using SHELX97. Sheldrick, G. M. *SHELX97, A Program for Crystal Structure Refinement*, University of Gottingen, Germany, 1997.

Cell constants and an orientation matrix for data collection were obtained from least-squares refinement using the setting angles of 22729 reflections in the range 2°<θ<27°. The refined mosaicity from DENZO/SCALEPACK (Otwinowski, Z.; Minor, W. *Methods Enzymol.* 1997, 276, 307) is 0.85° indicating moderate to poor crystal quality. The space group was determined by the program XPREP. Bruker, XPREP in SHELXTL v. 6.12., Bruker AXS Inc., Madison, Wis., USE, 2002. From the systematic presence of the following conditions: h0l h+l=2n, 0k0 k=2n and from subsequent least-squares refinement, the space group was determined to be $P2_1/n$ (no. 14). The data were collected to a maximum 2θ value of 54.94°, at a temperature of 150±1 K.

The data reduction was accomplished as follows. The frames were integrated with DENZO-SMN. Otwinowski, et al. supra. A total of 22729 reflections were collected, of which 2277 were unique. Lorentz and polarization corrections were applied to the data. The linear absorption coefficient is 2.0 cm$^{-1}$ for Mo $K_\alpha$ radiation. An empirical absorption correction using SCALEPACK (Otwinowski, et al. supra). was applied. Transmission coefficients ranged from 0.912 to 0.981. Intensities of equivalent reflections were averaged. A secondary extinction correction was applied. The final coefficient, refined in least-squares, was 0.0010000 (in absolute units). The agreement factor for the averaging was 5.4% based on intensity.

The structure was solved by direct methods using PATTY in DIRDIF99. P. T. Beurskens, G. Beurskens, R. deGelderS. Garcia-Granda, R. O. Gould, R. Israel and J. M. M. Smits. The DIRDIF-99 Program System. Crystallography Laboratory, Univ. of Nijmegen, The Netherlands, 1999. The remaining atoms were located in succeeding difference Fourier syntheses, Hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

The weight w is defined as $1/[\sigma^2(F_o^2)+(0.1403P)^2+(0.5425P)]$, where $P=(F_o^2+2F_c^2)/3$.

Scattering factors were taken from the "International Tables for Crystallography." International Tables for Crystallography, Vol. C, Kluwer Academic Publishers: Dordrecht, The Netherlands, 1992, Tables 4.2.6.8 and 6.1.1.4. Of the 2277 reflections used in the refinements, only the reflections with $F_o^2 > 2\sigma(F_o^2)$ were used in calculating R. A total of 1706 reflections were used in the calculation. The final cycle of refinement included 252 variable parameters and converged (largest parameter shift was essentially equal to its estimated standard deviation) with unweighted and weighted agreement factors of:

$$R = \sum |F_o - F_c| \Big/ \sum F_o = 0.066$$

$$R_w = \sqrt{\left(\sum w(F_o^2 - F_c^2)^2 \Big/ \sum w(F_o^2)^2\right)} = 0.174$$

The standard deviation of an observation of unit weight was 1.07. The highest peak in the final difference Fourier had a height of 0.63 e/Å$^3$. The minimum negative peak had a height of -0.46 e/Å$^3$.

A calculated XRPD pattern was generated for Cu $K_\alpha$ radiation using Mercury v 1.3 (Bruno, I. J. Cole, J. C. Edgington, P. R. Kessler, M. K. Macrae, C. F. McCabe, P. Pearson, J. and Taylor, R. Acta Crystallogr., 2002 B58, 389) and the atomic coordinates, space group, and unit cell parameters from the single crystal data.

The ORTEP diagram was prepared using ORTEP III. Johnson, C. K. ORTEPIII, Report ORNL-6895, Oak Ridge National Laboratory, Tenn., U.S.A. 1996. OPTEP-3 for Windows V1.05, Farrugia, L. J., J. Appl. Cryst. 1997, 30, 565. Atoms are represented by 50% probability anisotropic thermal ellipsoids. Packing diagrams were prepared using CAMERON (Watkin, D. J.; Prout, C. K.; Pearce, L. J. CAMERON, Chemical Crystallography Laboratory, University of Oxford, Oxford, 1996) modeling software. Hydrogen bonding is represented as dashed lines. Additional figures were generated using Mercury 1.3 modeling software.

A summary of the crystal data and crystallographic data collection parameters for racemic ilaprazole Form F are provided in Table 14. The monoclinic cell parameters and calculated volume are: a=11.8469(8) Å, b=7.2242(3) Å, c=20.9109(16) Å, α=90.00°, β=102.224(3)°, γ=90.00°, V=1749.07(19)Å$^3$. The formula weight of ilaprazole, Form F is 366.44 g/mol and with Z=4 gives a calculated density of 1.391 g cm$^{-3}$. The space group was determined to be $P2_1/n$. The quality of the structure obtained is moderate, as indicated by the R-value of 0.066 (6.6%). Usually R-values in the range of 0.02 to 0.06 are quoted for the most reliably determined structures. Glusker, Jenny Pickworth; Trueblood, Kenneth N. *Crystal Structure Analysis: A Primer*, 2$^{nd}$ ed.; Oxford University press: New York, 1985; p. 87.

TABLE 14

Single Crystal Data and Data Collection Parameters for Ilaprazole, Form F

| | |
|---|---|
| formula | $C_{19}H_{18}N_4O_2S$ |
| formula weight | 366.44 |
| space group | $P2_1/n$ (No. 14) |
| a, Å | 11.8469(8) |
| b, Å | 7.2242(3) |
| c, Å | 20.9109(16) |
| β, deg | 102.224(3) |
| V, Å$^3$ | 1749.07(19) |
| Z | 4 |
| $d_{calc}$, g cm$^{-3}$ | 1.391 |
| crystal dimensions, mm | 0.44 × 0.13 × 0.10 |
| temperature, K | 150. |
| radiation (wavelength, Å) | Mo K$_\alpha$ (0.71073) |
| monochromator | graphite |
| linear abs coef, mm$^{-1}$ | 0.197 |
| absorption correction applied | empirical$^a$ |
| transmission factors: min, max | 0.912, 0.981 |
| diffractometer | Nonius KappaCCD |
| h, k, l range | 0 to 15 0 to 9 −27 to 26 |
| 2θ range, deg | 4.73-54.95 |
| mosaicity, deg | 0.85 |
| programs used | SHELXTL |
| $F_{000}$ | 768.0 |
| weighting $1/[\sigma^2(F_o^2) + (0.1403P)^2 + 0.5425P]$ where $P = (F_o^2 + 2F_c^2)/3$ | |
| data collected | 22729 |
| unique data | 2277 |
| $R_{int}$ | 0.054 |
| data used in refinement | 2277 |
| cutoff used in R-factor calculations | $F_o^2 > 2.0\sigma(F_o^2)$ |
| data with I > 2.0σ(I) | 1706 |
| refined extinction coef | 0.0010 |
| number of variables | 252 |
| largest shift/esd in final cycle | 0.00 |
| $R(F_o)$ | 0.066 |
| $R_w(F_o^2)$ | 0.174 |
| goodness of fit | 1.072 |

$^a$Otwinowski Z. & Minor, W. Methods Enzymol., 1997, 276, 307.

Figure 27:
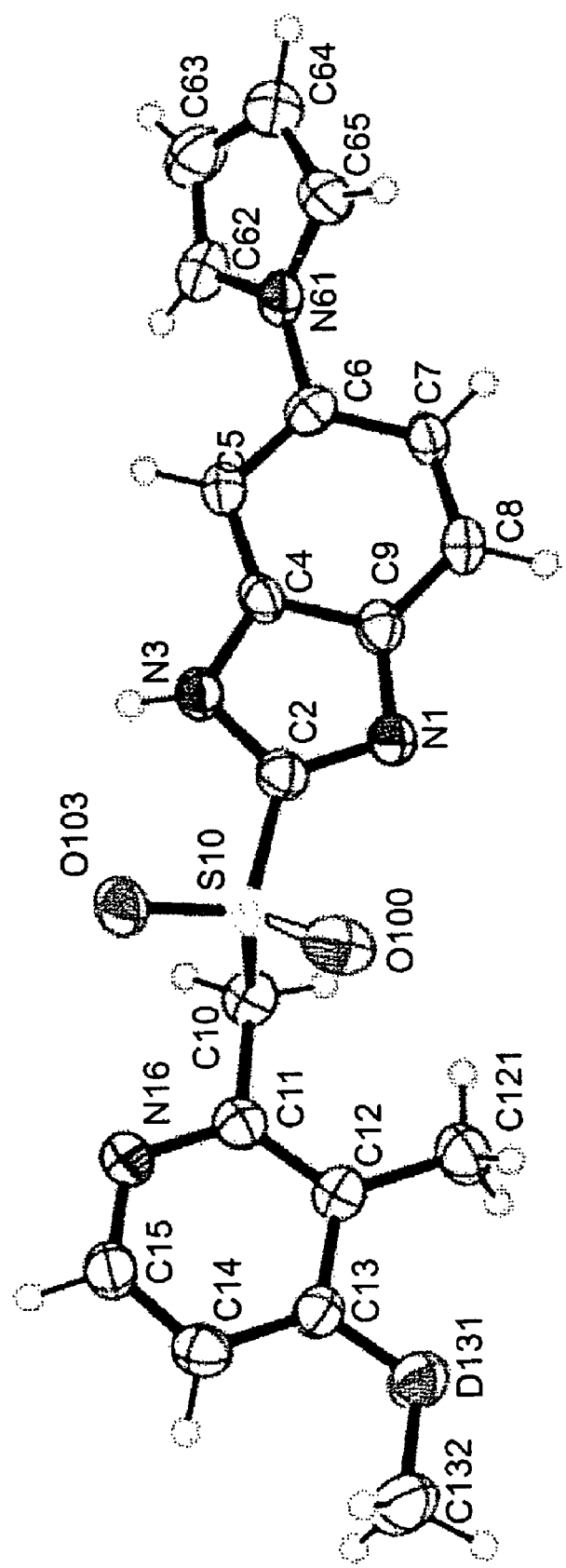
FIG. 27 ORTEP drawing of racemic ilaprazole Form F. Atoms are represented by 50% probability anisotropic thermal ellipsoids

An ORTEP drawing of racemic ilaprazole, Form F is shown in FIG. 27. Atoms are represented by 50% probability anisotropic thermal ellipsoids. The oxygen atom of the sulfinyl group is disordered due to the presence of both enantiomers in the unit cell. The occupancy of the enantiomers was refined to a ratio of approximately 86:14. The ORTEP diagram (FIG. 27) highlights the major enantiomer with a solid bond between S2 and O10a and the minor enantiomer with a hollow bond between S2 and O10b, respectively. The material appears to be an example of a rare class of compounds called "anomalous" racemates, where the stoichiometry of the two enantiomers is not a 1:1 ratio.

Figure 28:
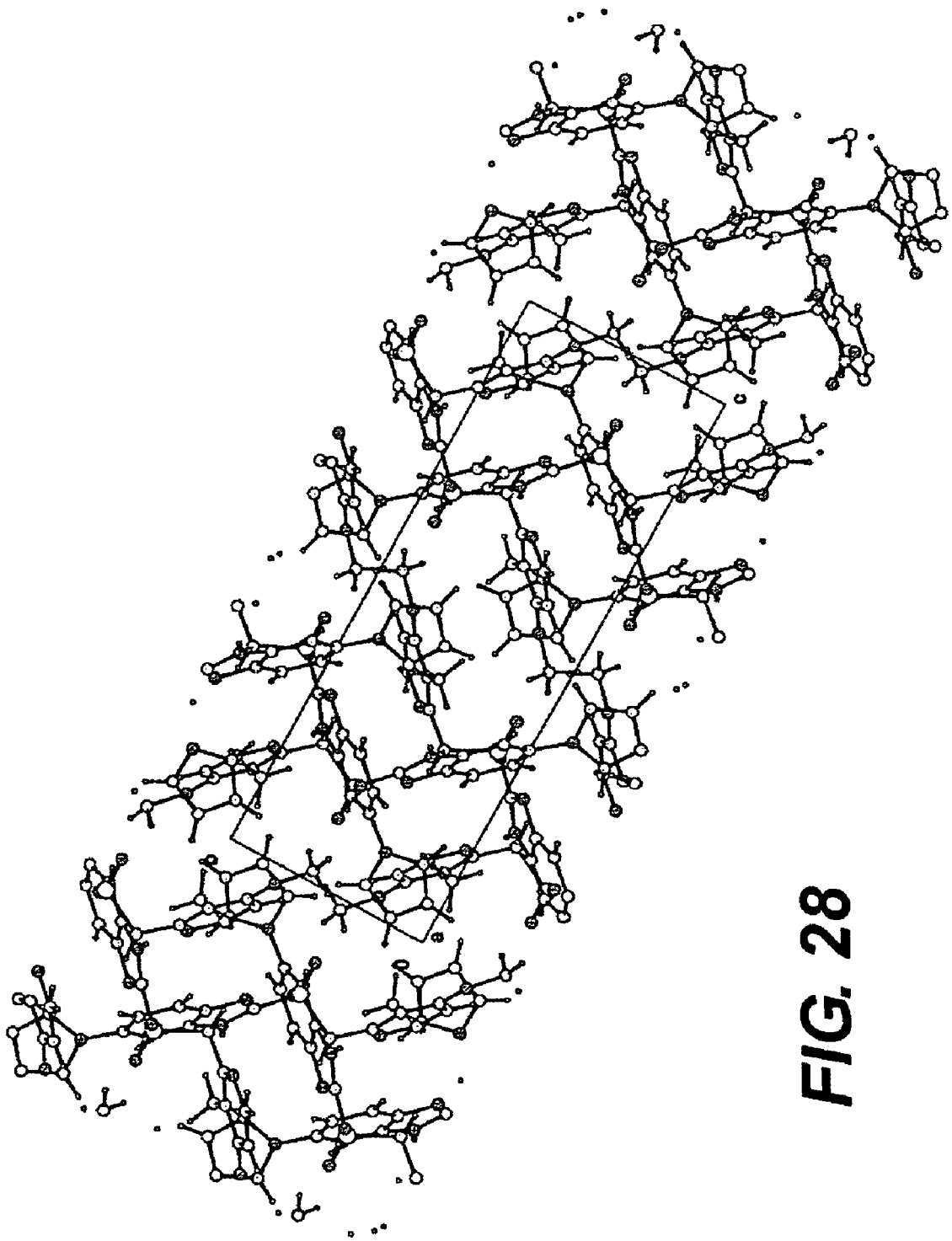
FIG. 28 is the packing diagram of racemic ilaprazole Form F viewed down the crystallographic a axis.
Figure 29:
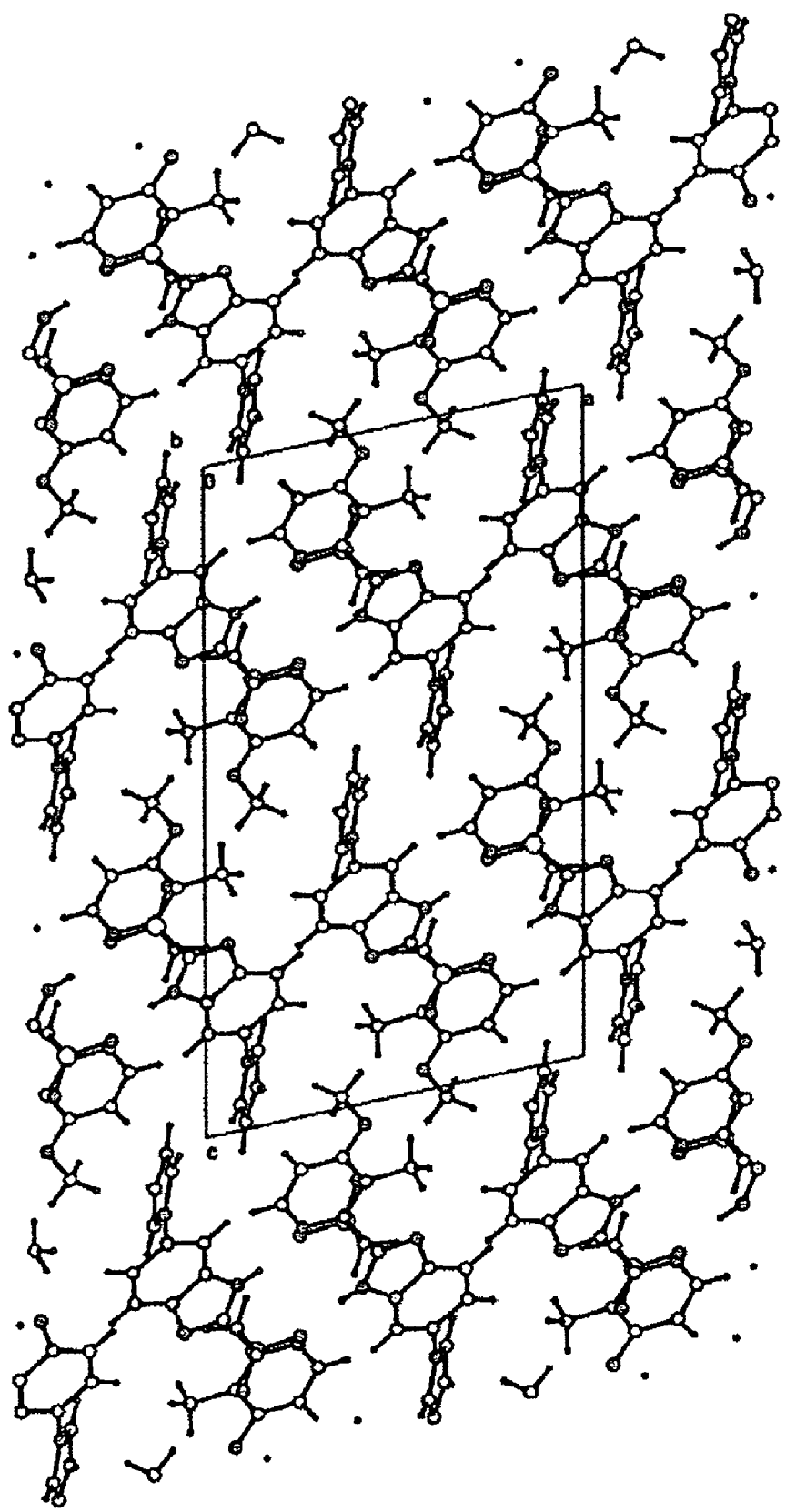
FIG. 29 is the packing diagram of racemic ilaprazole Form F viewed down the crystallographic b axis.
Figure 30:
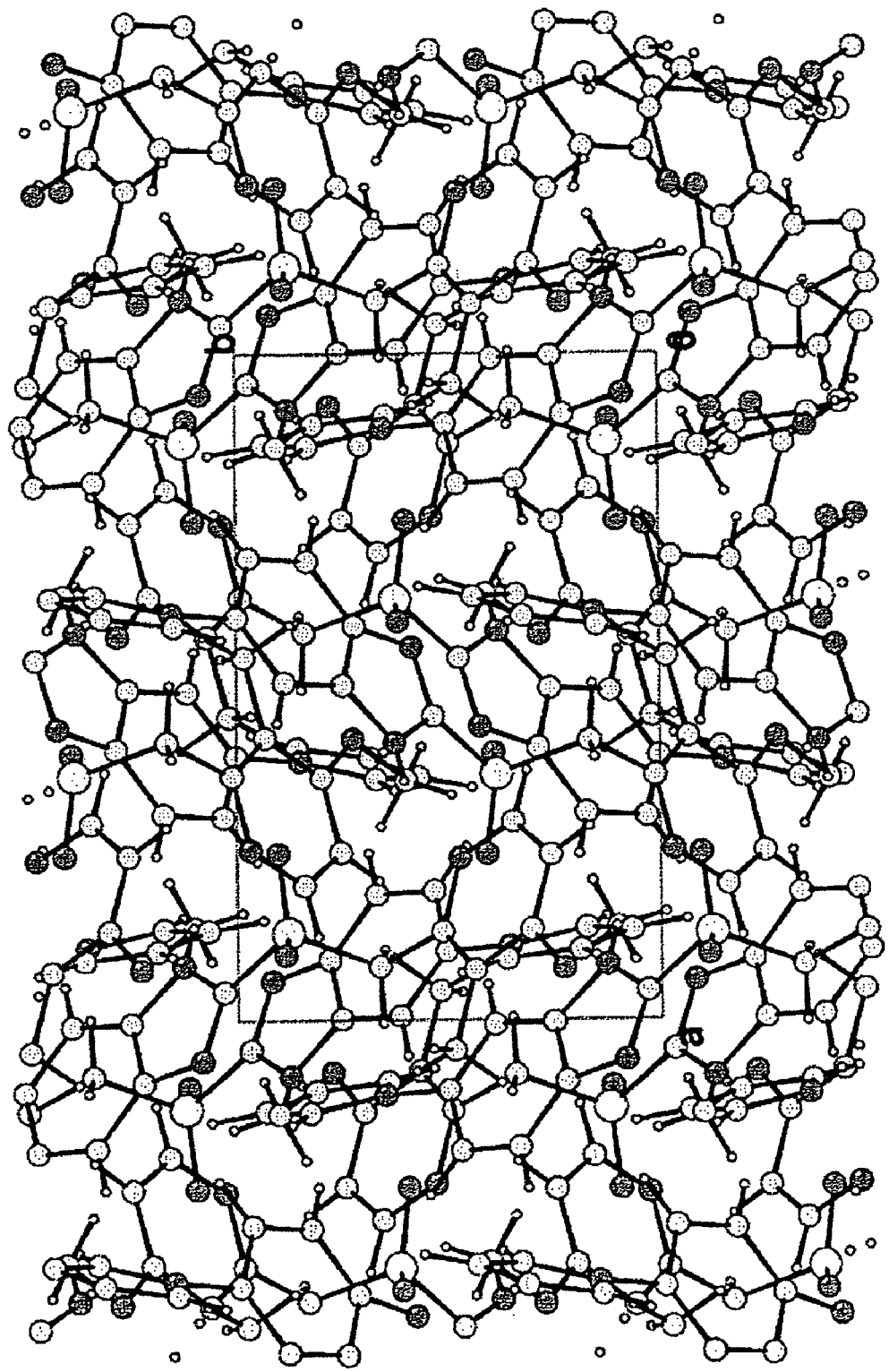
FIG. 30 is the packing diagram of racemic ilaprazole Form F viewed down the crystallographic c axis.

Packing diagrams viewed along the a, b, and c crystallographic axes are shown in FIGS. 28-30 respectively. The packing arrangement of ilaprazole molecules in the Form F crystal structure can be described as sheets of ilaprazole molecules running perpendicular to the crystallographic b axis (FIG. 29). Overlaying the ilaprazole molecule from this crystal structure (FIG. 27) and the ilaprazole molecule from the Form A crystal structure (FIG. 13) showed significant conformational similarity of the ilaprazole molecule in the two crystal structures. The Form F crystal structure consists of layers of ilaprazole molecules packing in a alternating ABAB arrangement.

Hydrogen bonds were observed between the secondary amine (N3) of the benzimidazole ring of one ilaprazole molecule to the pyridine nitrogen (N16) of an adjacent molecule, resulting in a similar hydrogen bonding pattern observed for racemic ilaprazole, Form A. Closer examination of the structure reveals two close contacts between the two oxygen sites of the sulfinyl group. There is a close contact of approximately 3.2 Å between the oxygen atom of the major enantiomer (O10a) and the nitrogen atom secondary amine (N3) of the benzimidazole group. This is not a potential hydrogen bonding interaction because the hydrogen atom is not in a position to interact with the sulfinyl oxygen. The second close contact of approximately 3.0 Å between the oxygen atom of the minor enantiomer (O10b) and the oxygen atom of the ether linkage (O131). This close contact is probably a slightly repulsive interaction since the shorter distance (3.0 Å for Form F and 3.4 Å for Form A) appears to be related to the occupancy of the minor enantiomer (~14% for Form F and ~25% for Form A).

Figure 31:
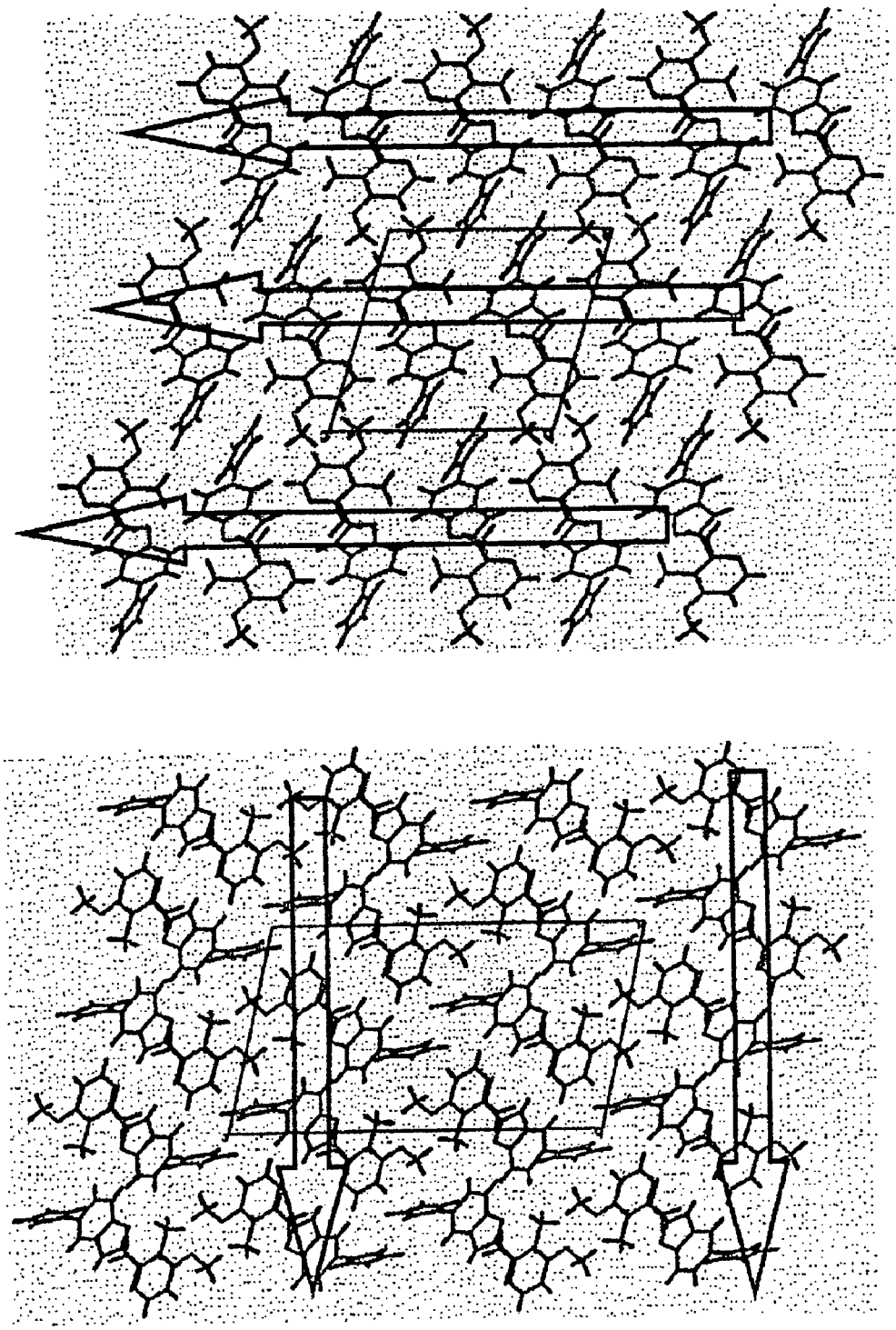
FIG. 31 Comparison of the packing along the crystallographic b axis for racemic ilaprazole Form F (top) and Form A (bottom). The layers are highlighted by arrows show the alternating arrangement of the layers for the Form F crystal structure.

While the molecular conformations are very similar, the packing between the two forms is different. The packing along the crystallographic b axis for racemic ilaprazole, Form A and Form F is shown in FIG. 31. In the Form A crystal structure, the layers run parallel to the crystallographic c axis, while in Form F, the layers run perpendicular to the c axis. The layers propagate in an alternating fashion for the Form F crystal structure, accounting for the doubling of the c axis parameter. The calculated density of the Form A crystal structure (1.396 g cm$^{-3}$) is slightly higher that the Form F crystal structure (1.391 g cm$^{-3}$), suggesting Form A would be more stable at 0 K.

Figure 32:
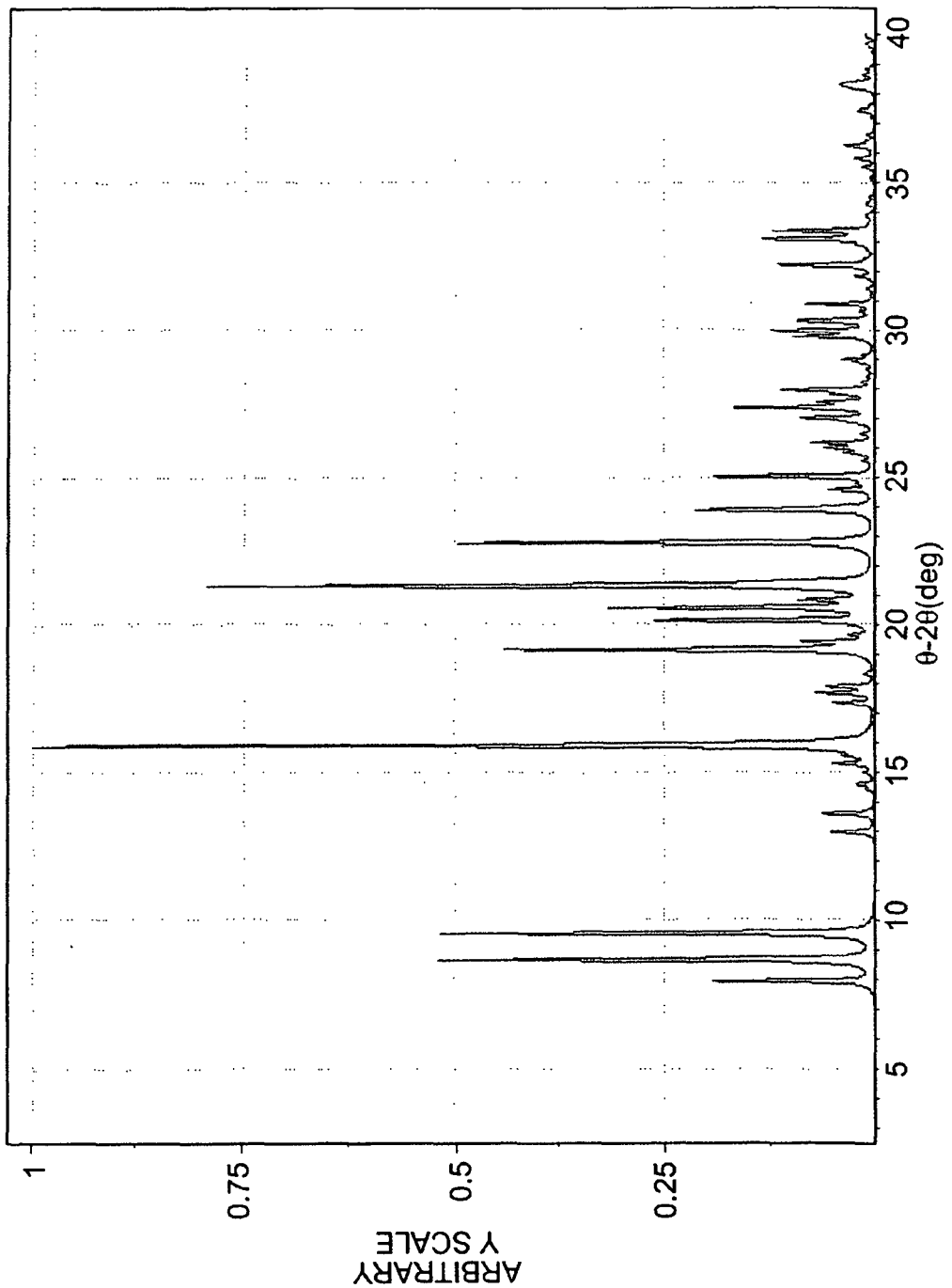
FIG. 32 is the calculated X-ray powder pattern of racemic ilaprazole, Form F.
Figure 33:
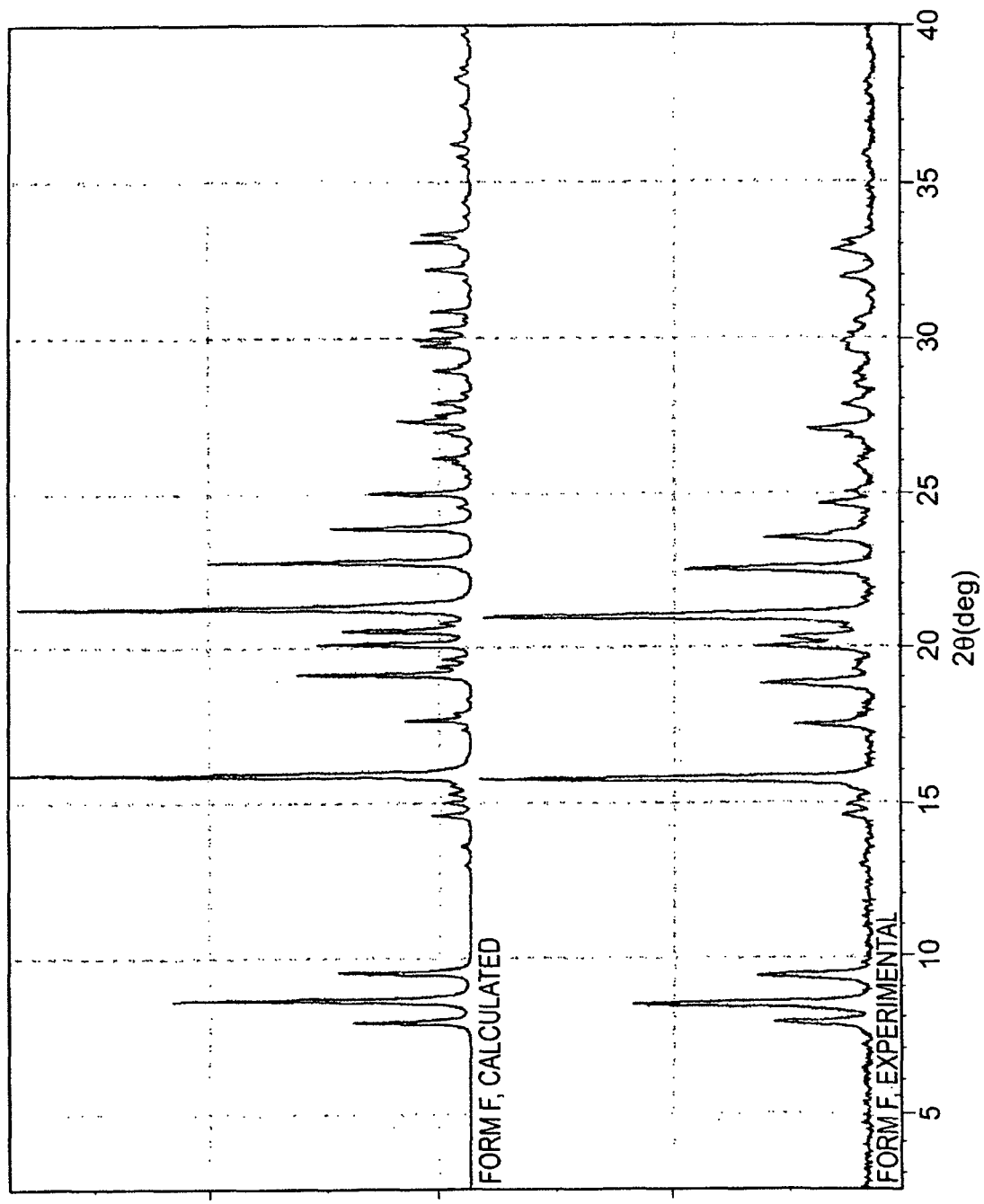
FIG. 33 is a comparison of the calculated XRPD of racemic ilaprazole, Form F (top) with the experimental XRPD of racemic ilaprazole, Form F (bottom).

FIG. 31 shows a calculated XRPD pattern of ilaprazole, From F, generated from the single crystal data. The experimental BPD pattern of ilaprazole, Form F is show in FIG. 32 and a comparison of the calculated and experimental powder diffraction patterns is shown in FIG. 33. All peaks in the experimental patterns are represented in the calculated XRPD pattern, indicating the bulk material is likely a single phase. The slight shifts in peak location are likely due to the fact that the experimental powder pattern was collected at ambient temperature, and the single crystal data was collected at 150 K. Low temperatures are used in single crystal analysis to improve the quality of the structure.

Example 4

Preparation and Characterization of Racemic Ilaprazole, Form I

A solution containing 3 mL of methanol (MeOU) and 10 μL triethylamine (TEA) was saturated with racemic ilaprazole Form A by sonicating with excess solids for approximately 3 minutes. The resulting slurry was filtered through a 0.2 micron nylon filter into a glass vial. The vial was capped and placed into the freezer. The resulting white solid was collected by vacuum filtration approximately 2 days later as the methanol solvate, Form G, which is believed to be a variable solvate. A small spatula full of Form C (e.g. >30 mg) was placed in a 1 dram glass vial. The open vial was exposed to ambient temperature under vacuum. A white solid resulted approximately 1 day later as Form I.

Figure 34:
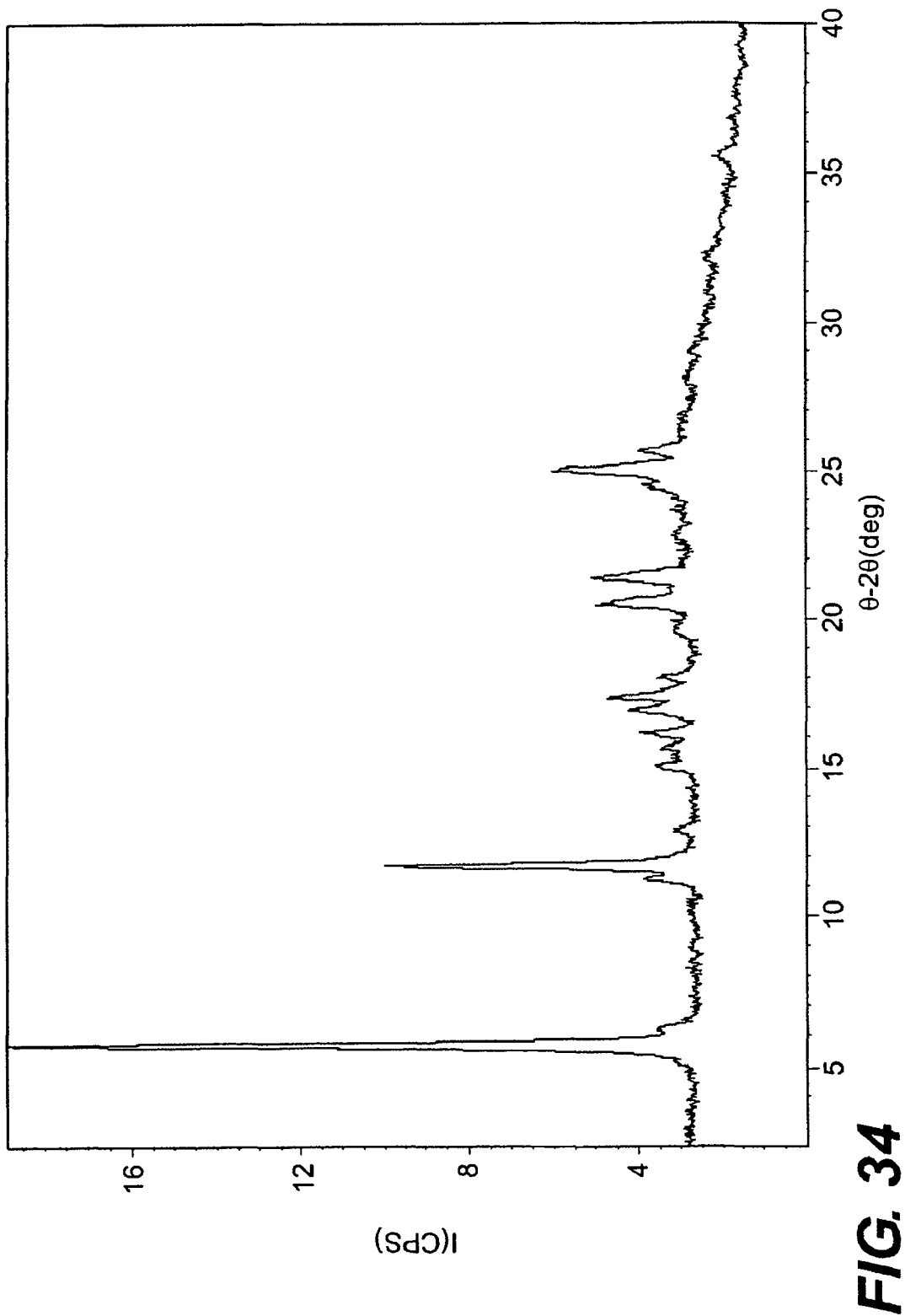
FIG. 34 is the XDPD pattern of racemic ilaprazole, Form I.

The XRPD pattern of racemic ilaprazole, Form I was obtained using an Inel XRG-3000 diffractometer, as described above. The measurement conditions are reported in Table 15. FIG. 34 shows the XRPD pattern for racemic ilaprazole, Form I. Table 16 reports the peaks identified in the XRPD pattern. In its XRPD racemic ilaprazole, Form I may be characterized by peaks at 11.9° 2θ±0.2° 2θ; 17.1° 2θ±0.2° 2θ; 21.5° 2θ±0.2° 2θ and 25.1° 2θ±0.2° 2θ. Another characteristic grouping includes peaks at 5.9 2θ+0.2° 2θ; 12.2 2θ±0.2° 2θ, and 35.6 2θ±0.2° 2θ.

TABLE 15

Measurement Conditions for XRPD Pattern of Racemic Ilaprazole, Form I.

Measurement Condition:

X-ray tube

| | |
|---|---|
| target = | Cu |
| voltage = | 40.0 (kV) |
| current = | 30.0 (mA) |

Slits

| | |
|---|---|
| divergence slit = | 1.00000 (deg) |
| scatter slit = | 1.00000 (deg) |
| receiving slit = | 0.15000 (mm) |

Scanning

| | |
|---|---|
| drive axis = | 2Theta/Theta |
| scan range = | 2.507-39.987 |
| scan mode = | Continuous Scan |
| scan speed = | 0.0040 (deg/min) |
| sampling pitch = | 0.0200 (deg) |
| preset time = | 300.00 (sec) |

Data Process Condition:

| | |
|---|---|
| Smoothing | [AUTO] |
| smoothing points = | 11 |
| B.G. Subtraction | [AUTO] |
| sampling points = | 13 |
| repeat times = | 30 |
| Ka1-a2 Separate | [MANUAL] |
| Ka1 a2 ratio = | 50.0 (%) |
| Peak Search | [AUTO] |
| differential points = | 11 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 16

Peak Positions of Ilaprazole, Form I XRPD Pattern

| Peak No. | Position (°2θ ± 0.2 °2θ) | d-spacing | Intensity | I/I$_o$ |
|---|---|---|---|---|
| 1 | 5.9 | 15.0 | 3236 | 100 |
| 2 | 6.5 | 13.7 | 182 | 6 |
| 3 | 11.4 | 7.8 | 254 | 8 |
| 4 | 11.9 | 7.5 | 1453 | 45 |
| 5 | 12.2 | 7.2 | 100 | 3 |
| 6 | 13.0 | 6.8 | 101 | 3 |
| 7 | 15.1 | 5.8 | 174 | 5 |
| 8 | 15.8 | 5.6 | 142 | 4 |
| 9 | 16.2 | 5.5 | 198 | 6 |
| 10 | 17.1 | 5.2 | 283 | 9 |
| 11 | 17.5 | 5.1 | 391 | 12 |
| 12 | 17.8 | 5.0 | 125 | 4 |
| 13 | 18.1 | 4.9 | 167 | 5 |
| 14 | 20.6 | 4.3 | 402 | 12 |
| 15 | 21.5 | 4.1 | 458 | 14 |
| 16 | 21.7 | 4.1 | 183 | 6 |
| 17 | 24.6 | 3.6 | 180 | 6 |
| 18 | 25.1 | 3.5 | 618 | 19 |
| 19 | 25.3 | 3.5 | 207 | 6 |
| 20 | 25.7 | 3.5 | 219 | 7 |
| 21 | 35.6 | 2.5 | 98 | 3 |

Figure 35:
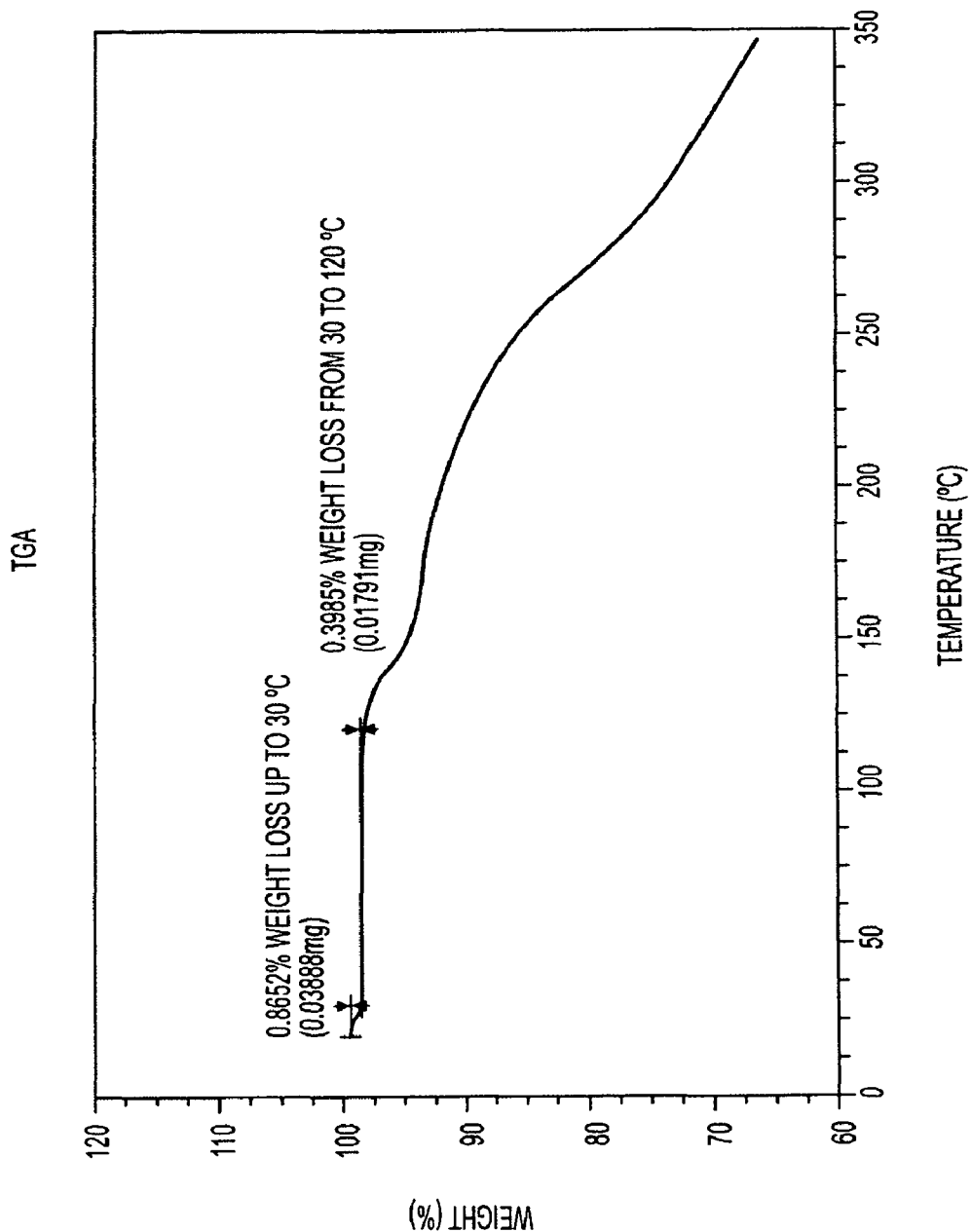
FIG. 35 is the TGA thermogram of racemic ilaprazole, Form I.

FIG. 35 is the TCA thermogram of racemic ilaprazole, Form I. The sample showed a 0.9% weight loss up to 30° C. and 0.4% weight loss between 30 and 120° C.

Figure 36:
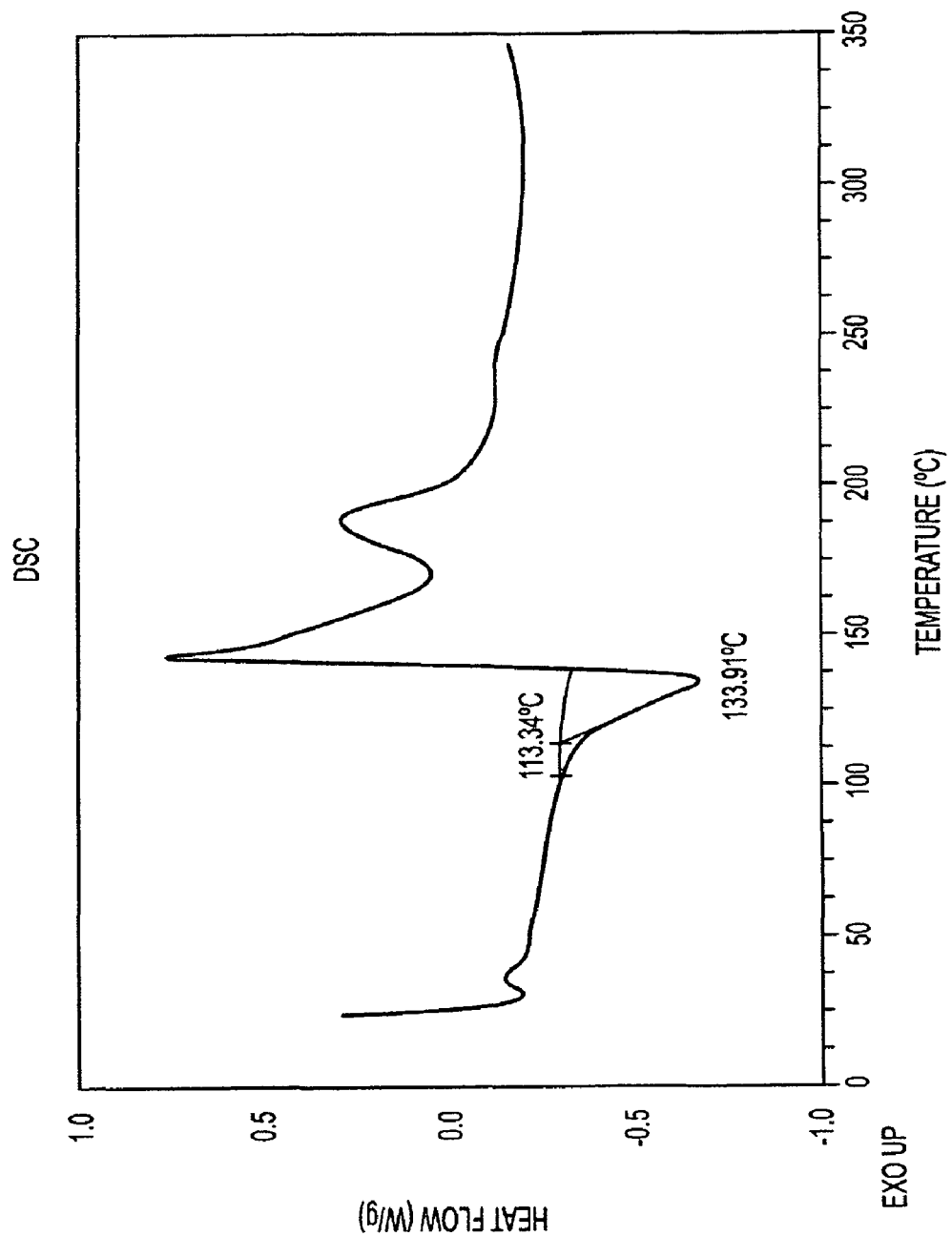
FIG. 36 is the DSC thermogram of racemic ilaprazole, Form I.

FIG. 36 is the DSC thermogram of racemic ilaprazole, Form I. The endotherm onset occurred at 113° C. (max 134° C.).

Figure 37:
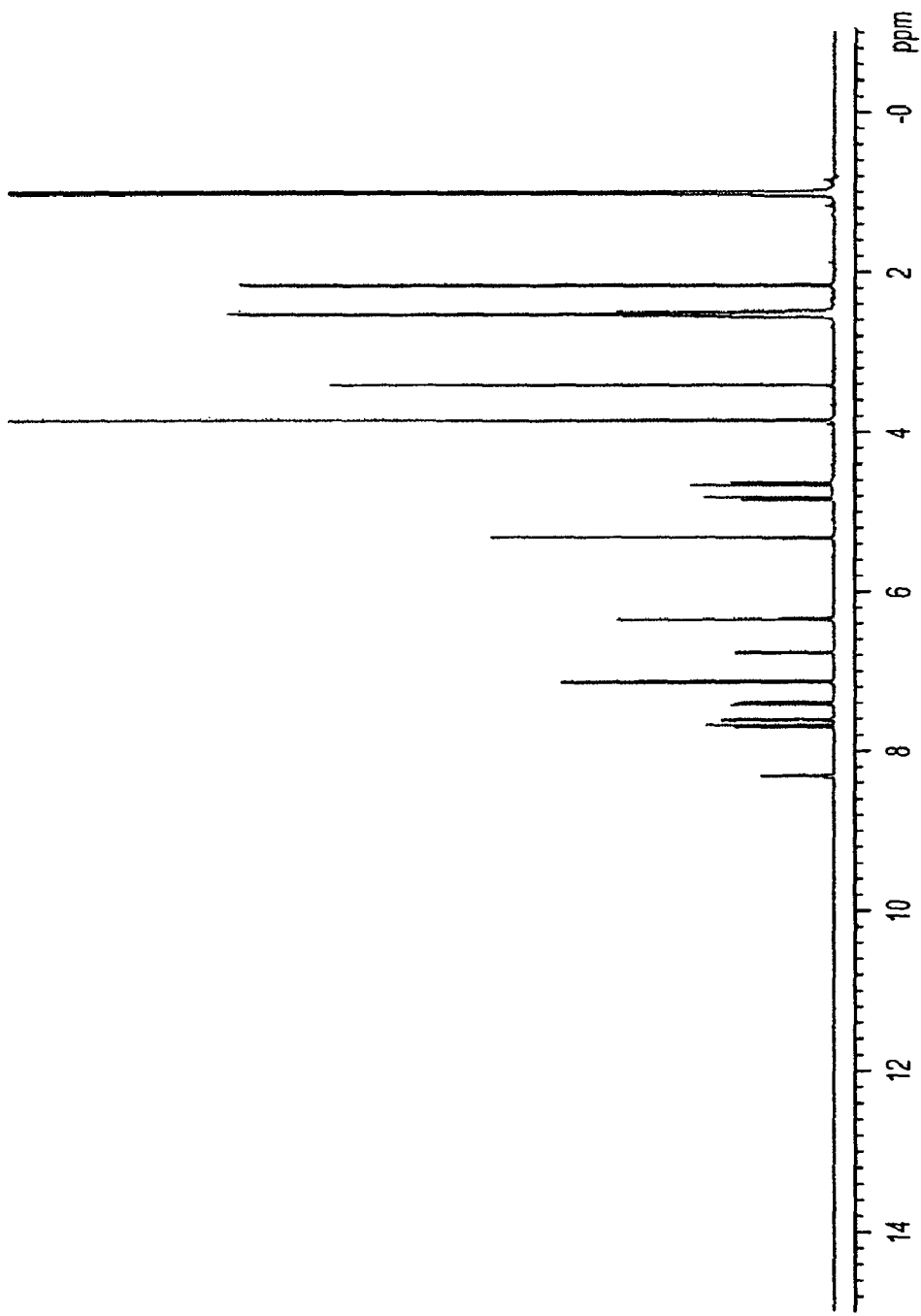
FIG. 37 is the proton NMR spectrum of racemic ilaprazole, Form I.

FIG. 37 is the proton NMR Spectrum of racemic ilaprazole, Form I. Any peaks near 5.32 ppm are due to solvent—not to ilaprazole. Peaks near 1.0 and 2.5 ppm are due to TEA, which is used to stabilize ilaprazole in solution, and not to ilaprazole.

Figure 38:
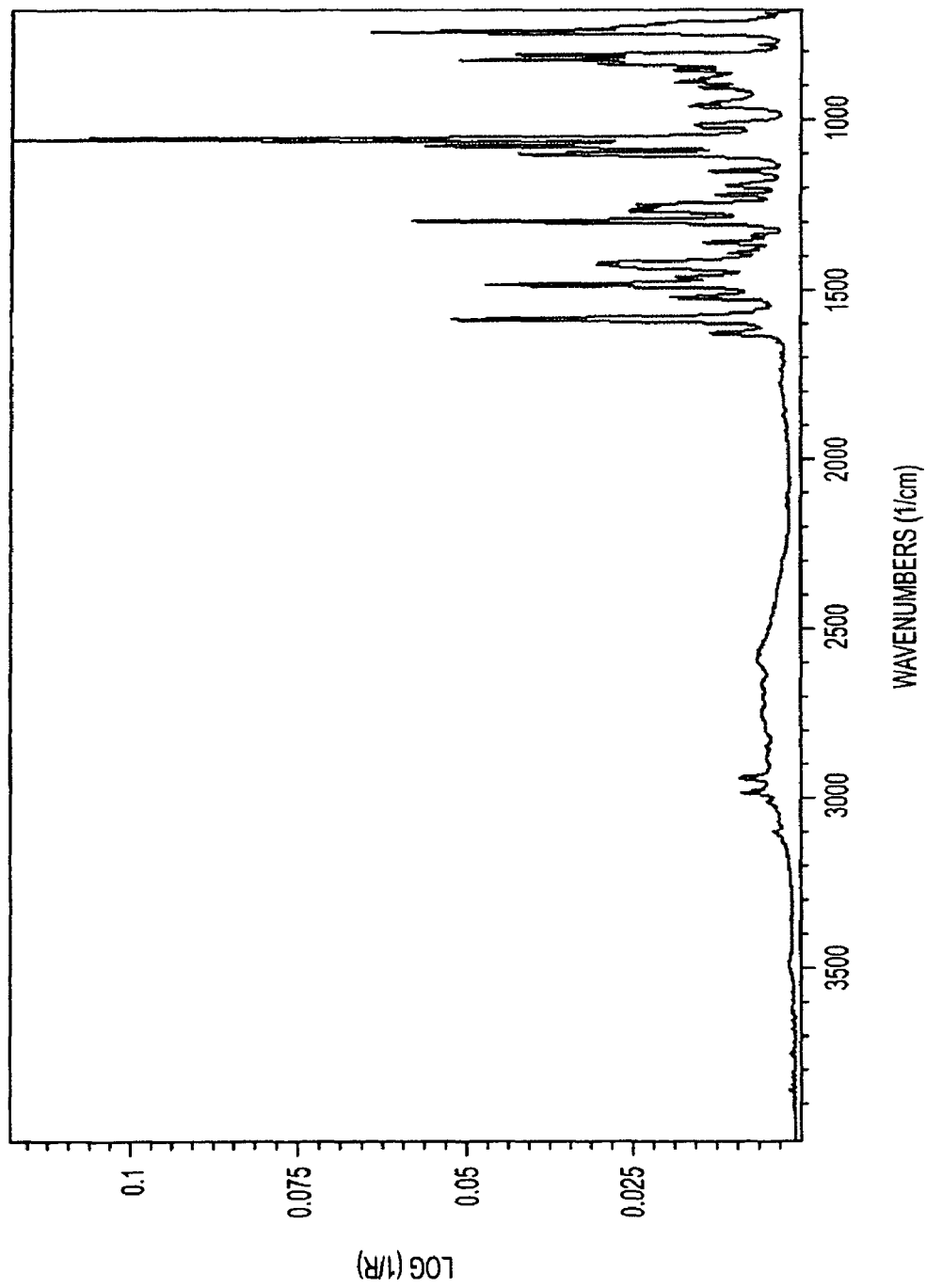
FIG. 38 is the IR spectrum of racemic ilaprazole, Form I.

FIG. 38 is the IR spectrum of racemic ilaprazole, Form I. Table 17 reports the absorbance peaks in the IR spectrum.

TABLE 17

Peaks in IR Spectrum of Racemic Ilaprazole, Form I.

| | | | |
|---|---|---|---|
| Position: | 716.8 | Intensity: | 0.0196 |
| Position: | 729.6 | Intensity: | 0.0262 |
| Position: | 744.1 | Intensity: | 0.0620 |
| Position: | 780.3 | Intensity: | 0.0037 |
| Position: | 810.6 | Intensity: | 0.0407 |
| Position: | 825.0 | Intensity: | 0.0488 |
| Position: | 838.3 | Intensity: | 0.0278 |
| Position: | 857.0 | Intensity: | 0.0163 |
| Position: | 880.8 | Intensity: | 0.0124 |
| Position: | 890.5 | Intensity: | 0.0160 |
| Position: | 906.6 | Intensity: | 0.0124 |
| Position: | 951.5 | Intensity: | 0.0108 |
| Position: | 960.8 | Intensity: | 0.0138 |
| Position: | 1015.6 | Intensity: | 0.0133 |
| Position: | 1021.5 | Intensity: | 0.0128 |
| Position: | 1057.0 | Intensity: | 0.115 |
| Position: | 1077.1 | Intensity: | 0.0548 |
| Position: | 1101.0 | Intensity: | 0.0396 |
| Position: | 1151.4 | Intensity: | 0.0111 |
| Position: | 1193.5 | Intensity: | 0.0082 |
| Position: | 1220.1 | Intensity: | 0.0099 |
| Position: | 1248.7 | Intensity: | 0.0217 |
| Position: | 1259.9 | Intensity: | 0.0222 |
| Position: | 1267.8 | Intensity: | 0.0227 |
| Position: | 1296.6 | Intensity: | 0.0558 |
| Position: | 1338.8 | Intensity: | 0.0042 |
| Position: | 1359.1 | Intensity: | 0.0112 |
| Position: | 1375.5 | Intensity: | 0.0032 |
| Position: | 1390.2 | Intensity: | 0.0072 |
| Position: | 1421.3 | Intensity: | 0.0266 |
| Position: | 1462.3 | Intensity: | 0.0146 |
| Position: | 1482.5 | Intensity: | 0.0436 |
| Position: | 1521.2 | Intensity: | 0.0148 |
| Position: | 1585.4 | Intensity: | 0.0487 |
| Position: | 1627.3 | Intensity: | 0.0103 |
| Position: | 1774.6 | Intensity: | 0.00059 |
| Position: | 1869.5 | Intensity: | 0.00049 |
| Position: | 2589.6 | Intensity: | 0.0052 |
| Position: | 2658.0 | Intensity: | 0.0045 |
| Position: | 2751.5 | Intensity: | 0.0046 |
| Position: | 2841.8 | Intensity: | 0.0040 |
| Position: | 2876.7 | Intensity: | 0.0039 |
| Position: | 2937.2 | Intensity: | 0.0079 |
| Position: | 2980.8 | Intensity: | 0.0079 |
| Position: | 3006.7 | Intensity: | 0.0040 |
| Position: | 3095.2 | Intensity: | 0.0030 |
| Position: | 3481.1 | Intensity: | 0.00066 |

Figure 39:
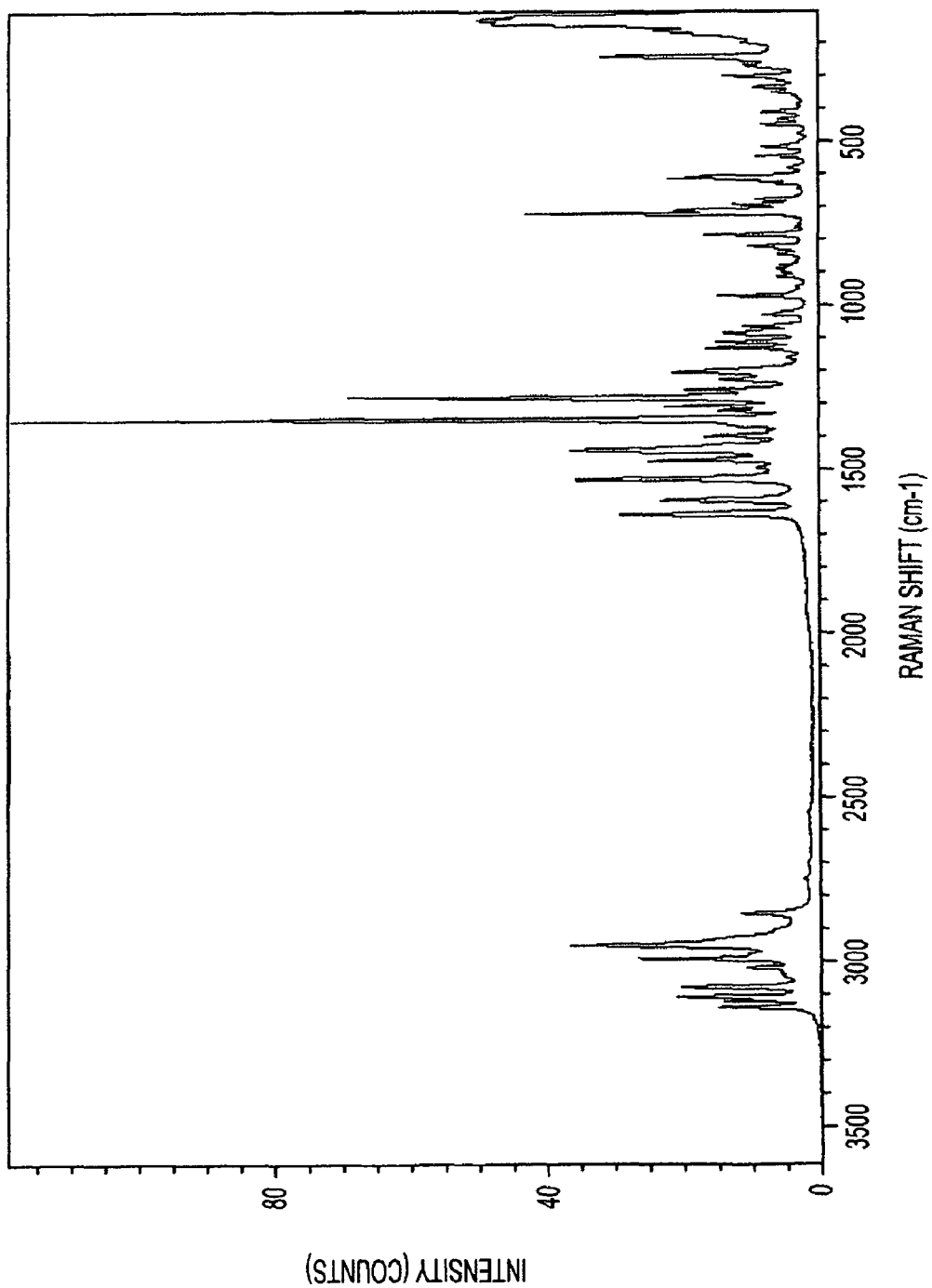
FIG. 39 is the RAMAN spectrum of racemic ilaprazole, Form I.

FIG. 39 is the RAMAN spectrum of racemic ilaprazole, Form I. Table 18 reports the absorbance peaks in the Raman spectrum

TABLE 18

Peaks in the Raman Spectrum of Racemic Ilaprazole, Form I.

| | | | |
|---|---|---|---|
| Position: | 402.5 | Intensity: | 6.251 |
| Position: | 423.4 | Intensity: | 4.046 |
| Position: | 439.3 | Intensity: | 6.695 |
| Position: | 467.2 | Intensity: | 1.280 |
| Position: | 508.9 | Intensity: | 6.226 |
| Position: | 537.0 | Intensity: | 7.294 |
| Position: | 575.9 | Intensity: | 2.058 |
| Position: | 602.1 | Intensity: | 14.741 |
| Position: | 608.4 | Intensity: | 19.813 |
| Position: | 625.0 | Intensity: | 3.686 |
| Position: | 641.3 | Intensity: | 0.343 |
| Position: | 671.9 | Intensity: | 6.680 |

TABLE 18-continued

Peaks in the Raman Spectrum of Racemic Ilaprazole, Form I.

| | | | |
|---|---|---|---|
| Position: | 687.4 | Intensity: | 10.109 |
| Position: | 705.1 | Intensity: | 18.324 |
| Position: | 715.2 | Intensity: | 40.085 |
| Position: | 746.3 | Intensity: | 0.223 |
| Position: | 757.2 | Intensity: | 0.657 |
| Position: | 779.3 | Intensity: | 13.833 |
| Position: | 814.4 | Intensity: | 7.625 |
| Position: | 824.3 | Intensity: | 3.724 |
| Position: | 839.5 | Intensity: | 3.268 |
| Position: | 858.2 | Intensity: | 0.596 |
| Position: | 872.3 | Intensity: | 2.936 |
| Position: | 883.2 | Intensity: | 3.271 |
| Position: | 892.6 | Intensity: | 2.679 |
| Position: | 906.6 | Intensity: | 3.272 |
| Position: | 937.9 | Intensity: | 0.628 |
| Position: | 964.6 | Intensity: | 12.167 |
| Position: | 1022.4 | Intensity: | 5.498 |
| Position: | 1058.4 | Intensity: | 8.147 |
| Position: | 1078.3 | Intensity: | 11.286 |
| Position: | 1105.5 | Intensity: | 12.333 |
| Position: | 1122.2 | Intensity: | 13.568 |
| Position: | 1153.0 | Intensity: | 1.822 |
| Position: | 1195.6 | Intensity: | 18.478 |
| Position: | 1218.6 | Intensity: | 11.741 |
| Position: | 1248.5 | Intensity: | 17.145 |
| Position: | 1271.0 | Intensity: | 66.038 |
| Position: | 1298.3 | Intensity: | 19.951 |
| Position: | 1312.9 | Intensity: | 12.236 |
| Position: | 1338.2 | Intensity: | 115.936 |
| Position: | 1390.7 | Intensity: | 14.399 |
| Position: | 1430.2 | Intensity: | 33.921 |
| Position: | 1463.4 | Intensity: | 22.573 |
| Position: | 1486.0 | Intensity: | 7.195 |
| Position: | 1520.5 | Intensity: | 33.708 |
| Position: | 1585.5 | Intensity: | 21.258 |
| Position: | 1628.5 | Intensity: | 27.280 |
| Position: | 2537.6 | Intensity: | 0.355 |
| Position: | 2738.6 | Intensity: | 1.268 |
| Position: | 2842.7 | Intensity: | 10.481 |
| Position: | 2938.7 | Intensity: | 35.252 |
| Position: | 2980.1 | Intensity: | 25.665 |
| Position: | 3007.6 | Intensity: | 10.180 |
| Position: | 3065.6 | Intensity: | 19.538 |
| Position: | 3095.0 | Intensity: | 20.168 |
| Position: | 3106.6 | Intensity: | 13.334 |
| Position: | 3127.2 | Intensity: | 14.441 |

Figure 40:
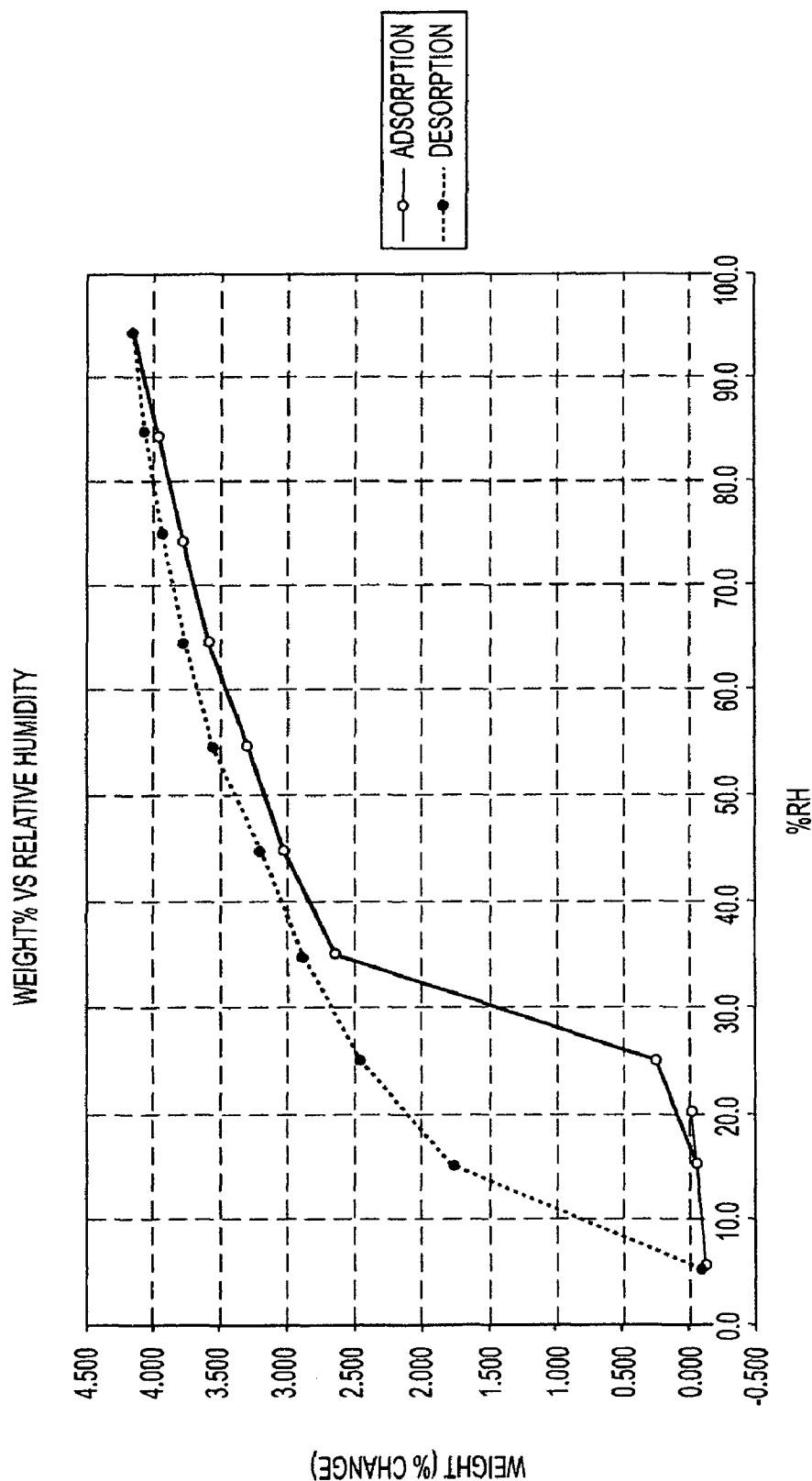
FIG. 40 is the DVS isotherm of racemic ilaprazole, Form I.

FIG. 40 is the DVS isotherm of racemic ilaprazole, Form I. The DVS isotherm shows a 0.1% weight loss at 5% RH, a 4.2% weight gain from 5 to 95% RH, and a 4.2% weight loss from 95 to 5% RH.

Example 5

Preparation of Characterization of Racemic Ilaprazole, Form B

A solution containing 10 mL of acetone was saturated with ilaprazole, Form A by sonicating with excess solids for approximately 5 minutes at ambient temperature. The resulting slurry was filtered through a 0.2 micron nylon filter into a glass vial. The vial was capped and placed into a refrigerator. The resulting white solid was collected by vacuum filtration 11 days later as Form B.

Figure 41:
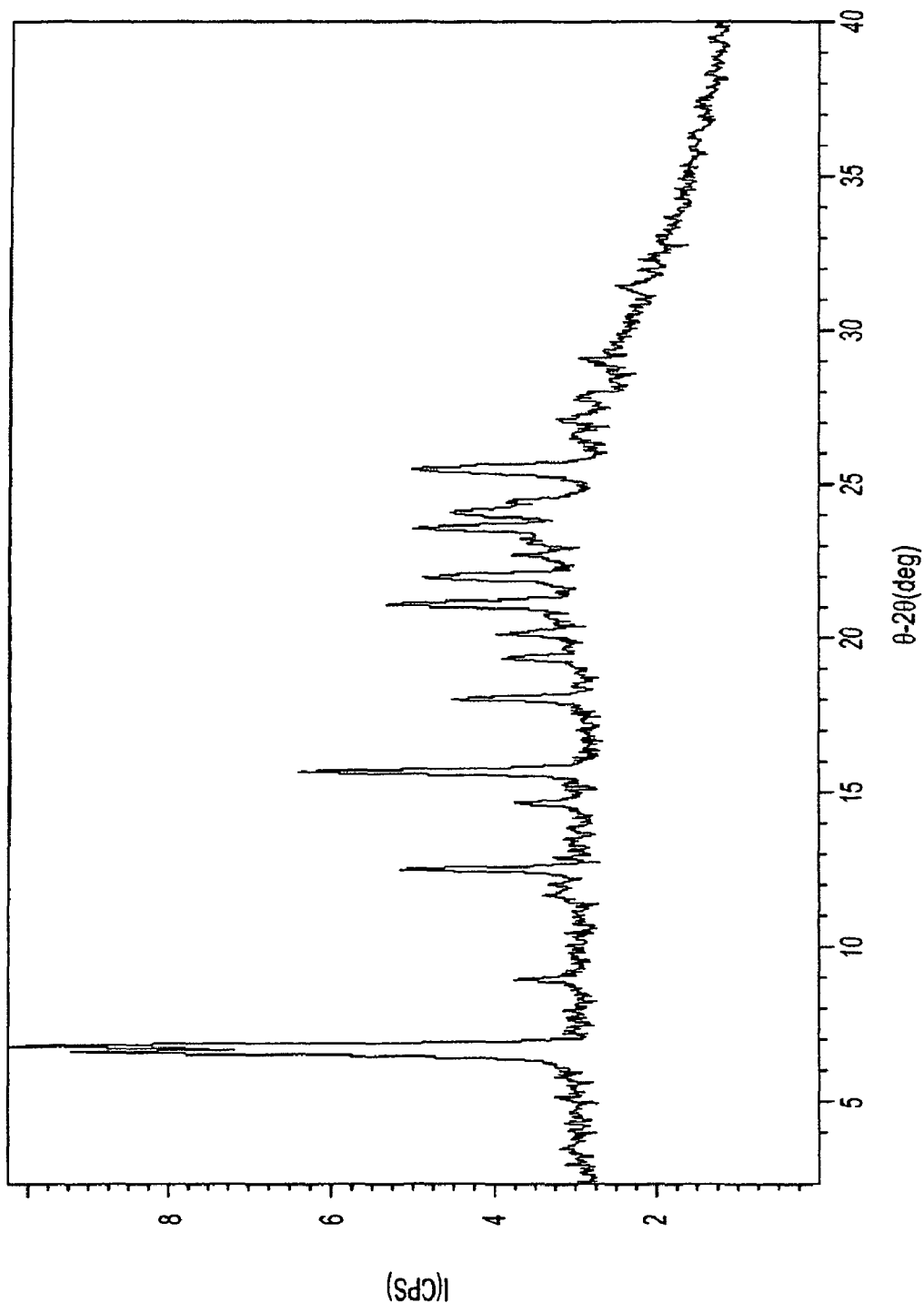
FIG. 41 is the XRPD pattern of racemic ilaprazole, Form B.

The XRPD pattern of racemic ilaprazole, Form B was obtained using an Inel XRG-3000 diffractometer, as described above. The measurement conditions are reported in Table 19. FIG. 41 shows the XRPD pattern for racemic ilaprazole, Form B. Table 20 reports the peaks identified in the XRPD pattern. In its XRPD racemic ilaprazole Form B may be characterized by peaks at 6.8° 2θ±0.2° 2θ; 9.1° 2θ±0.2° 2θ; 22.0° 2θ±0.2° 2θ and 25.5° 2θ±0.2° 2θ. Another characteristic grouping includes peaks at 3.7 2θ±0.2° 2θ; 6.0° 2θ±0.2° 2θ; 6.8 2θ±0.2° 2θ; 9.1 2θ±0.2° 2θ; 12.1 2θ±0.2° 2θ; and 31.4 2θ±0.2° 2θ.

TABLE 19

Measurement Conditions for XRPD Pattern of Racemic Ilaprazole, Form B.

| Measurement Condition: | |
|---|---|
| X-ray tube | |
| target = | Cu |
| voltage = | 40.0 (kV) |
| current = | 30.0 (mA) |
| Slits | |
| divergence slit = | 1.00000 (deg) |
| scatter slit = | 1.00000 (deg) |
| receiving slit = | 0.15000 (mm) |
| Scanning | |
| drive axis = | 2Theta/Theta |
| scan range = | 2.519-39.979 |
| scan mode = | Continuous Scan |
| scan speed = | 0.0040 (deg/min) |
| sampling pitch = | 0.0200 (deg) |
| preset time = | 300.00 (sec) |
| Data Process Condition: | |
| Smoothing | [AUTO] |
| smoothing points = | 23 |
| B.G. Subtraction | [AUTO] |
| sampling points = | 27 |
| repeat times = | 30 |
| Ka1-a2 Separate | [MANUAL] |
| Ka1 a2 ratio = | 50.0 (%) |
| Peak Search | [AUTO] |
| differential points = | 21 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 20

Peak Positions of Ilaprazole, Form B XRPD Pattern

| Peak No. | Position (°2θ ± 0.2 °2θ) | d-spacing | Intensity | $I/I_o^c$ |
|---|---|---|---|---|
| 1 | 3.7 | 23.9 | 44 | 4 |
| 2 | 6.0 | 14.8 | 48 | 4 |
| 3 | 6.8 | 12.9 | 1227 | 100 |
| 4 | 9.1 | 9.7 | 114 | 9 |
| 5 | 11.8 | 7.5 | 73 | 6 |
| 6 | 12.1 | 7.3 | 56 | 5 |
| 7 | 12.6 | 7.0 | 315 | 26 |
| 8 | 14.8 | 6.0 | 114 | 9 |
| 9 | 15.8 | 5.6 | 537 | 44 |
| 10 | 18.1 | 4.9 | 258 | 21 |
| 11 | 19.4 | 5.6 | 156 | 13 |
| 12 | 20.2 | 4.4 | 148 | 12 |
| 13 | 20.7 | 4.3 | 70 | 6 |
| 14 | 21.2 | 4.2 | 413 | 34 |
| 15 | 22.0 | 4.0 | 357 | 29 |
| 16 | 22.7 | 3.9 | 124 | 10 |
| 17 | 23.2 | 3.8 | 133 | 11 |
| 18 | 23.6 | 3.8 | 362 | 30 |
| 19 | 24.1 | 3.7 | 317 | 26 |
| 20 | 24.4 | 3.6 | 177 | 14 |
| 21 | 25.5 | 3.5 | 417 | 34 |
| 22 | 26.7 | 3.3 | 67 | 5 |
| 23 | 27.2 | 3.3 | 101 | 8 |
| 24 | 27.8 | 3.2 | 87 | 7 |
| 25 | 29.1 | 3.1 | 84 | 7 |
| 26 | 31.4 | 2.8 | 66 | 5 |

Figure 42:
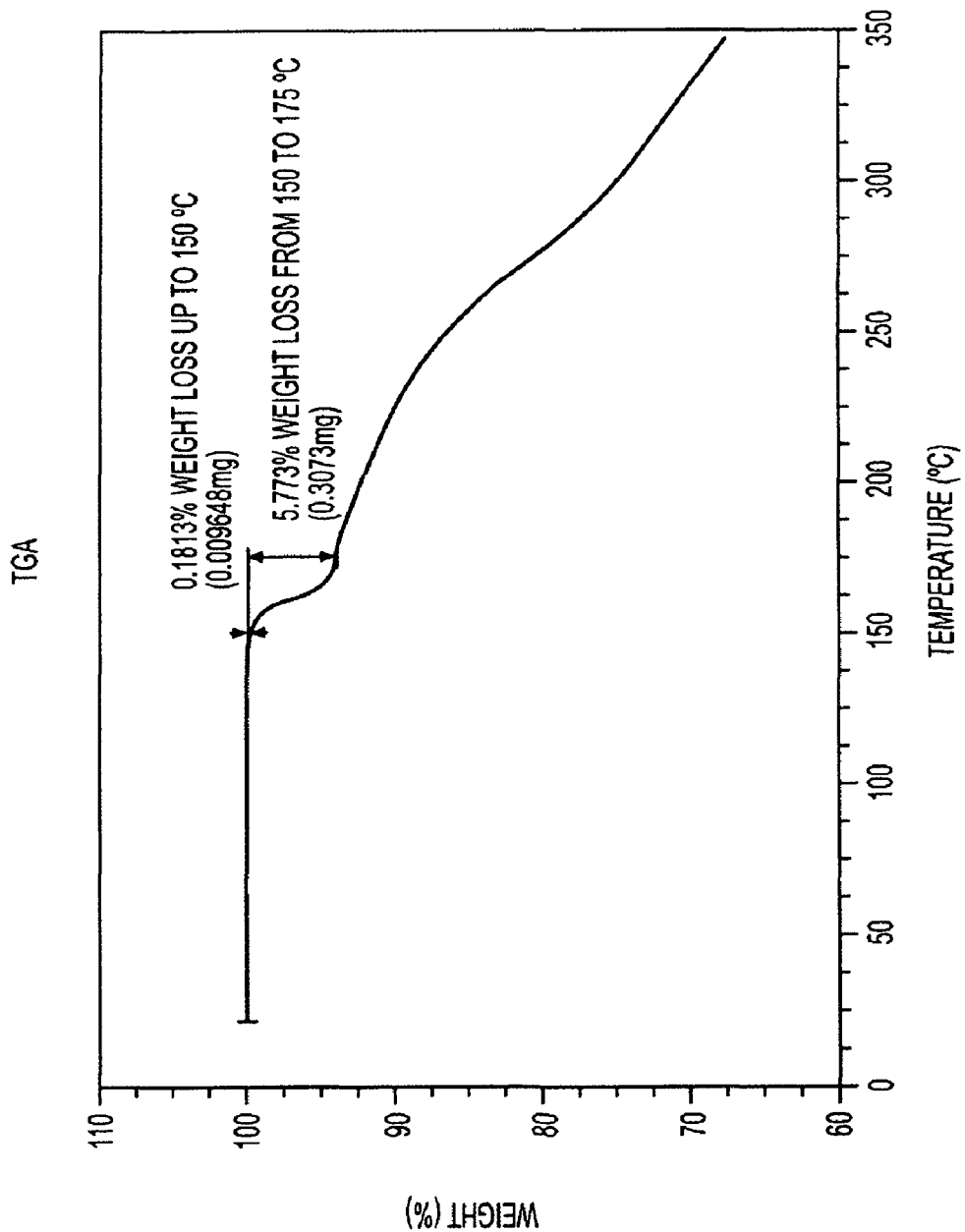
FIG. 42 is the TGA thermogram of racemic ilaprazole, Form B.

FIG. 42 is the TGA thermogram of racemic ilaprazole, Form B. The sample showed a 0.2% weight loss up to 150° C. and 5.8% weight loss between 150 and 175° C.

Figure 43:
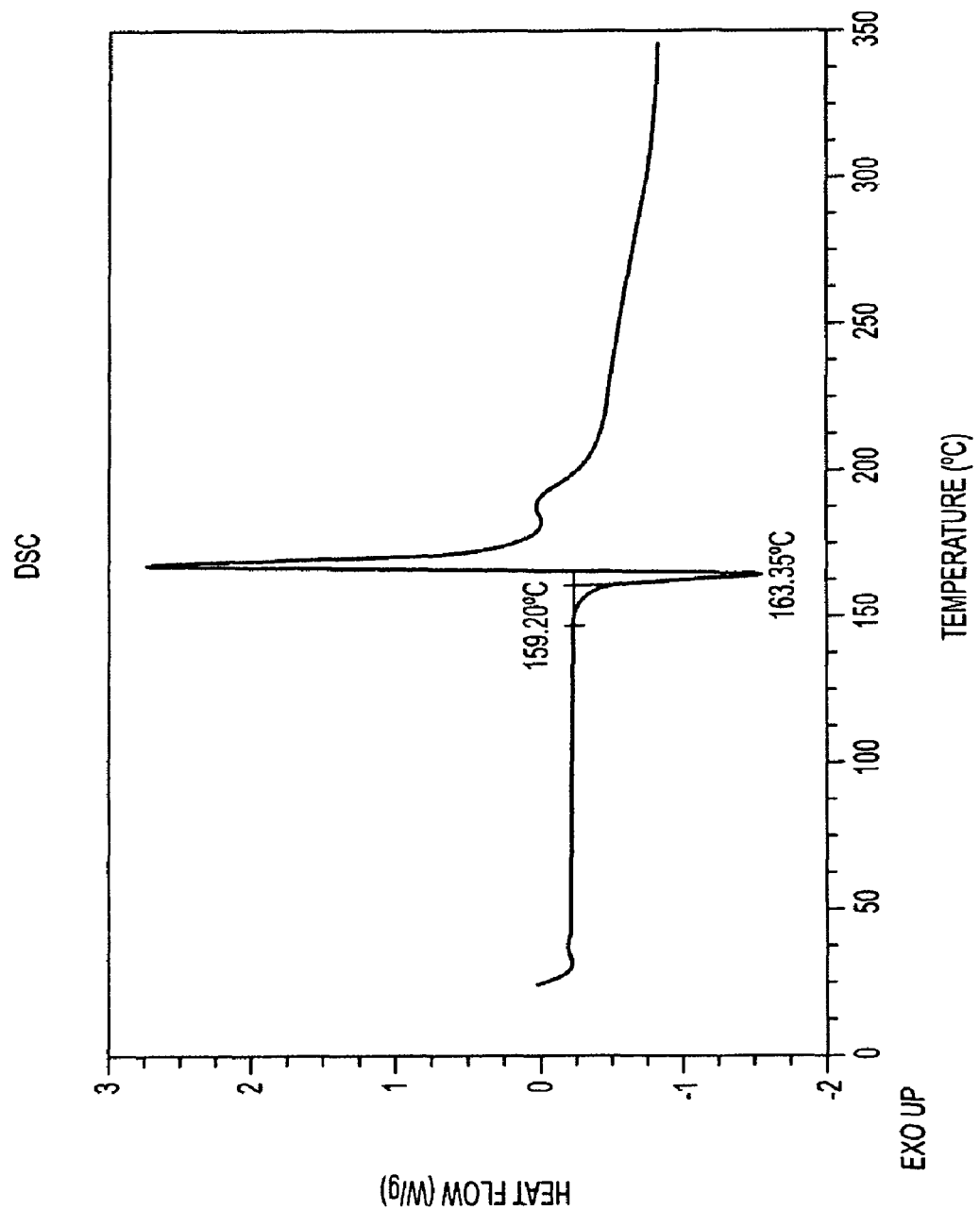
FIG. 43 is the DSC thermogram of racemic ilaprazole, Form B.

FIG. 43 is the DSC thermogram of racemic ilaprazole, Form B. The endotherm onset occurred at 159° C. (max 163° C.).

Figure 44:
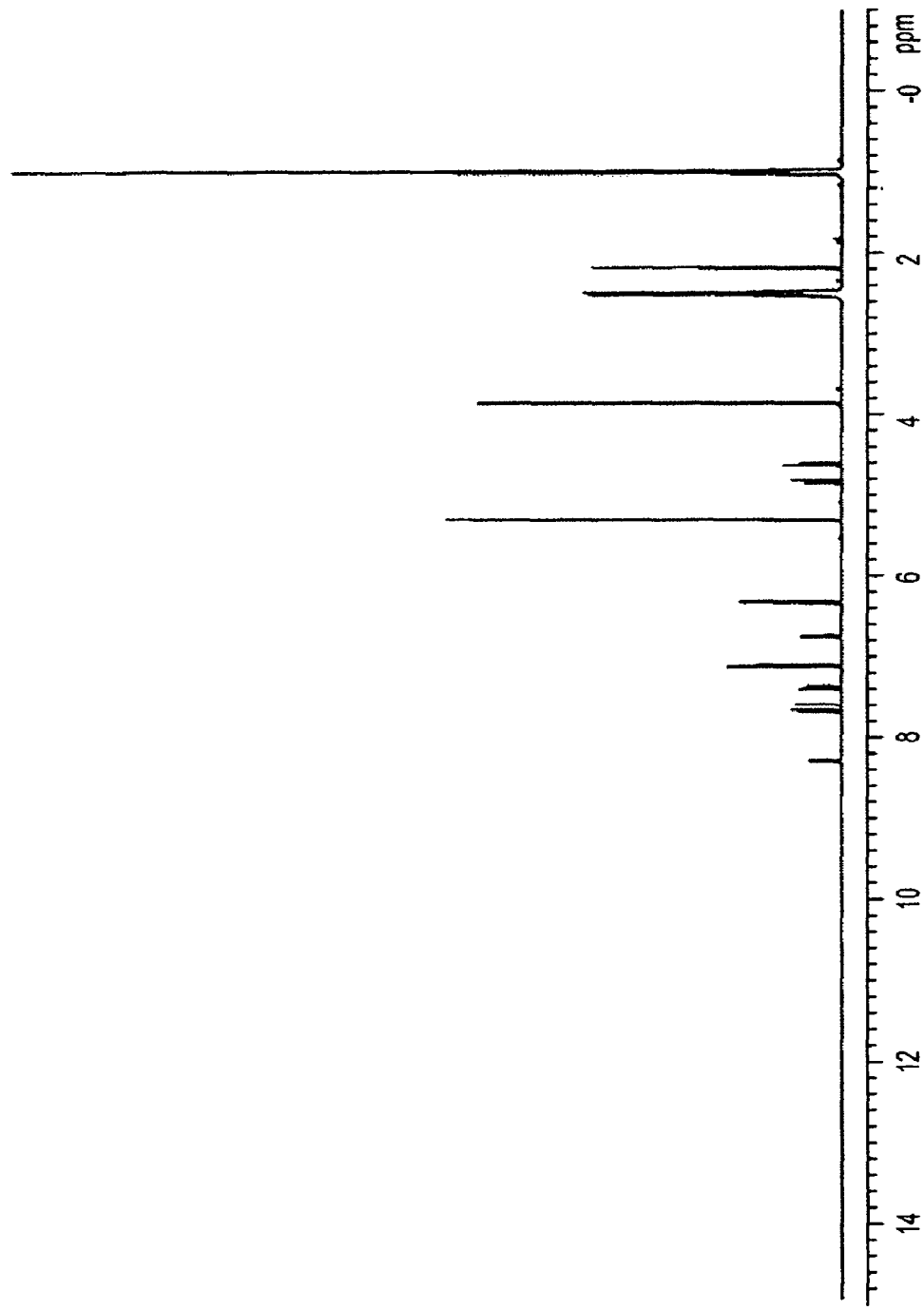
FIG. 44 is the proton NMR spectrum of racemic ilaprazole, Form B.

FIG. 44 is the proton NMR Spectrum of racemic ilaprazole, Form B. Any peaks near 5.32 ppm are due to solvent—not to ilaprazole. Peaks near 1.0 and 2.5 ppm are due to TEA, which is used to stabilize ilaprazole in solution, and not to ilaprazole.

Figure 45:
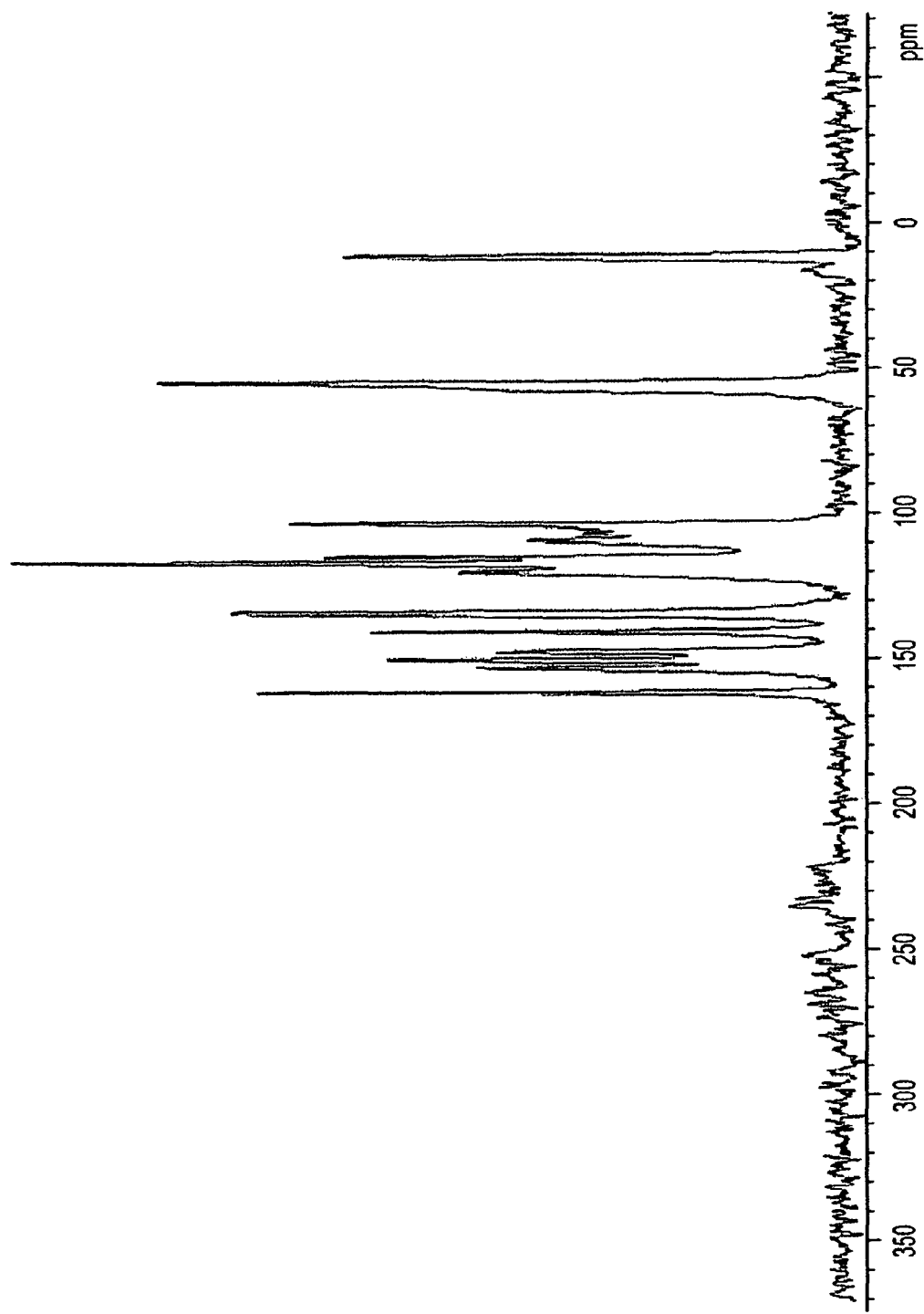
FIG. 45 is the solid state $^{13}$C CP/MAS ssNMR spectrum of ilaprazole, Form B.

FIG. 45 is the solid state $^{13}$C CP/MAS NMR spectrum of racemic ilaprazole, Form B. The spectrum is externally referenced against glycine at 176.5 ppm. The peaks in the solid state $^{13}$C NMR spectrum are reported in Table 21.

TABLE 21

Solid State $^{13}$C NMR Peaks for Racemic Ilaprazole, Form B.

| PPM | HEIGHT |
|---|---|
| 163.5 | 99.8 |
| 155.0 | 62.2 |
| 152.2 | 77.5 |
| 149.5 | 58.7 |
| 142.2 | 80.6 |
| 135.7 | 104.3 |
| 121.5 | 65.4 |
| 118.3 | 141.8 |
| 116.2 | 88.5 |
| 110.3 | 53.5 |
| 107.8 | 44.0 |
| 104.5 | 94.3 |
| 55.7 | 117.1 |
| 11.5 | 85.4 |

Figure 46:
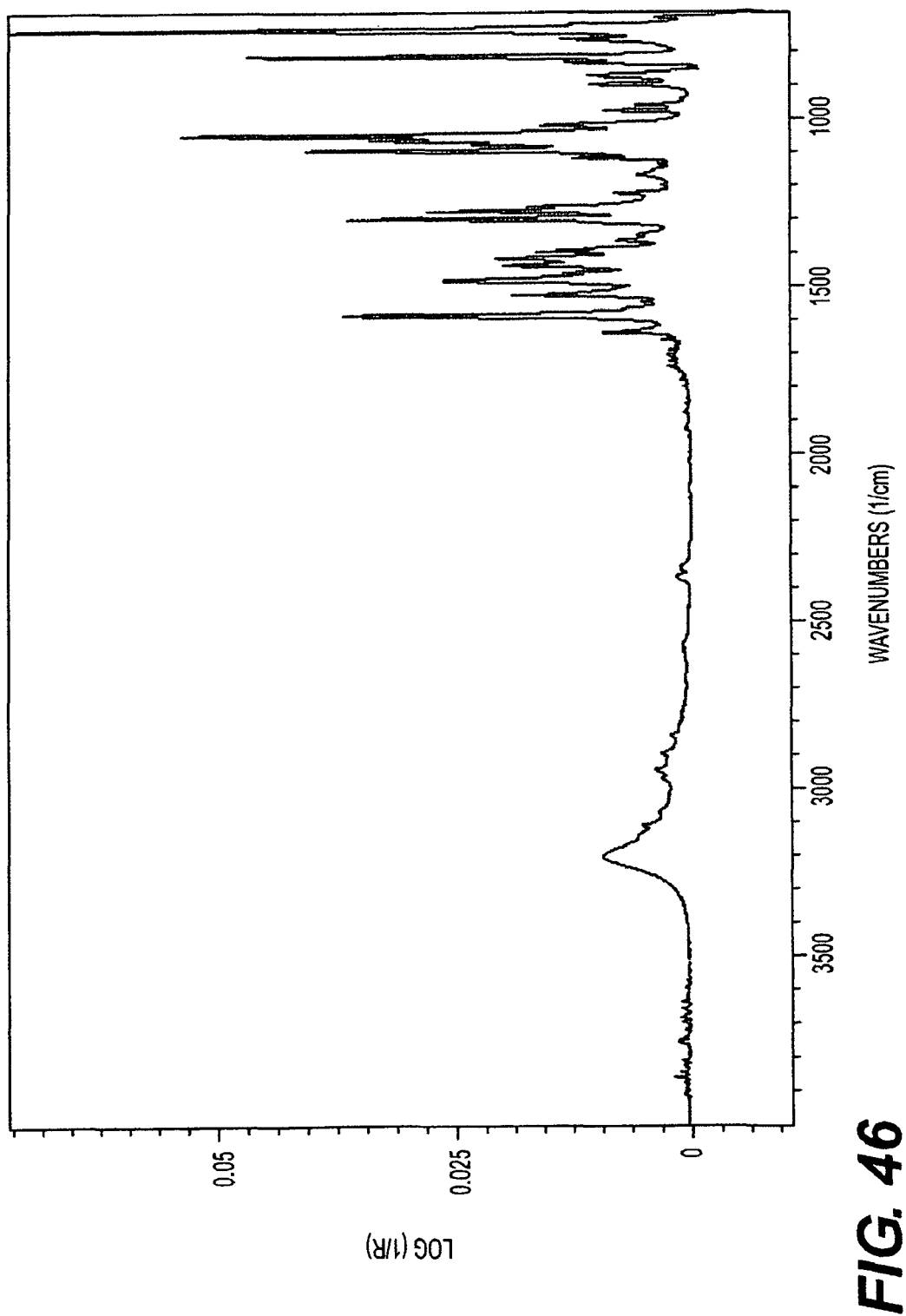
FIG. 46 is the IR spectrum of racemic ilaprazole, Form B.

FIG. 46 is the IR spectrum of racemic ilaprazole, Form B. Table 22 reports the absorbance peaks in the IR spectrum.

TABLE 22

Peaks in IR Spectrum of Racemic Ilaprazole Form B.

| Position: | | Intensity: | |
|---|---|---|---|
| Position: | 715.4 | Intensity: | 0.0125 |
| Position: | 732.2 | Intensity: | 0.0730 |
| Position: | 758.2 | Intensity: | 0.0131 |
| Position: | 810.3 | Intensity: | 0.0464 |
| Position: | 829.0 | Intensity: | 0.0126 |
| Position: | 864.1 | Intensity: | 0.0100 |
| Position: | 892.2 | Intensity: | 0.0101 |
| Position: | 953.4 | Intensity: | 0.0053 |
| Position: | 971.1 | Intensity: | 0.0089 |
| Position: | 1014.2 | Intensity: | 0.0154 |
| Position: | 1043.6 | Intensity: | 0.0534 |
| Position: | 1058.1 | Intensity: | 0.0339 |
| Position: | 1069.6 | Intensity: | 0.0229 |
| Position: | 1088.9 | Intensity: | 0.0406 |
| Position: | 1112.4 | Intensity: | 0.0120 |
| Position: | 1128.3 | Intensity: | 0.0029 |
| Position: | 1162.3 | Intensity: | 0.0051 |
| Position: | 1192.0 | Intensity: | 0.0026 |
| Position: | 1216.2 | Intensity: | 0.0077 |
| Position: | 1256.1 | Intensity: | 0.0173 |
| Position: | 1270.0 | Intensity: | 0.0283 |
| Position: | 1292.8 | Intensity: | 0.0366 |
| Position: | 1339.6 | Intensity: | 0.0051 |
| Position: | 1357.2 | Intensity: | 0.0073 |
| Position: | 1382.1 | Intensity: | 0.0107 |
| Position: | 1389.9 | Intensity: | 0.0161 |
| Position: | 1410.2 | Intensity: | 0.0205 |
| Position: | 1431.3 | Intensity: | 0.0194 |
| Position: | 1454.8 | Intensity: | 0.0124 |
| Position: | 1476.5 | Intensity: | 0.0258 |
| Position: | 1519.9 | Intensity: | 0.0179 |
| Position: | 1580.4 | Intensity: | 0.0368 |
| Position: | 1632.4 | Intensity: | 0.0088 |
| Position: | 1651.4 | Intensity: | 0.00090 |
| Position: | 1695.3 | Intensity: | 0.0011 |
| Position: | 1717.0 | Intensity: | 0.00097 |
| Position: | 2561.9 | Intensity: | 0.00043 |

TABLE 22-continued

Peaks in IR Spectrum of Racemic Ilaprazole Form B.

| Position: | 2835.2 | Intensity: | 0.0018 |
|---|---|---|---|
| Position: | 2888.8 | Intensity: | 0.0028 |
| Position: | 2937.5 | Intensity: | 0.0035 |
| Position: | 2964.4 | Intensity: | 0.0028 |
| Position: | 3062.7 | Intensity: | 0.0031 |
| Position: | 3103.4 | Intensity: | 0.0047 |
| Position: | 3197.1 | Intensity: | 0.0090 |

Figure 47:
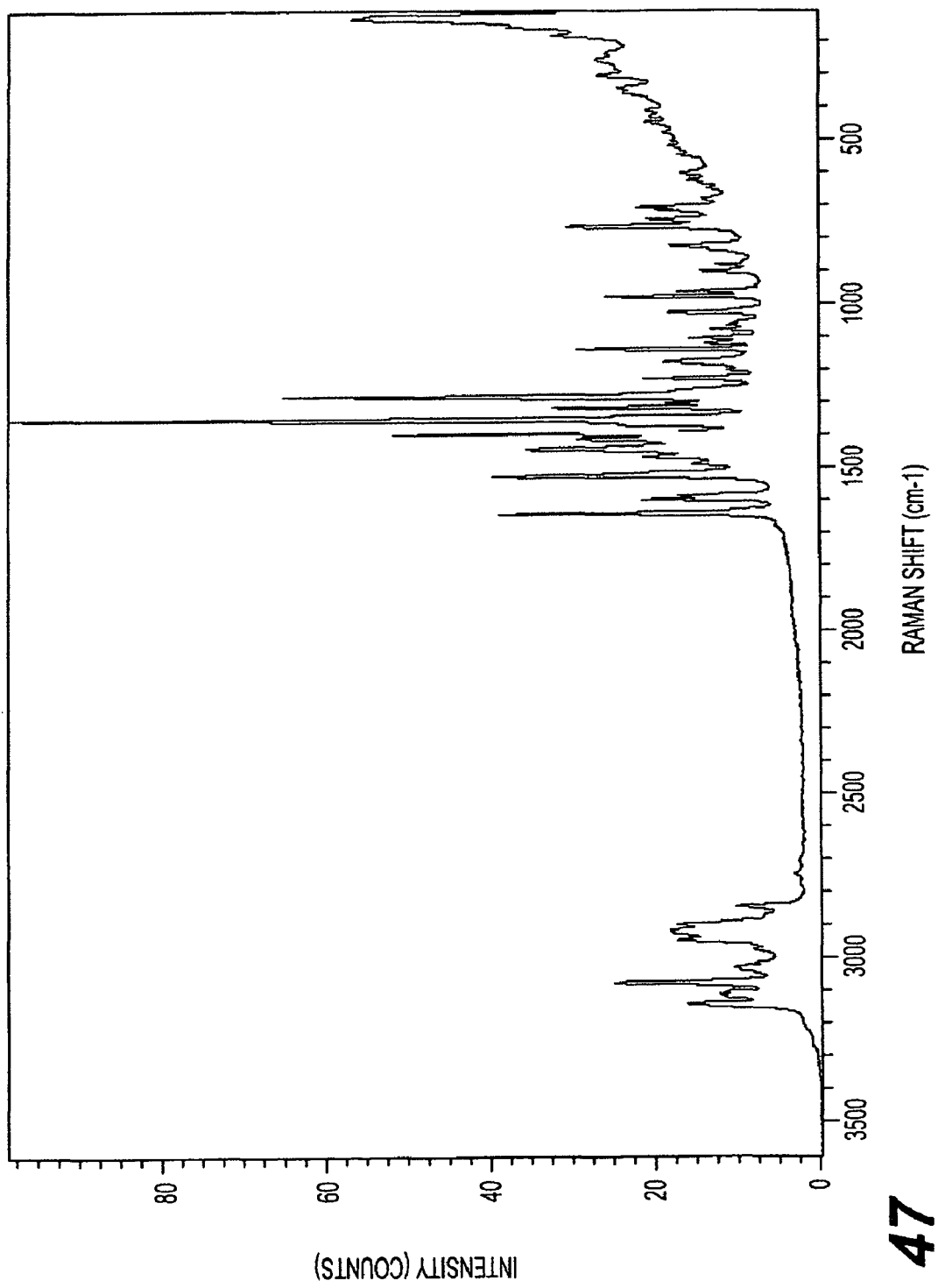
FIG. 47 is the RAMAN spectrum of racemic ilaprazole, Form B.

FIG. 47 is the RAMAN spectrum of racemic ilaprazole, Form B. Table 23 reports the absorbance peaks in the Raman spectrum.

TABLE 23

Peaks in the Raman Spectrum of Racemic Ilaprazole, Form B.

| Position: | 402.3 | Intensity: | 3.360 |
|---|---|---|---|
| Position: | 419.7 | Intensity: | 3.450 |
| Position: | 437.4 | Intensity: | 4.555 |
| Position: | 469.0 | Intensity: | 3.223 |
| Position: | 492.9 | Intensity: | 2.746 |
| Position: | 510.3 | Intensity: | 3.524 |
| Position: | 536.4 | Intensity: | 2.993 |
| Position: | 593.1 | Intensity: | 3.826 |
| Position: | 612.8 | Intensity: | 3.449 |
| Position: | 623.2 | Intensity: | 2.192 |
| Position: | 638.2 | Intensity: | 1.651 |
| Position: | 669.8 | Intensity: | 2.705 |
| Position: | 694.0 | Intensity: | 11.100 |
| Position: | 704.1 | Intensity: | 9.112 |
| Position: | 732.1 | Intensity: | 10.557 |
| Position: | 754.1 | Intensity: | 20.453 |
| Position: | 816.5 | Intensity: | 9.149 |
| Position: | 828.4 | Intensity: | 4.623 |
| Position: | 874.1 | Intensity: | 4.017 |
| Position: | 893.0 | Intensity: | 6.371 |
| Position: | 954.1 | Intensity: | 10.071 |
| Position: | 969.7 | Intensity: | 18.993 |
| Position: | 1015.6 | Intensity: | 12.072 |
| Position: | 1045.9 | Intensity: | 4.196 |
| Position: | 1055.6 | Intensity: | 5.091 |
| Position: | 1068.8 | Intensity: | 6.913 |
| Position: | 1094.8 | Intensity: | 9.593 |
| Position: | 1110.4 | Intensity: | 7.641 |
| Position: | 1128.3 | Intensity: | 23.427 |
| Position: | 1166.2 | Intensity: | 13.097 |
| Position: | 1192.1 | Intensity: | 5.552 |
| Position: | 1216.8 | Intensity: | 15.624 |
| Position: | 1271.3 | Intensity: | 59.718 |
| Position: | 1292.5 | Intensity: | 13.415 |
| Position: | 1306.1 | Intensity: | 27.370 |
| Position: | 1340.8 | Intensity: | 93.661 |
| Position: | 1390.2 | Intensity: | 46.334 |
| Position: | 1406.0 | Intensity: | 24.397 |
| Position: | 1436.3 | Intensity: | 30.633 |
| Position: | 1460.1 | Intensity: | 16.408 |
| Position: | 1482.5 | Intensity: | 10.635 |
| Position: | 1518.8 | Intensity: | 35.366 |
| Position: | 1579.7 | Intensity: | 12.771 |
| Position: | 1590.8 | Intensity: | 17.002 |
| Position: | 1633.4 | Intensity: | 34.488 |
| Position: | 2737.0 | Intensity: | 1.265 |
| Position: | 2835.7 | Intensity: | 8.761 |
| Position: | 2890.1 | Intensity: | 15.700 |
| Position: | 2907.8 | Intensity: | 16.669 |
| Position: | 2936.8 | Intensity: | 15.868 |
| Position: | 2964.3 | Intensity: | 6.875 |
| Position: | 3006.0 | Intensity: | 6.752 |
| Position: | 3019.8 | Intensity: | 9.329 |
| Position: | 3065.1 | Intensity: | 24.167 |
| Position: | 3093.7 | Intensity: | 10.661 |
| Position: | 3101.4 | Intensity: | 11.283 |
| Position: | 3130.5 | Intensity: | 15.490 |

Figure 48:
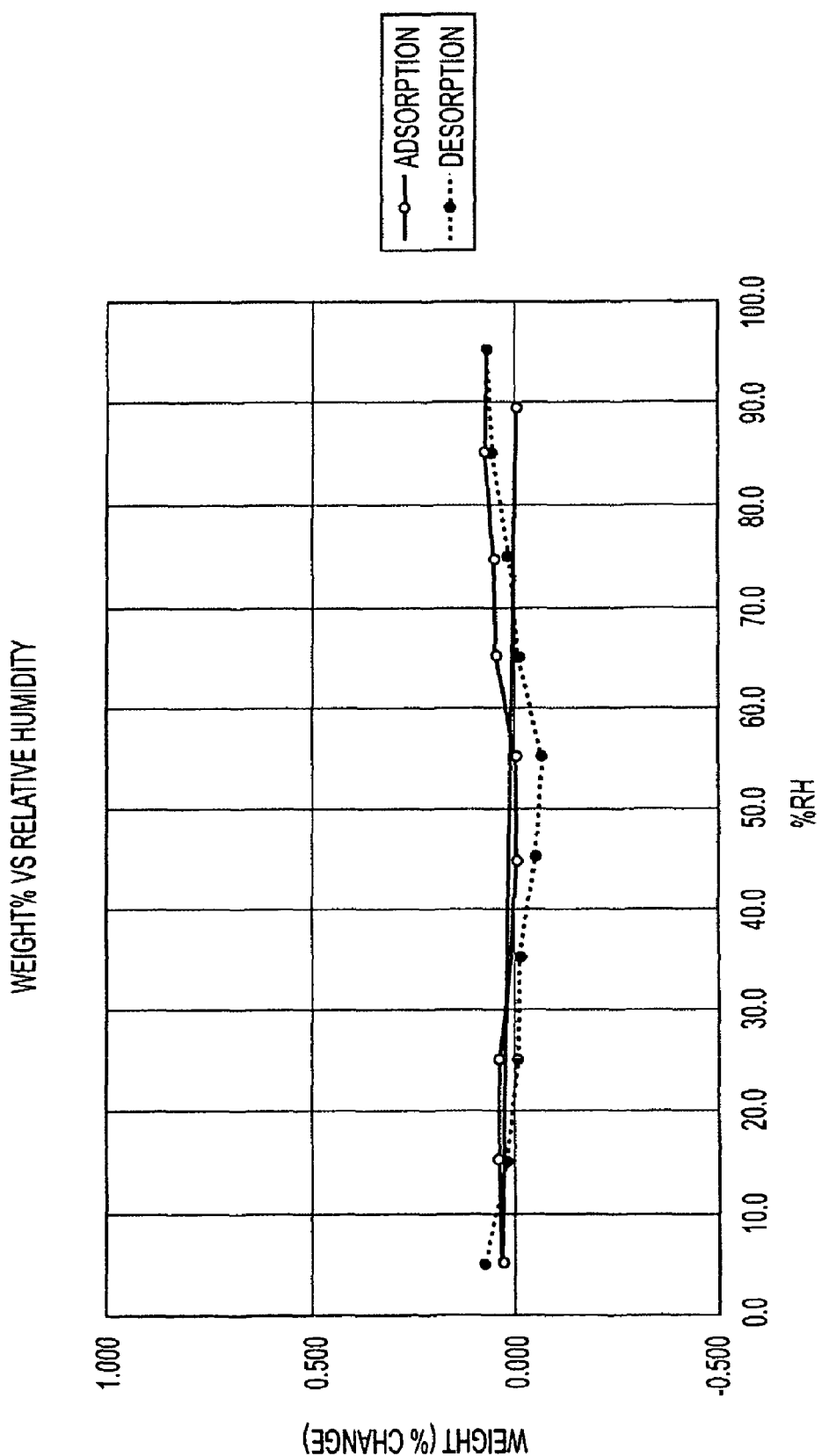
FIG. 48 is the DVS isotherm of racemic ilaprazole, Form B.

FIG. 48 is the DVS isotherm of racemic ilaprazole, Form B. The DVS isotherm shows a 0.03% weight loss at 5% RH, a 0.04% weight gain from 5 to 95% RH, and a 0.00% weight loss from 95 to 5% RH.

Example 6

Ilaprazole Solubility Studies

The solubility of racemic ilaprazole, Forms A, B, and F, were analyzed by exposing them to various ethanol solutions having various pHs for 1 hour. Duplicate analysis was performed for each sample on a second day. The solubility in 100% ethanol (with no pH adjustment) is shown in the first column. Various other aqueous solutions (87.5%, 75%, 62.5%, and 50% ethanol) with varying apparent pHs (7, 8, 9, 10, and 11) were also evaluated. All of the values below are the average of two duplicate preparations analyzed on different days. The results are shown in Table 24.

TABLE 24

Solubility of racemic ilaprazole Forms A, B, and F in various ethanol solutions

| Form | Solubility (mg/mL) | 100% | 87.50% | Ethanol 75% | 62.50% | 50% |
|---|---|---|---|---|---|---|
| A | pH 7  | 6.47 |       | 13.13 |       | 2.80 |
|   | pH 8  | 6.47 | 15.18 |       | 7.18  |      |
|   | pH 9  | 6.47 |       | 14.94 |       | 3.99 |
|   | pH 10 | 6.47 | 18.15 |       | 9.48  |      |
|   | pH 11 | 6.47 |       | 16.25 |       | 6.21 |
| B | pH 7  | 8.38 |       | 18.86 |       | 3.62 |
|   | pH 8  | 8.38 | 21.65 |       | 9.56  |      |
|   | pH 9  | 8.38 |       | 20.61 |       | 4.73 |
|   | pH 10 | 8.38 | 24.35 |       | 11.86 |      |
|   | pH 11 | 8.38 |       | 22.34 |       | 7.27 |
| F | pH 7  | 7.04 |       | 14.82 |       | 2.73 |
|   | pH 8  | 7.04 | 17.83 |       | 7.43  |      |
|   | pH 9  | 7.04 |       | 16.11 |       | 3.54 |
|   | pH 10 | 7.04 | 20.25 |       | 9.51  |      |
|   | pH 11 | 7.04 |       | 18.01 |       | 5.79 |

The solubility of ilaprazole, Forms A, B, and F, were analyzed by exposing them to 90% ethanol solutions of various pHs for 1 hour. The analysis was repeated a second time to check the reproducibility of the results. The results are shown in Table 25.

TABLE 25

Solubility of racemic ilaprazole, Forms A and F, in various pH environments

| From | Solubility (mg/mL) | 7.0 | 7.5 | 8.0 | 8.5 | pH 9.0 | 9.5 | 10.0 | 10.5 | 11.0 |
|---|---|---|---|---|---|---|---|---|---|---|
| A | Day 1   | 14.82 | 15.27 | 15.51 | 16.05 | 16.99 | 17.66 | 18.30 | 18.47 | 17.63 |
|   | Day 2   | 15.77 | 15.45 | 15.90 | 16.66 | 17.66 | 19.30 | 19.79 | 19.85 | 19.22 |
|   | Average | 15.30 | 45.36 | 15.71 | 16.36 | 17.33 | 18.48 | 19.05 | 19.16 | 18.43 |
|   | % Diff. | 6.41  | 1.18  | 2.51  | 3.80  | 3.94  | 9.29  | 8.14  | 7.47  | 9.02  |
| B | Day 1   | 19.16 | 20.37 | 20.28 | 20.90 | 21.73 | 22.79 | 23.19 | 23.43 | 21.59 |
|   | Day 2   | 20.91 | 19.66 | 20.00 | 21.56 | 22.06 | 24.20 | 24.15 | 24.66 | 24.89 |
|   | Average | 20.04 | 20.02 | 20.14 | 21.23 | 21.90 | 23.50 | 23.67 | 24.05 | 23.24 |
|   | % Diff. | 9.13  | 3.49  | 1.38  | 3.16  | 1.52  | 6.19  | 4.14  | 5.25  | 15.28 |
| F | Day 1   | 16.37 | 16.89 | 17.25 | 17.71 | 18.32 | 19.66 | 20.02 | 20.28 | 19.47 |
|   | Day 2   | 16.89 | 16.75 | 16.84 | 17.66 | 18.70 | 20.25 | 20.66 | 20.94 | 20.35 |
|   | Average | 16.63 | 16.82 | 17.05 | 17.69 | 18.51 | 19.96 | 20.34 | 20.61 | 19.91 |
|   | % Diff. | 3.18  | 0.83  | 2.38  | 0.28  | 2.07  | 3.00  | 3.20  | 3.25  | 4.52  |

Example 7

Preparation of Characterization of Racemic Ilaprazole, Form E

Approximately 82.0 mg Ilaprazole, Form A was added to a solution containing 6 mL MeOH and 6 µL triethylamine. The solid was dissolved using sonication. The solution was filtered through a 0.2 micron nylon filter into a glass vial. The vial opening was covered with aluminum foil containing five pinholes and left to evaporate at ambient temperature. A dark green solid resulted approximately 6 days later and was identified as Form E.

Figure 49:
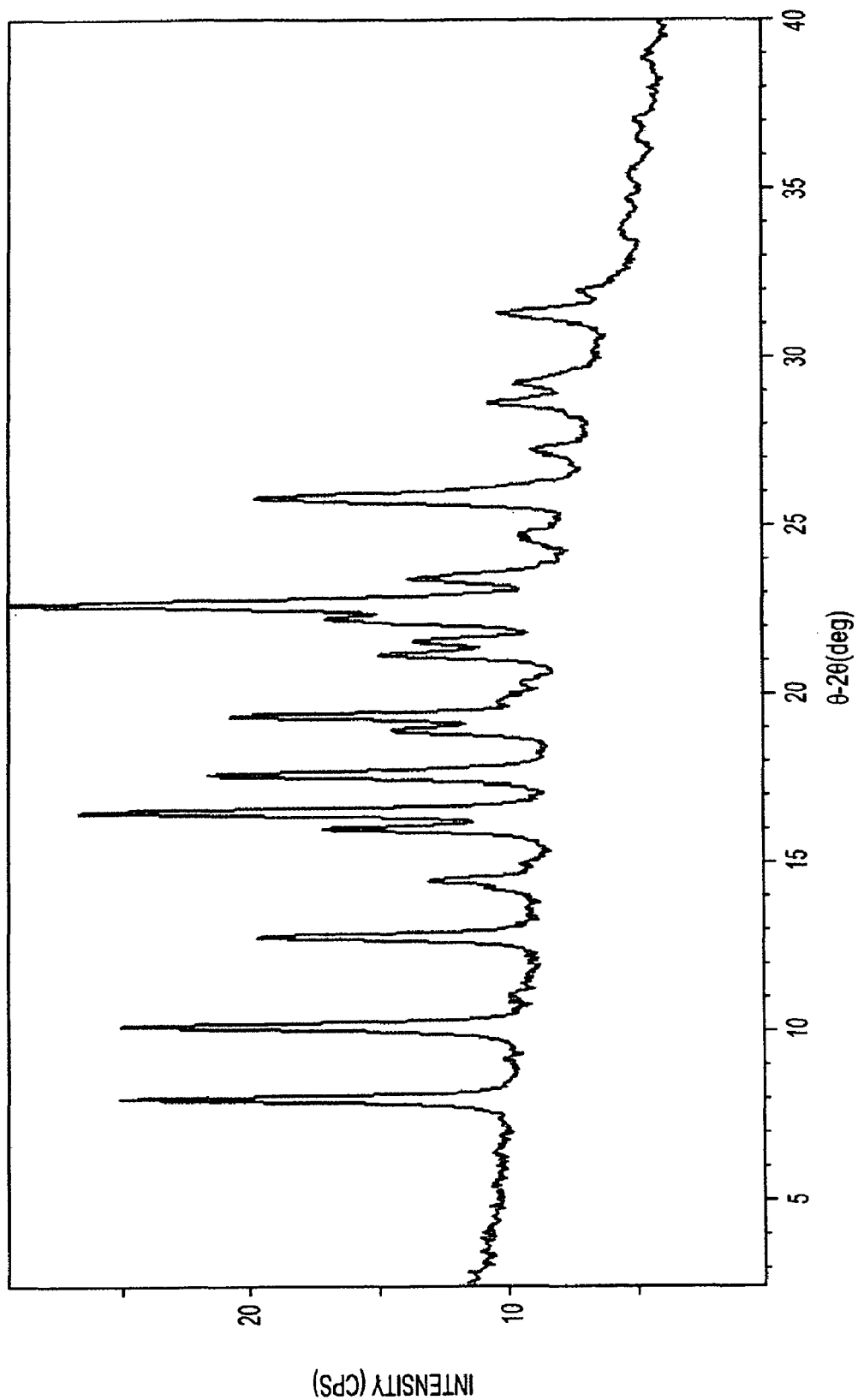
FIG. 49 is the XRPD pattern of racemic ilaprazole, Form E.

The XRPD pattern of racemic ilaprazole, Form E was obtained using an Inel XRG-3000 diffractometer. The measurement conditions are reported in Table 26. FIG. 49 shows the XRPD pattern for racemic ilaprazole, Form E. Table 27 reports the peaks identified in the XRPD pattern. In its XRPD racemic ilaprazole, Form E may be characterized by peaks at 8.1° 2θ±0.2° 2θ; 10.1° 2θ±0.2° 2θ; and 12.8° 2θ±0.2° 2θ. Another characteristic grouping includes the peak at 31.1° 2θ±0.2° 2θ.

TABLE 26

Measurement Conditions for XRPD Pattern of Racemic Ilaprazole, Form E.

| Measurement Condition: | |
|---|---|
| X-ray tube | |
| target = | Cu |
| voltage = | 40.0 (kV) |
| current = | 30.0 (mA) |
| Slits | |
| divergence slit = | 1.00000 (deg) |
| scatter slit = | 1.00000 (deg) |
| receiving slit = | 0.15000 (mm) |
| Scanning | |
| drive axis = | 2Theta/Theta |
| scan range = | 2.519-39.979 |
| scan mode = | Continuous Scan |
| scan speed = | 0.0040 (deg/min) |
| sampling pitch = | 0.0200 (deg) |
| preset time = | 300.00 (sec) |

TABLE 26-continued

Measurement Conditions for XRPD Pattern of Racemic Ilaprazole, Form E.

Data Process Condition:

| | |
|---|---|
| Smoothing | [AUTO] |
| smoothing points = | 57 |
| B.G. Subtraction | [AUTO] |
| sampling points = | 27 |
| repeat times = | 30 |
| Kα1-α2 Separate | [MANUAL] |
| Kα1 α2 ratio = | 50.0 (%) |
| Peak Search | [AUTO] |
| differential points = | 35 |
| FWHM threshold = | 0.050 (deg) |
| intensity threshold = | 30 (par mil) |
| FWHM ratio (n − 1)/n = | 2 |
| System Error Correction: | [NO] |
| Precise Peak Correction: | [NO] |

TABLE 27

Peak Positions of Ilaprazole, Form E XRPD Pattern

| Position (°2θ ± 0.20 °2θ) | Relative Intensity |
|---|---|
| 8.0 | 85 |
| 10.2 | 84 |
| 12.8 | 67 |
| 14.5 | 43 |
| 16.0 | 58 |
| 16.5 | 88 |
| 17.6 | 73 |
| 18.9 | 48 |
| 19.3 | 70 |
| 21.2 | 49 |
| 21.6 | 46 |
| 22.2 | 57 |
| 22.7 | 100 |
| 23.4 | 45 |
| 24.7 | 32 |
| 25.8 | 67 |
| 27.2 | 30 |
| 28.7 | 36 |
| 29.2 | 32 |
| 31.3 | 35 |
| 31.9 | 24 |
| 33.7 | 19 |
| 34.7 | 18 |
| 35.4 | 18 |
| 37.0 | 17 |
| 38.8 | 16 |

Figure 50:
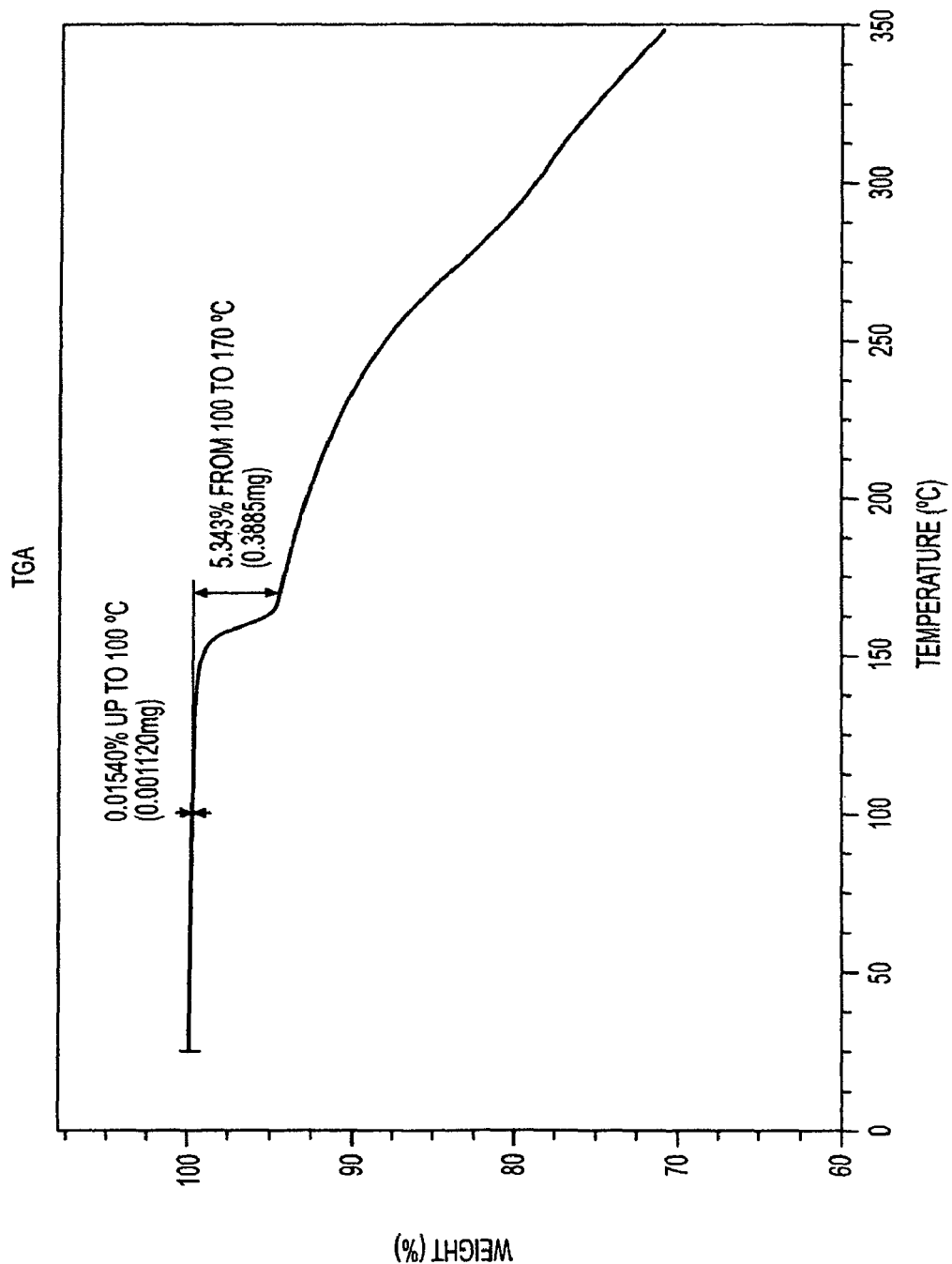
FIG. 50 is the TGA thermogram of racemic ilaprazole, Form E.

FIG. 50 is the TGA thermogram of ilaprazole, Form E. The TG curve shows a negligible weight loss (<0.02%) up to 100° C., indicating the material is unsolvated. A weight loss of 5.3% is observed from 100 to 170° C., mostly like due to decomposition.

Figure 51:
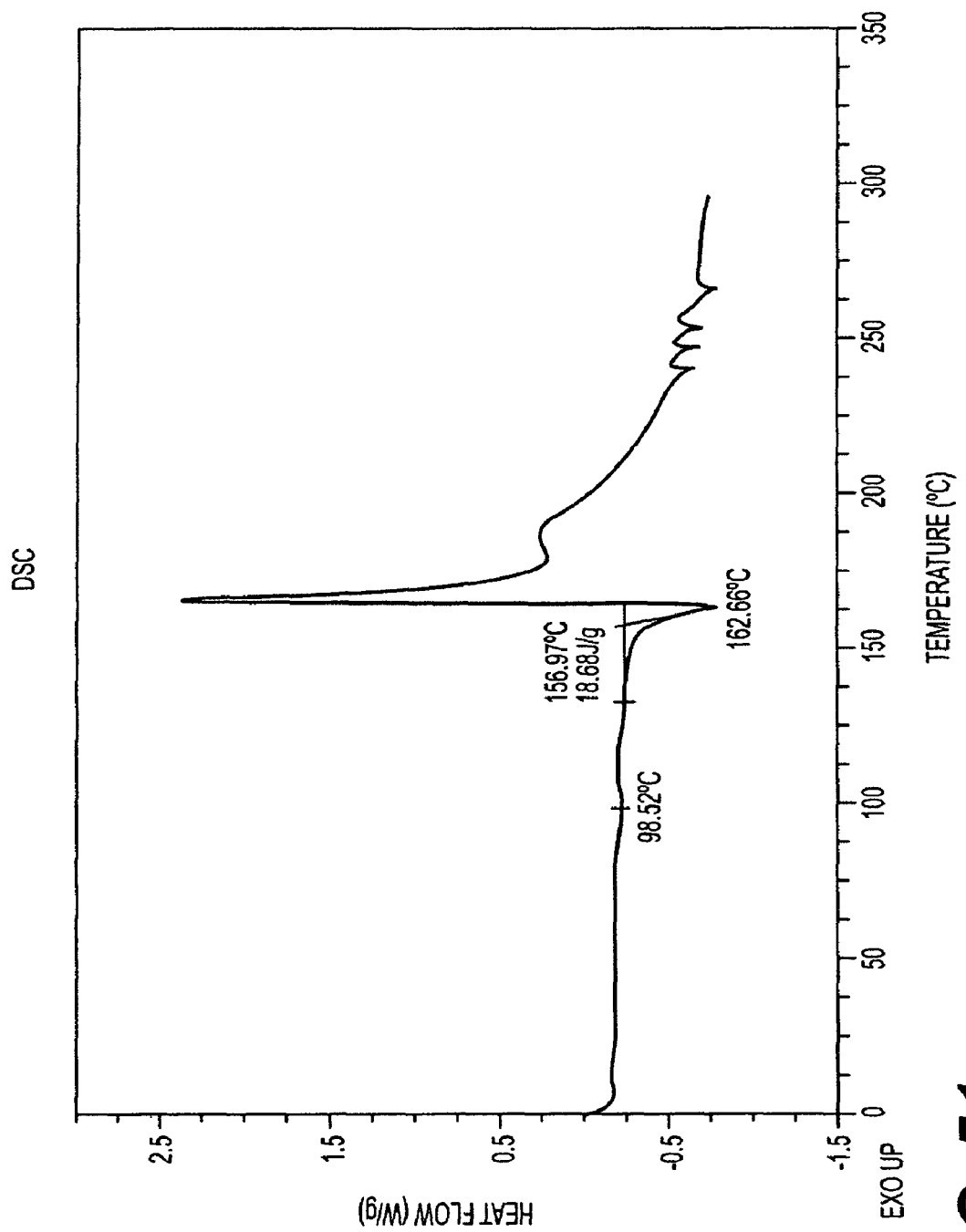
FIG. 51 is the DSC thermogram of racemic ilaprazole, Form E.

FIG. 51 is the DSC thermogram of racemic ilaprazole, Form F. Form E exhibits a minor endotherm near 99° C., and an endotherm near 163° C. (onset. 157° C.) followed immediately by a sharp exotherm. The nature of the minor endotherm was not investigated. The remaining DSC events are most likely due to concomitant melt and decomposition.

Figure 52:
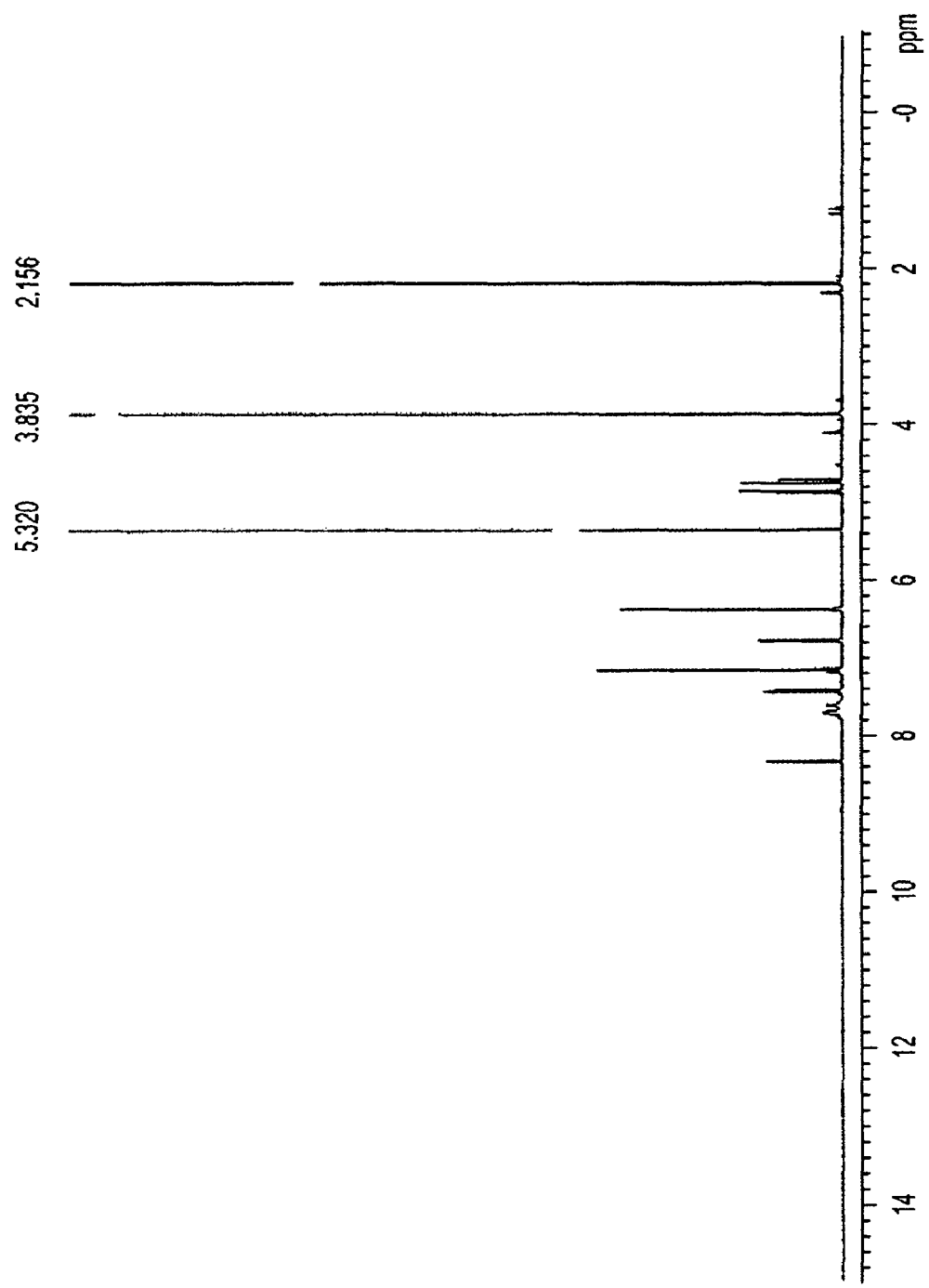
FIG. 52 is the proton NMR spectrum of racemic ilaprazole, Form E.

FIG. 52 is the $^1$H NMR spectra of racemic ilaprazole, Form E, in $CD_2Cl_2$. Any peaks near 5.32 ppm are due to solvent—not to ilaprazole.

Figure 53:
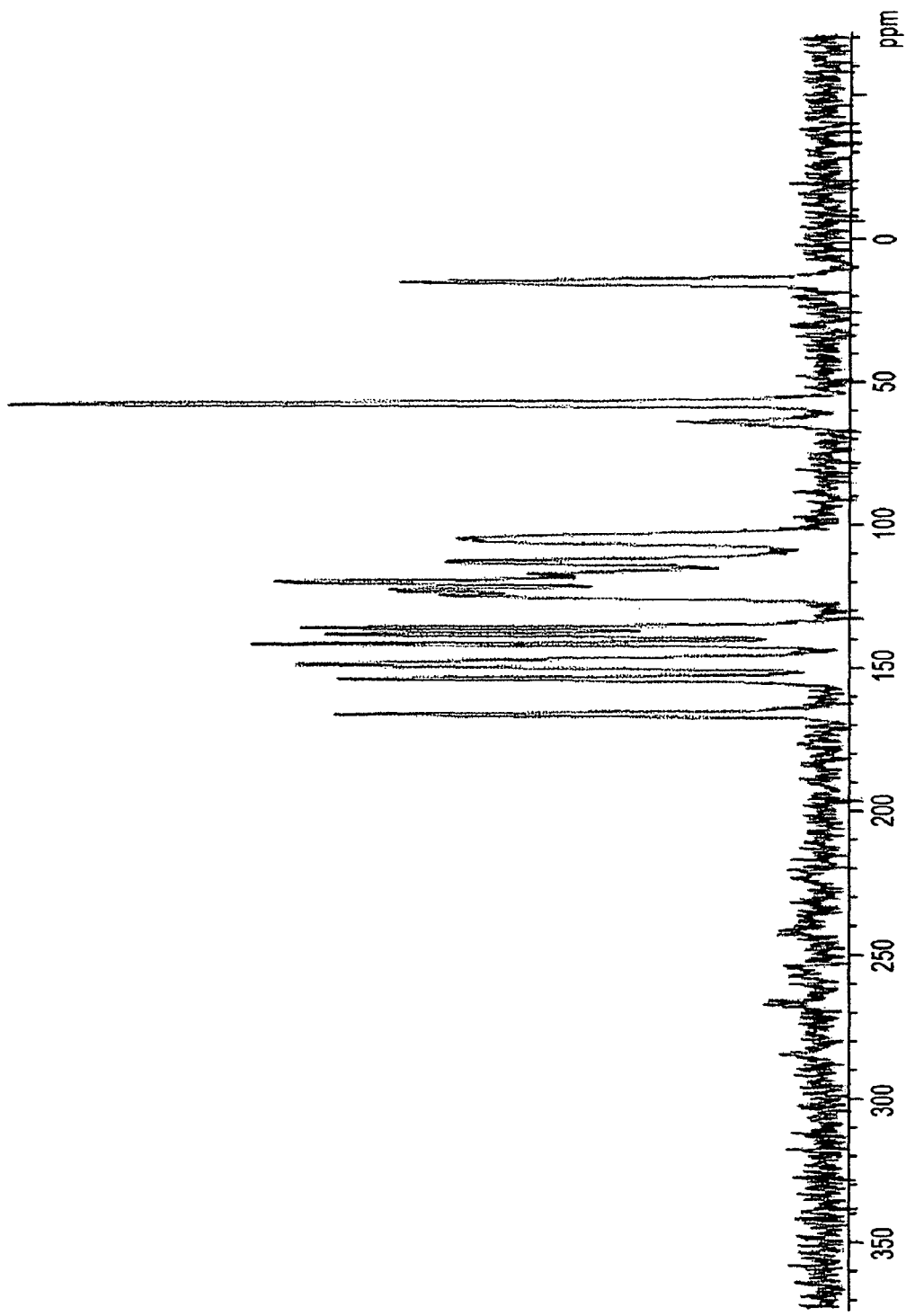
FIG. 53 is the solid state $^{13}$C CP/MAS ssNMR spectrum of racemic ilaprazole, Form E.

FIG. 53 is the solid state $^{13}$C CP/MAS NMR spectrum of racemic ilaprazole, Form E. The spectrum is externally referenced against glycine at 176.5 ppm. The peaks positions in the solid state $^{13}$C NMR spectrum are reported in Table 28, rounded to the nearest 0.1 ppm. The peak occurring at 62.4 may overlap with excipient peaks.

TABLE 28

Solid State $^{13}$C NMR Peaks for Racemic Ilaprazole, Form E.

| PPM | HEIGHT |
|---|---|
| 165.7 | 85.1 |
| 153.2 | 84.6 |
| 148.0 | 91.7 |
| 141.2 | 99.3 |
| 137.7 | 86.6 |
| 135.4 | 90.9 |
| 123.9 | 67.3 |
| 122.0 | 75.8 |
| 119.0 | 95.2 |
| 117.0 | 49.5 |
| 116.2 | 51.5 |
| 112.2 | 66.2 |
| 103.6 | 64.3 |
| 62.4 | 25.8 |
| 56.4 | 141.8 |
| 13.2 | 74.1 |

Figure 54:
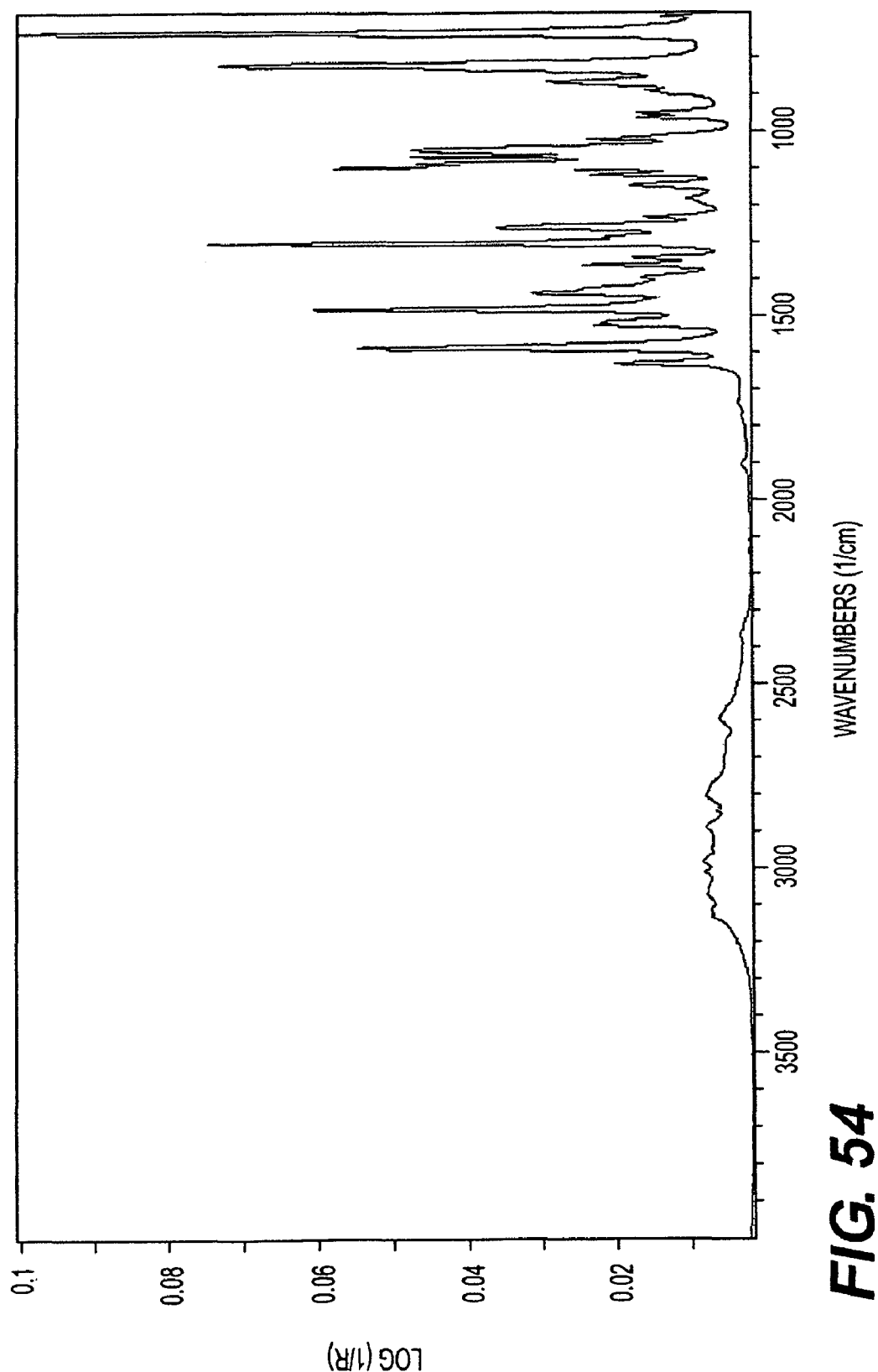
FIG. 54 is the IR spectrum of racemic ilaprazole, Form E.

FIG. 54 shows the IR spectrum of racemic ilaprazole, Form E. The IR peaks are listed in Table 29.

TABLE 29

Peak Positions of Ilaprazole, Form E IR Spectrum. Position (cm$^{-1}$ ± 4 cm$^{-1}$)

| |
|---|
| 688 |
| 732 |
| 756 |
| 823 |
| 866 |
| 890 |
| 950 |
| 963 |
| 1019 |
| 1046 |
| 1054 |
| 1066 |
| 1083 |
| 1095 |
| 1119 |
| 1147 |
| 1182 |
| 1232 |
| 1259 |
| 1285 |
| 1300 |
| 1339 |
| 1359 |
| 1392 |
| 1434 |
| 1482 |
| 1517 |
| 1525 |
| 1585 |
| 1629 |
| 1733 |
| 1905 |
| 2363 |
| 2594 |
| 2800 |
| 2840 |
| 2889 |
| 2980 |
| 3008 |
| 3068 |
| 3128 |

Example 8

Delayed Release Tablet Formulations

Figure 55:
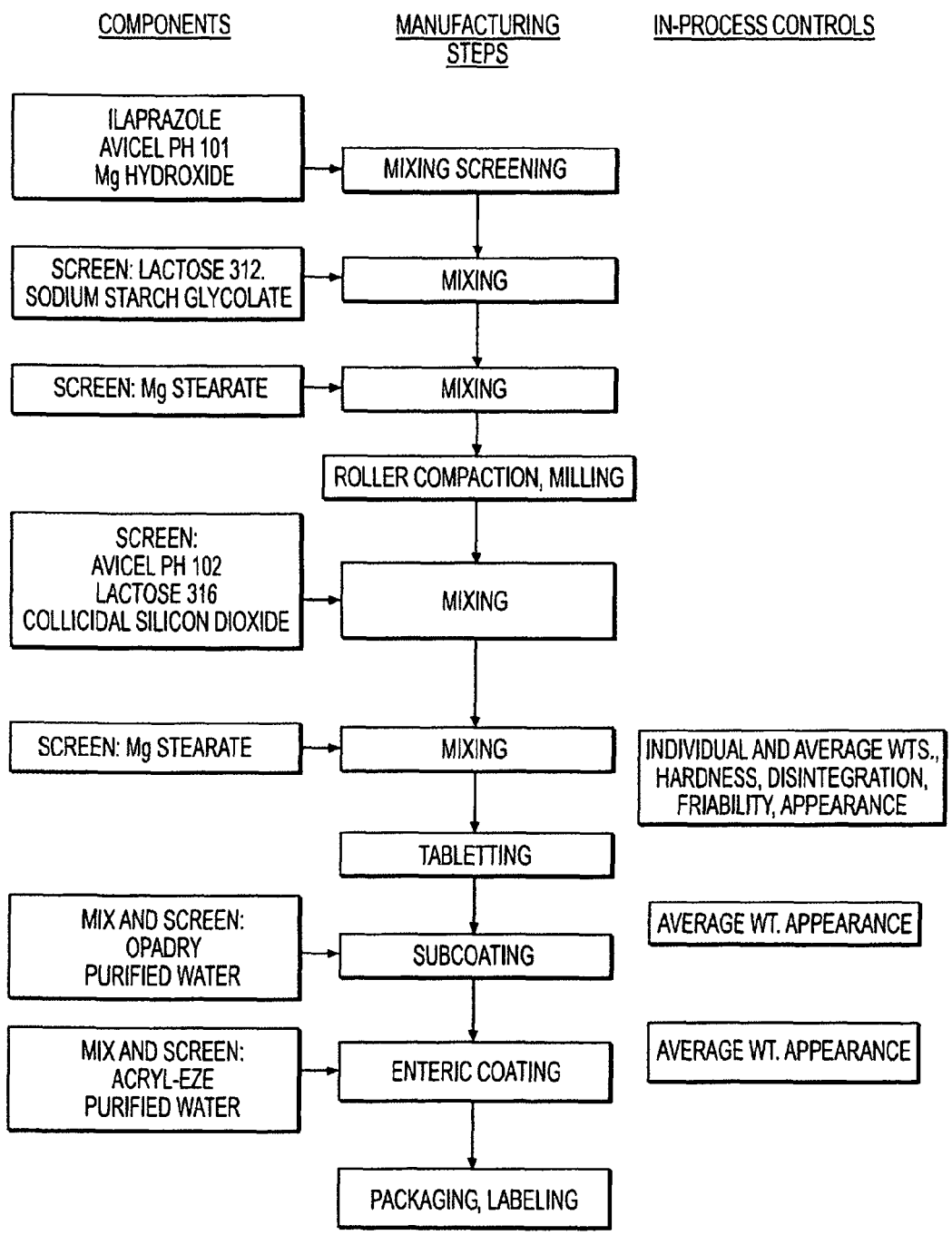
FIG. 55 depicts the tableting process for preparing a delayed release pharmaceutical composition of the invention.

Delayed release tablets containing 40 mg racemic ilaprazole, Form A, B, or F, were prepared and the dissolution rates of the tablets studied. The tablets were identical, with the exception of the crystalline form of ilaprazole. The qualitative and quantitative compositions of racemic ilaprazole delayed release tablets, 40 mg (inclusive of the compositions made using Forms A, B, and F) are described in Table 30. The delayed release tablets, 40 mg, were prepared according to the manufacturing process shown in FIG. 55.

TABLE 30

Composition of Delayed Release Tablets, 40 mg

| Ingredient | Quality Standard | Listed | Function | mg/tablet |
|---|---|---|---|---|
| Core Tablet | | | | |
| Racemic Ilaprazole (Form A, B, or F) | Internal | — | Active | 40.00 |
| Magnesium Hydroxide | USP | IID | Stabilizer | 40.00 |
| Microcrystalline Cellulose (Avicel PH 101) | NF | IID | Diluent/Binder | 58.75 |
| Lactose Monohydrate (Foremost Lactose 312) | NF | IID | Diluent | 58.75 |
| Microcrystalline Cellulose (Avicel PH 102) | NF | IID | Diluent/Binder | 58.75 |
| Lactose Monohydrate (Foremost Fast-Flo 316) | NF | IID | Diluent | 58.75 |
| Sodium Starch Glycolate (Explotab) | NF | IID | Disintegrant | 12.14 |
| Colloidal Silicon Dioxide (Cab-O-Sil M5P) | NF | IID | Glidant | 0.8983 |
| Magnesium Stearate | NF | IID | Lubricant | 1.980 |
| Subcoat | | | | |
| Opadry YS-1-19025-A Clear[1] | Internal | IID | Coating Material | 36.67 |
| Purified Water* | USP | N/A | Solvent | q.s. |
| Enteric Coating | | | | |
| Acryl-EZE 93F19255 Clear[2] | Internal | — | Enteric Coating | 36.67 |
| Purified Water* | USP | N/A | Solvent | q.s. |
| Total | | | | 403.4 |

*Removed during processing.
IID - indicates use of the ingredient is supported by FDA Inactive Ingredient Database.
q.s.—sufficient quantity
N/A—not applicable, solvents are removed during processing.
[1]Contains hypromellose, USP and polyethylene glycol 400, NF.
[2]Contains methacrylic acid copolymer type C, NF; polyethylene glycol 8000, NF; sodium bicarbonate, USP; colloidal anhydrous silica, NF; sodium lauryl sulfate, NF; and talc, USP.

The dissolution rate procedure was modified to be consistent with USP <711>, Delayed Release Method A and to change the UV detection wavelength in the acid stage of the test. For the acid stage, a wavelength of 340 nm was used, and for the buffer stage, a wavelength of 306 nm was used. The desired dissolution profile was Q=70% in 60 minutes. The dissolution profiles of the tablets containing racemic ilaprazole Forms A, B, and F are presented in Table 31.

TABLE 31

Dissolution Comparison of Delayed Release Tablets, 40 mg using Racemic Ilaprazole, Forms A, B, and F

| Racemic Ilaprazole Form in Tablet | Acid Stage % Dissolved in 2 hrs Average Min-Max | Buffer Stage Drug Release, % Dissolved Average Min-Max (% RSD) | | | |
|---|---|---|---|---|---|
| | | 15 min | 30 min | 45 min | 60 min |
| Form A | 1 0-2 | 54 48-61 (9.8) | 75 70-78 (4.1) | 82 79-87 (3.6) | 86 84-91 (3.3) |

TABLE 31-continued

Dissolution Comparison of Delayed Release Tablets, 40 mg using
Racemic Ilaprazole, Forms A, B, and F

| Racemic Ilaprazole Form in Tablet | Acid Stage % Dissolved in 2 hrs Average Min-Max | Buffer Stage Drug Release, % Dissolved Average Min-Max (% RSD) | | | |
|---|---|---|---|---|---|
| | | 15 min | 30 min | 45 min | 60 min |
| Form B* | 0 | 34 | 53 | 60 | 65 |
| | 0-0 | 1-43 (33.6) | 43-59 (8.3) | 52-68 (7.5) | 56-74 (7.4) |
| Form F | 0 | 43 | 71 | 83 | 89 |
| | 0-0 | 33-47 (13.0) | 66-74 (4.8) | 79-87 (4.6) | 85-95 (5.0) |

*Stage 1-3 testing conducted per USP. N = 24 results reported.

The relatively slower dissolution profile for the Form B tablet was unexpected based on the relative solubility data for of ilaprazole Forms A, F, and B (A<F<B). The tablets containing Form B drug had a relatively smaller particle size distribution compared to Form A and Form F. Form B was slower to wet and dissolve in the dissolution buffer than Form A and Form F.

Example 9

Bioavailability Study of Ilaprazole from Delayed-Release Tablets Containing Racemic Ilaprazole, Forms A, B, or F The bioavailability of ilaprazole from delayed-release tablets containing racemic ilaprazole, Form A, F, and B. This study were to assessed the bioavailability of ilaprazole from ilaprazole 40-mg delayed-release tablets manufactured as described in Example 8.

Study Design and Dose Administration: The subjects were randomly assigned in equal numbers to one of three sequence groups (Table 32).

TABLE 32

| | Regimen Sequences | | | |
|---|---|---|---|---|
| | Number | Regimen Sequence | | |
| Sequence | of Subjects | Period 1 | Period 2 | Period 3 |
| 1 | 16 | Form A | Form F | Form B |
| 2 | 16 | Form B | Form A | Form F |
| 3 | 16 | Form F | Form B | Form A |

Form A as a single ilaprazole 40-mg delayed-release tablet.
Form B as a single ilaprazole 40-mg delayed-release tablet.
Form F as a single ilaprazole 40-mg delayed-release tablet.
Note:
Study drug was administered with 240 mL of water following a minimum 10-hour fast. Subjects fasted for 4 hours post-dose.

Subjects received all regimens in a crossover fashion, according to the sequence group to which they were randomized. For each period, confinement began on Day 1 and ended on Day 2 after all procedures had been completed. There was a washout interval of at least 5 days between the doses of each period. Each subject received 3 doses of racemic ilaprazole 40 mg, each dose administered with 240 mL of water. On Day 1 of each period, subjects received the regimen to which they had been assigned at approximately 0800 hours. Subjects were fasted for 10 hours prior to dosing and remained fasted until 4 hours postdose when a standardized lunch was served.

Sample Collection and Bioanalysis: ilaprazole, ilaprazole sulfide and ilaprazole sulfone plasma concentrations were determined from 3 mL blood samples collected starting on Day 1 at 0 hour (predose), and 0.5, 1, 1.5, 2, 3, 4, 5, 6, 8, 10, 12, 14, 16, 20, 24, 28 and 32 hours postdose in each period. Plasma concentrations of ilaprazole were determined using a validated LC-MS/MS method at PPD (Middleton, Wis.). The lower limit of quantitation (LLOQ) for ilaprazole and its metabolites was 5.00 ng/mL with a 0.100 mL aliquot of plasma.

Pharmacokinetic and Statistical Analyses: Pharmacokinetic parameters for ilaprazole were estimated using standard noncompartmental methods with WinNonlin Professional Version 4.1 (Pharsight Co., Mountain View, Calif.).

Pharmacokinetic endpoints included time to reach the first quantifiable concentration ($t_{lag}$), time to reach the peak concentration ($t_{max}$), the peak plasma concentration ($C_{max}$), area under the plasma concentration versus time curve (AUC) from time zero to the last quantifiable concentration ($AUC_t$) and to infinity ($AUC_\infty$), terminal-phase elimination half-life ($t_{1/2z}$), apparent oral clearance (CL/F) and apparent volume of distribution ($V_z/F$).

For ilaprazole $t_{lag}$, $t_{max}$, and the natural logarithms of $C_{max}$ and AUCs, an analyses of variance (ANOVA) model was fined that included fixed effects of sequence, period, and crystal form as well as a random effect of subject nested within sequence. Pairwise comparisons between racemic ilaprazole, Forms B or F and Form A, were conducted. Ninety percent confidence intervals for relative bioavailability between regimens were computed.

Figure 56:
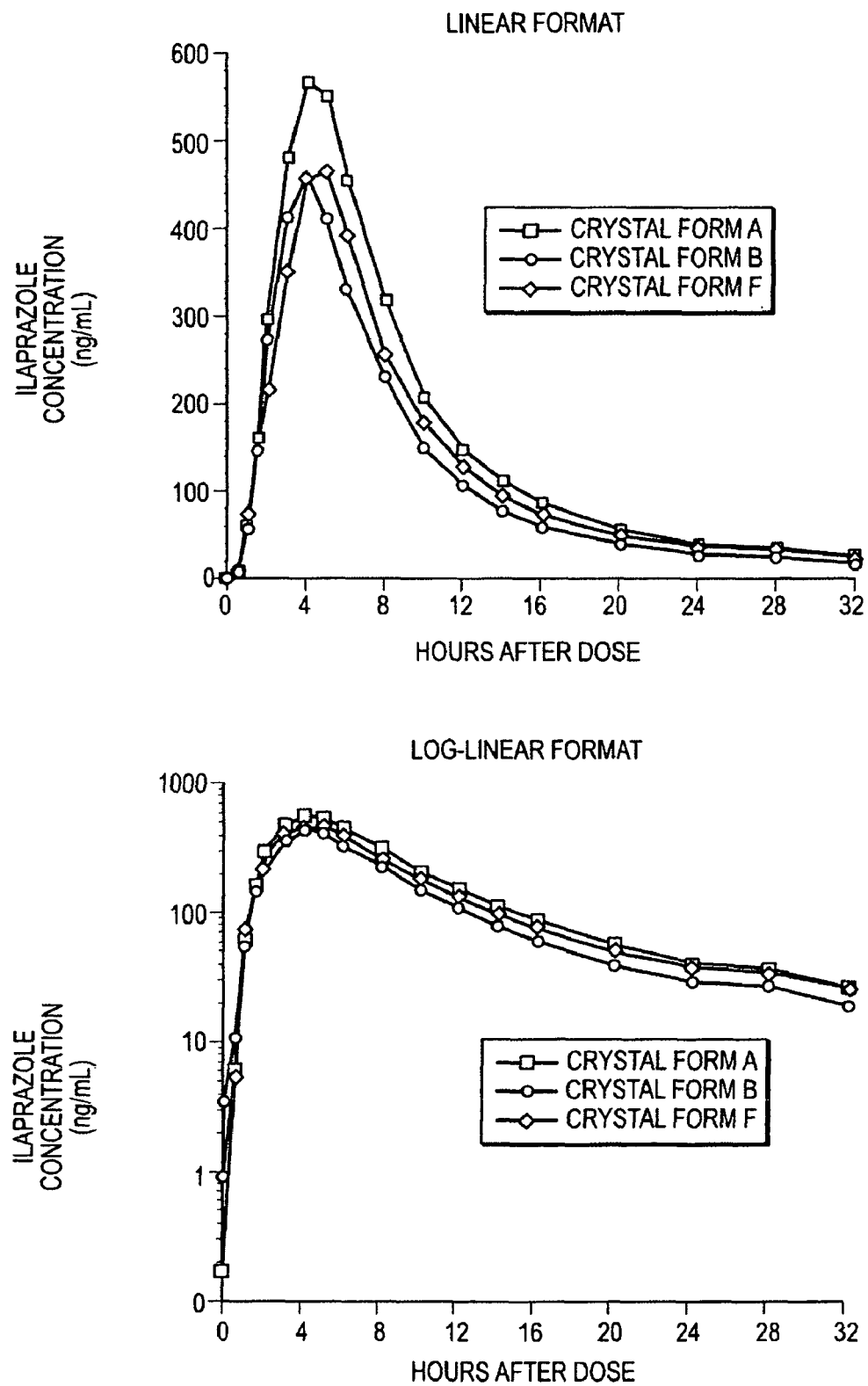
FIG. 56 shows mean plasma concentration versus time profiles of racemic ilaprazole following administration of a single 40 mg oral dose of ilaprazole as delayed-release tablets containing Forms A, B or F.

Pharmacokinetic Results Mean concentration vs. time profiles for ilaprazole (linear and log-linear Formats) following administration of a single 40 mg oral dose of ilaprazole as racemic ilaprazole, Form A, B or F, are presented in FIG. 56.

Mean pharmacokinetic parameter estimates for plasma ilaprazole concentrations following administration of a single 40 mg oral dose of racemic ilaprazole, Form A, B, or F, are presented in Table 33.

TABLE 33

Plasma Pharmacokinetic Parameter Estimates of Ilaprazole in Healthy Adult Subjects Following Administration of a Single 5 mg Oral Dose of Racemic Ilaprazole, Forms A, B or F

|  | $t_{lag}$ (h) | $t_{max}$ (h) | $C_{max}$ (ng/mL) | $AUC_t$ (ng · h/mL) | $AUC_\infty$ (ng · h/mL) | $t_{1/2z}$ (h)[a] | CL/F (L/h) | Vz/F (L) |
|---|---|---|---|---|---|---|---|---|
| Form A | | | | | | | | |
| N | 44 | 44 | 44 | 44 | 44 | 44 | 44 | 44 |
| Mean | 1.16 | 4.14 | 651.68 | 5066.75 | 5454.11 | 8.89 (6.95) | 9.34 | 111.60 |
| CV % | 62 | 24 | 49 | 40 | 38 | 60 | 70 | 81 |
| Form B | | | | | | | | |
| N | 44 | 44 | 44 | 44 | 44 | 44 | 44 | 44 |
| Mean | 1.22 | 3.50 | 522.51 | 3812.50 | 4087.99 | 9.48 (7.76) | 11.70 | 160.34 |
| CV % | 65 | 36 | 38 | 37 | 36 | 63 | 52 | 76 |
| Form F | | | | | | | | |
| N | 44 | 44 | 44 | 44 | 44 | 44 | 44 | 44 |
| Mean | 1.18 | 4.01 | 554.18 | 4256.66 | 4672.37 | 9.66 (7.29) | 11.29 | 134.72 |
| CV % | 90 | 26 | 50 | 43 | 40 | 52 | 81 | 54 |

[a]Arithmetic mean (harmonic mean).

Ilaprazole $t_{lag}$ and $t_{max}$ were similar regardless of the crystal form of racemic ilaprazole that was administered. Ilaprazole mean $t_{lag}$ averaged about 1.2 hours, and the mean $t_{max}$ ranged from 3.5 to 4.1 hours. Ilaprazole mean $C_{max}$ and AUC values were highest for Form A and lowest for Form B. The mean $C_{max}$ and $AUC_\infty$ values for ilaprazole from Form B were approximately 20% and 25% lower, respectively, than those values observed for Form A. The mean $C_{max}$ and $AUC_\infty$ values for ilaprazole from Form F were approximately 15% and 14% lower, respectively, than those values observed for Form A. The harmonic mean $t_{1/2z}$ values were similar for the Forms A, B, and F, and ranged from approximately 7.0 to 7.8 hours. The mean apparent oral clearance and volume of distribution values were highest for Form B and lowest for Form A. The results of the statistical analysis of the ANOVA are summarized in Table 34.

TABLE 34

Statistical Comparison of Pharmacokinetic Parameter Estimates for Racemic Ilaprazole, Forms A, B, and F

| Parameter | Point Estimate | 90% Confidence Interval |
|---|---|---|
| (i) | Regimen B vs. Regimen A | |
| $C_{max}$ | 0.8292 | 0.7185-0.9570 |
| $AUC_t$ | 0.7630 | 0.6646-0.8759 |
| $AUC_\infty$ | 0.7609 | 0.6624-0.8740 |
| (ii) | Regimen C vs. Regimen A | |
| $C_{max}$ | 0.8456 | 0.7327-0.9759 |
| $AUC_t$ | 0.8288 | 0.7220-0.9515 |
| $AUC_\infty$ | 0.8456 | 0.7362-0.9713 |

Regimen A: Form A as a single ilaprazole 40-mg delayed-release tablet.
Regimen B: Form B as a single ilaprazole 40-mg delayed-release tablet.
Regimen C: Form F as a single ilaprazole 40-mg delayed-release tablet.

The lower bounds of the 90% confidence intervals for the ratios of the central values when racemic ilaprazole was administered as a single oral dose of the 40-mg tablet as Form B (Regimen B), relative to a single oral dose of the 40-mg tablet as Form A (Regimen A), were below the lower bioequivalence limit of 0.80 for $C_{max}$, AUC, and $AUC_\infty$, and the confidence intervals did not include 1. For $C_{max}$ and AUC, the point estimate indicated that the values for Form B were approximately 17% and 24% lower, respectively, than those observed for Form A.

The lower bounds of the 90% confidence intervals for the ratios of the central values when ilaprazole was administered as a single oral dose of the 40-mg tablet as Form F (Regimen C), relative to a single oral dose of the 40-mg tablet as Form A (Regmen A), were below the lower bioequivalence limit of 0.80 for $C_{max}$, AUC, and $AUC_\infty$, and the confidence intervals did not include 1. The point estimates indicated that ilaprazole $C_{max}$ and AUC values following administration of Form F were approximately 15% and 15-17% lower, respectively, than those observed for Form A.

Pharmacokinetic Summary: Following administration of a single 40-mg oral dose of ilaprazole as delayed-release tablets containing Form B, the total systemic exposure, as measured by ilaprazole $C_{max}$ and AUC, was approximately 17% and 24% lower, respectively, relative to a single 40-mg oral dose of ilaprazole as delayed-release tablets containing Form A.

Following administration of a single 40-mg oral dose of ilaprazole as delayed-release tablets containing Form F, the total systemic exposure, as measured by ilaprazole $C_{max}$ and AUC, was approximately 15% and 15-17% lower, respectively, relative to a single 40-mg oral dose of ilaprazole as delayed-release tablets containing Form A.

Example 10

Figure 57:
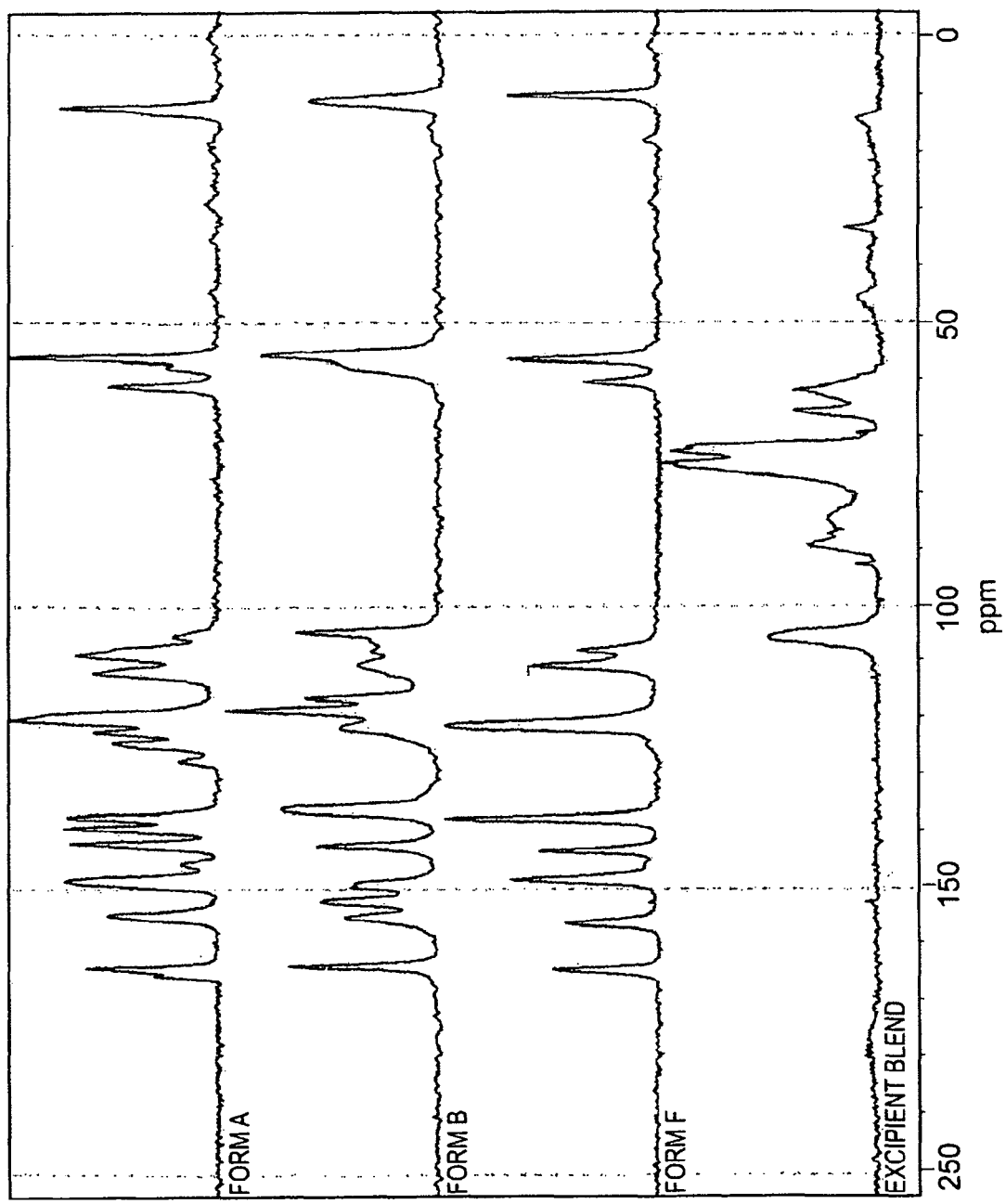
FIG. 57 shows the $^{13}$C CP/MAS ssNMR spectra of delayed-release formulations containing 40 mg of racemic ilaprazole, Forms A, B, and F.

Solid State $^{13}$C NMR Study of Racemic flaprazole, Forms A, B, F, in 40 mg Extended-Release Formulations The delayed release tablets containing 40 mg of racemic ilaprazole, Forms A, B, and F, were studied using $^{13}$C CP/MAS ssNMR. The estimated level of detection for each form as a minor impurity in the major form was approximately 15% for all three forms. To ensure that approximately the same response can be obtained for all three forms and to ensure that the observed forms do not have a high or low response, the relaxation delay and cross-polarization contact times were independently optimized for each crystalline form of ilaprazole. All three forms had an optimal relaxation delay of 10 seconds, and an optimal cross-polarization contact time of 4 milliseconds, which conditions were used for the study. As shown in FIG. 57, $^{13}$C CP/MAS ssNMR shows good specificity for each form. FIG. 57 demonstrates that the regions with the best specificity for the three forms do not overlap with the peaks of the 40 mg excipient-only placebo blend. The peak positions for each form and placebo blend are summarized in Table 35. Four characteristic peaks were chosen for each form that are suitable for form identification as a neat API and in tableted form and are listed in Table 36.

TABLE 35

Racemic Ilaprazole $^{13}$C CP/MAS ssNMR Peak Positions for Delayed-Release Formulations Containing Forms A, B, and F and the Placebo Blend Peak Position (ppm)

| Form A | Form B | Form F | 40 mg Placebo Blend |
|---|---|---|---|
| 165.1 | 163.5 | 164.2 | 179.3 |
| 163.9 |  | 156.1 | 152.4 |
| 154.7 | 155 | 148.4 | 105.5 |
|  | 152.2 |  |  |
| 148.5 | 149.5 |  | 92.8 |
| 145.3 | 142.2 | 143.2 | 89.3 |
| 141.8 |  |  | 87.2 |
| 139.1 |  |  | 84.0 |
| 137.2 | 135.7 | 137.5 | 74.7 |
| 127.4 |  |  | 72.7 |
| 124.1 |  |  | 71.8 |
| 122.2 | 121.5 | 121.0 | 69.4 |
| 120.1 | 118.3 |  | 65.5 |
|  | 116.2 |  |  |
| 111.8[a] | 110.3[a] | 110.6[a] | 62.0 |
| 108.6[a] | 107.8[a] | 107.8[a] | 45.5 |
| 105.2[a] | 104.5[a] |  | 37 |
| 61.1[a] |  | 60.4[a] | 33.4 |
| 57.7[a] |  |  | 21.8 |
| 56.2[a] | 55.7[a] | 56.4[a] | 14.4 |
| 12.6 | 11.5 | 10.5 |  |

[a]Peaks that do not show specificity compared to placebo blend peaks.

TABLE 36

Racemic Ilaprazole $^{13}$C CP/MAS ssNMR Peak Positions for Delayed-Release Formulations Containing Forms A, B, and F Characteristic Peak Positions Approximate Peak Positions (ppm)

| Form A | Form B | Form F |
|---|---|---|
| 139.1 | 152.2 | 156.1 |
| 127.4 | 135.7 | 143.2 |
| 124.1 | 116.2 | 110.6 |
| 12.6 | 11.5 | 10.5 |

The claimed invention is:

1. A crystalline form of racemic ilaprazole characterized by a solid state $^{13}$C CP/MAS NMR spectra having peaks at 139.1, 127.4, 124.1, and 12.6.

2. The crystalline form of racemic ilaprazole of claim 1, further characterized by a differential scanning calorimetry thermogram having an onset temperature of about 167° C.

3. The crystalline form of racemic ilaprazole of claim 1, further characterized by a powder x-ray diffraction pattern having peaks at 8.0° 2θ±0.2° 2θ, 13.2° 2θ±0.2° 2θ, and 24.1° 2θ±0.2° 2θ.

* * * * *